(12) United States Patent
Chen et al.

(10) Patent No.: US 12,141,097 B2
(45) Date of Patent: *Nov. 12, 2024

(54) METHOD AND SYSTEM FOR PROVIDING PRE-APPROVED A/A DATA BUCKETS

(71) Applicant: YAHOO ASSETS LLC, New York, NY (US)

(72) Inventors: Russell Chen, Oakland, CA (US); Miao Chen, Sunnyvale, CA (US); Don Matheson, Denver, CO (US); Mahendrasinh Ramsinh Jadav, San Jose, CA (US)

(73) Assignee: YAHOO ASSETS LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/365,558

(22) Filed: Aug. 4, 2023

(65) Prior Publication Data

US 2023/0385238 A1 Nov. 30, 2023

Related U.S. Application Data

(63) Continuation of application No. 17/467,127, filed on Sep. 3, 2021, now Pat. No. 11,726,958, which is a
(Continued)

(51) Int. Cl.
*G06F 16/14* (2019.01)
*G06F 12/1018* (2016.01)
(Continued)

(52) U.S. Cl.
CPC ........ *G06F 16/152* (2019.01); *G06F 12/1018* (2013.01); *G06F 16/24578* (2019.01);
(Continued)

(58) Field of Classification Search
CPC ...................................................... G06F 16/152
(Continued)

(56) References Cited

U.S. PATENT DOCUMENTS 8,090,703 B1 1/2012 Agarwal et al.
8,234,632 B1 7/2012 Hugeback et al.
(Continued)

OTHER PUBLICATIONS

Blundell et al. "Evaluation methods for non-experimental data" Fiscal studies (2000) vol. 21, No. 4 pp. 427-468—Wiley Online Library (Year: 2000).
(Continued)

*Primary Examiner* — Muluemebet Gurmu
(74) *Attorney, Agent, or Firm* — Venable LLP

(57) ABSTRACT

The present teaching generally relates to detecting providing pre-validated data buckets for online experiments. In a non-limiting embodiment, user activity data representing user activity for a first plurality of user identifiers may be obtained. A first set of values and a second values, representing first and second user engagement parameters, respectively, may be generated for each user identifier based on the user activity data. A first ranking and a second ranking may be determined for the first and second sets, respectively. A first exclusion range including a first number of values to be removed from the first and second sets may be determined. A homogenous value set may be generated by removing the first number of values from the first and second sets, where each value from the homogenous value set corresponds to a user identifier available to be placed in a data bucket for an online experiment.

11 Claims, 41 Drawing Sheets

Related U.S. Application Data continuation of application No. 15/677,724, filed on Aug. 15, 2017, now Pat. No. 11,226,931.

(51) Int. Cl.

| | |
|---|---|
| *G06F 16/2457* | (2019.01) |
| *G06F 16/435* | (2019.01) |
| *G06Q 50/10* | (2012.01) |
| *G16H 10/40* | (2018.01) |
| *H04L 67/02* | (2022.01) |
| *H04L 67/50* | (2022.01) |

(52) U.S. Cl.
CPC .......... *G06F 16/435* (2019.01); *G06Q 50/10* (2013.01); *G16H 10/40* (2018.01); *H04L 67/02* (2013.01); *H04L 67/535* (2022.05)

(58) Field of Classification Search
USPC ........................................................ 707/748
See application file for complete search history.

(56) References Cited

U.S. PATENT DOCUMENTS

| | | | |
|---|---|---|---|
| 9,268,663 B1 | 2/2016 | Siddiqui et al. | |
| 10,185,970 B1* | 1/2019 | Chen ................ | G06Q 30/0243 |
| 2002/0147570 A1 | 10/2002 | Kraft et al. | |
| 2007/0234779 A1 | 10/2007 | Hsu et al. | |
| 2010/0082640 A1* | 4/2010 | Wexler ............... | G06F 16/9535 |
| | | | 707/E17.014 |
| 2011/0125571 A1* | 5/2011 | Jagadish ............ | G06Q 30/0256 |
| | | | 705/14.54 |
| 2014/0082593 A1 | 3/2014 | Alper et al. | |
| 2014/0236964 A1 | 8/2014 | Dalessio et al. | |
| 2014/0289419 A1 | 9/2014 | Vijayant | |
| 2014/0330732 A1 | 11/2014 | Grignon | |
| 2015/0039424 A1 | 2/2015 | Narravula et al. | |
| 2015/0186403 A1 | 7/2015 | Srivastava et al. | |
| 2015/0379430 A1* | 12/2015 | Dirac ..................... | G06N 20/00 |
| | | | 706/12 |
| 2016/0253311 A1* | 9/2016 | Xu ......................... | G06Q 50/01 |
| | | | 715/256 |
| 2016/0253683 A1 | 9/2016 | Gui et al. | |
| 2017/0046622 A1 | 2/2017 | Gather et al. | |
| 2017/0104683 A1 | 4/2017 | Parthasarathy | |
| 2017/0128838 A1 | 5/2017 | Burge et al. | |
| 2017/0318152 A1 | 11/2017 | Chen et al. | |
| 2017/0323329 A1 | 11/2017 | Katariya et al. | |
| 2017/0323331 A1 | 11/2017 | Malek et al. | |
| 2017/0330114 A1 | 11/2017 | Ghavamzadeh et al. | |
| 2017/0364958 A1 | 12/2017 | Kirti | |
| 2018/0034271 A1 | 2/2018 | Lam | |
| 2018/0089188 A1* | 3/2018 | Kharisma ........... | G06F 16/2462 |
| 2018/0089716 A1 | 3/2018 | Xu et al. | |
| 2018/0121503 A1 | 5/2018 | Bakke et al. | |
| 2018/0144426 A1 | 5/2018 | Grbac et al. | |

OTHER PUBLICATIONS

Kharitonov et al. "Sequential testing for early stopping of on line experiments",—Proceedings of the 38th . . . , 2015—dl.acm.org (Year: 2015).

Crook et al. "Seven pitfalls to avoid when running controlled experiments on the web" Proceedings of the 15th . . . , 2009—dl. acm.org (Year: 2009).

Goswami et al. "Controlled experiments for decision-making in e-commerce search"—Big Data (Big Data), 2015 . . . , 2015—ieeexplore.ieee.org (Year: 2015).

Chang "Detecting and avoiding bucket imbalance in A/B tests"; published on Dec. 28, 2015, retrieved on Aug. 13, 2021 from https://blog.twitter.com/engineering/en_us/a/2015/detecting-and-avoiding-bucket-imbalance-in-ab-tests (Year: 2015).

Deng et al. "Continuous monitoring of A/B tests without pain: Optional stopping in Bayesian testing" Data Science and Advanced Analytics . . . , 2016—ieeexplore.ieee.org (Year: 2016).

Xu et al. "From infrastructure to culture: A/B testing challenges in large scale social networks" Proceedings of the 21th . . . , 2015—dl.acm.org (Year: 2015).

Kohavi et al. "Online controlled experiments at large scale" "Proceedings of the 19th . . . , 2013—dl.acm.org (Year: 2013)".

Zhao et al. "Online experimentation diagnosis and troubleshooting beyond AA validation" 2016 IEEE International . . . , 2016—ieeexplore.ieee.org (Year: 2016).

Tang et al. "Overlapping experiment infrastructure: More, better, faster experimentation" Proceedings of the 16th ACM . . . , 2010—dl.acm.org (Year: 2010).

Savoie "9 Common Mistakes that Will Kill Your A/B Testing"; published on Jan. 27, 2017, retrieved on Aug. 13, 2021 from https://www.adpushup.com/blog/9-common-mistakes-that-wi ll-ki ll-your-ab-testing/ (Year: 2017).

The Design of Experiments, retrieved from "https://en.wikipedia.org/wiki/The_Design_of_Experiments" on Feb. 15, 2020. (Year: 2020).

Kohavi et al. "Trustworthy online controlled experiments: Five puzzling outcomes explained" Proceedings of the 18th . . . , 2012—dl.acm.org (Year: 2012).

Kohavi et al. "Unexpected results in online controlled experiments" ACM SIGKDD Explorations Newsletter, 2011—dl.acm.org (Year: 2011) .

Fang et al. "Uniform design: theory and application" Technometrics, 2000—amstat.tandfonline.com (Year: 2000).

Coey et al., "People and Cookies: Imperfect Treatment Assignment in Online Experiments", Proceedings of the 25th International Conference on World Wide Web, Apr. 11-15, 2016, pp. 1103-1111, Montreal, Quebec, Canada.

\* cited by examiner

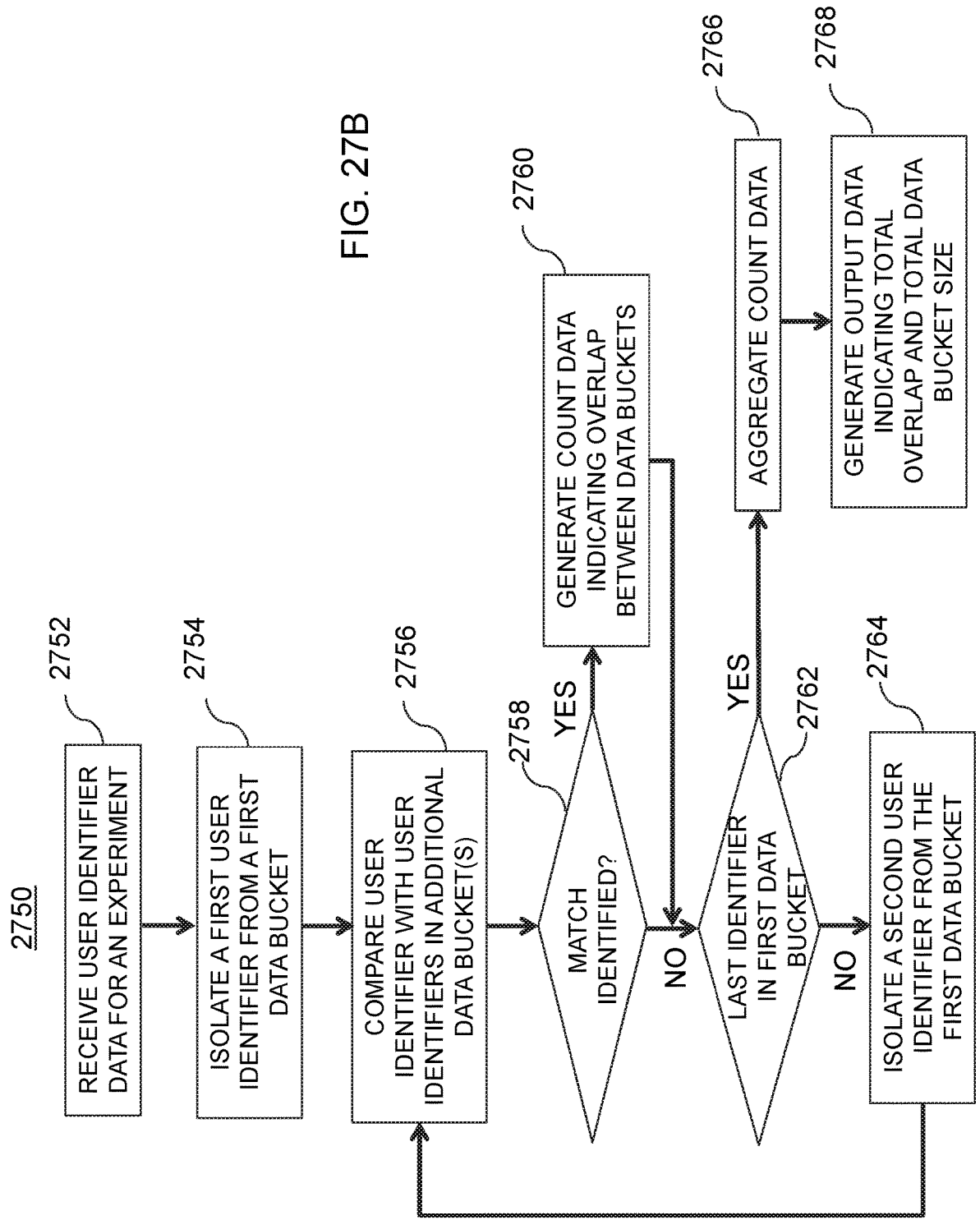

METHOD AND SYSTEM FOR PROVIDING PRE-APPROVED A/A DATA BUCKETS

CROSS REFERENCE TO RELATED APPLICATIONS

This application is a continuation of U.S. patent application Ser. No. 17/467,127, filed on Sep. 3, 2021, entitled "Method and System for Providing Pre-Approved A/A Data Buckets", which is a continuation of U.S. patent application Ser. No. 15/677,724, filed on Aug. 15, 2017, entitled "Method and System for Providing Pre-Approved A/A Data Buckets", both of which are hereby incorporated by reference in their entireties.

This application is related to commonly-assigned U.S. patent application Ser. No. 15/677,925, entitled "METHOD AND SYSTEM FOR DETECTING GAPS IN DATA BUCKETS FOR A/B EXPERIMENTATION," and U.S. patent application Ser. No. 15/677,917, entitled "METHOD AND SYSTEM FOR DETECTING DATA BUCKET INCONSISTENCIES FOR A/B EXPERIMENTATION," each of which are incorporated herein by reference in their entireties.

BACKGROUND

Technical Field

The present teaching generally relates to online experimentation. More specifically, the present teachings relate to providing pre-approved A/A data buckets. Further, the present teachings relate to detecting and monitoring a gap in data buckets for online experimentation. Still further, the present teachings relate to detecting and monitoring inconsistencies in data buckets for online experimentation.

Technical Background

In the age of the Internet, online experimentation, and in particular controlled online experimentation, is a commonly used and effective tool for product development. One such type of controlled online experiment is A/B testing. A/B testing in a more classical sense corresponds to having two (or more) groups, where one group—the control group—is given a controlled experience, while another group (or groups) are given a test experience. For example, in drug tests, a control group may receive a placebo while a test group may receive a test drug. In online experimentation, one set of users may receive one user experience at their user device, while another set of users may receive a different user experience. This allows a service provider to gauge an effectiveness of the user experience based on various user metrics computed for each of the various users of each set of users. For example, a service provider may test an effectiveness of a new website format (experimental user experience) against an original website format (control user experience). Users accessing the website via their user devices may randomly be provided with one of the new website format or the original website format, and user interaction metrics (e.g., clicks, scrolls, advertisement impressions, click-through-rate, etc.) may be computed for each website format for each user to determine how "effective" the new website format is as compared to the original website experience.

There are some requirements to these types of online experiments in order for the results to be accurate. For example, the two or more groups (e.g., control group and experimental group(s)) should include users that are randomly selected without any predisposition. Additionally, a user placed into one group should remain in that group throughout the duration of the experiment. Further still, the size (e.g., number of users) in each group should be substantially equal. Failure to adhere to these conditions may result in compromised results that do not accurately reflect the outcome that is obtained.

One way to prevent potential errors in the experimentation process is to perform A/A validation. A/A validation, for example, serves to try and validate the control and experimentation groups, or in the case of online experimentation, the control data bucket and the experimentation data bucket(s). This includes determining whether or not there are any pre-existing differences in the control and/or experimentation buckets, as well as determining whether or not there are any systematic errors in the experimentation system that would lead to unexpected results.

Typically, A/A validation takes time. For example, in order for data to be obtained and analyzed, four to five days' worth of data may be needed. Additionally, it may be expected for some data buckets of online experiments to fail the A/A validation process. Therefore, it is common for experimenters to open more data buckets for the A/A validation process then may actually be needed. This may cause the experimenter to have to decide which data bucket, if any, to use for the experiment. These issues, amongst various others, may cause a delay in the start of an online experiment, which in the ever evolving and fast paced online world, is undesirable.

When online experiments are performed, as mentioned above, users may be placed into one of a control group or an experimentation group. In certain scenarios, a single experiment may include two or more experimentation groups, depending on the conditions and aspects sought to be tested by the experimenter. Each of the control group and the experimentation group (or groups) is designed such that they have a same size. For example, a control data bucket may be designed such that it is to include 10,000 randomly selected users, while an experimental data bucket may also be designed such that it is to include 10,000 randomly selected, but different, users. If, during or after experimentation it is determined that one or more of these data buckets included substantially less than the designed number of users, the results of the experiment may be compromised. For example, if the data buckets were designed to include 10,000 users, but after the experiment it is determined that the data bucket online includes 7,000 users, this may lead to inaccurate results. Inaccurate results may corrupt the data, and undermine the findings of that experiment.

Further still, when placing users in one of the control data buckets or one of the one or more experimental data buckets, it is believed that each user will only be placed in one of these data buckets. Intuitively, if a user is to be placed in both the control data bucket and the experimental data bucket, this may lead to compromised results. Similarly, if a user is placed in two different experimental data buckets, inconsistent results across these two data buckets will arise.

Each of these issues, as described above, are further exacerbated by the platform of online experimentation as the number of users is extremely large, and the time scale of randomly selecting and placing a user into a data bucket, and rolling out various user experiences is very small.

Therefore, providing techniques to reduce the amount of time needed to validate and accuracy of data buckets for use create online experiments is needed. Further, providing techniques to identify a gap between an expected data bucket size and an actual data bucket size is needed. Still further, providing techniques to identify inconsistencies between data buckets is needed.

SUMMARY

The teachings disclosed herein generally relate to methods, systems, and programming for providing data buckets for online experiments. The teachings disclosed herein further generally relate to methods, systems, and programming for detecting data bucket discrepancies associated with online experiments. The teachings disclosed herein still further generally relate to methods, systems, and programming for identifying data bucket overlap with online experiments.

In one example, a method for providing data buckets for online experiments may be implemented on at least one machine including at least one processor, memory, and communications circuitry is described. User activity data representing user activity for a first plurality of user identifiers may be obtained. A first set of values representing a first user engagement parameter for each user identifier of the first plurality may be generated based on the user activity data, and a second set of values representing a second user engagement parameter for each user identifier of the first plurality may also be generated based on the user activity data. A first ranking for the first set may be determined, and a second ranking for the second set may also be determined. A first exclusion range including a first number of values to be removed from the first set and the second set may be determined. A homogenous value set may be generated by removing the first number of values from the first set and the second set, where each value from the homogenous value set corresponds to a user identifier that is available to be placed in a data bucket for an online experiment.

In another example, a system for providing data buckets for online experimentation is described. The system includes a metric computation system configured to obtain user activity data representing user activity for a first plurality of user identifiers, generate a first set of values representing a first user engagement parameter for each user identifier of the first plurality based on the user activity, and generate a second set of values representing a second user engagement parameter for each user identifier of the first plurality based on the user activity. The system also includes a hash value ranker configured to determine a first ranking for the first set, and determine a second ranking for the second set. The system further includes a hash value exclusion system configured to determine a first exclusion range including a first number of values to be removed from the first set and the second set. The system still further includes a hash value selector system configured to generate a homogenous value set by removing the first number of values from the first set and the second set, wherein each value from the homogenous value set corresponds to a user identifier that is available to be placed in a data bucket for an online experiment.

Other concepts relate to software for implementing the present teaching on providing data buckets for online experiments. A software product, in accord with this concept, includes at least one machine-readable non-transitory medium and information carried by the medium. The information carried by the medium may be executable program code data, parameters in association with the executable program code, and/or information related to a user, a request, content, or information related to a social group, etc.

In one example, a non-transitory computer readable medium having instructions recorded thereon for providing data buckets for online experiments is described. The instructions, when read by a computer, causes the computer to obtain user activity data representing user activity for a first plurality of user identifiers, generate a first set of values representing a first user engagement parameter for each user identifier of the first plurality based on the user activity, and generate a second set of values representing a second user engagement parameter for each user identifier of the first plurality based on the user activity. The instructions further, when read by the computer, causes the computer to determine a first ranking for the first set, and determine a second ranking for the second set. The instructions further, when read by the computer, causes the computer to determine a first exclusion range including a first number of values to be removed from the first set and the second set, and to generate a homogenous value set by removing the first number of values from the first set and the second set, where each value from the homogenous value set corresponds to a user identifier that is available to be placed in a data bucket for an online experiment.

In yet another example, a method for detecting data bucket discrepancies associated with online experiments implemented on at least one machine including at least one processor, memory, and communications circuitry is described. A monitoring layer may be generated within an online experimentation platform. The online experimentation platform may include at least a first layer, where a first online experiment is associated with the first layer, the monitoring layer includes a monitoring layer data bucket, and the first layer includes at least a first data bucket. First data representing user activity associated with a first plurality of identifiers may be obtained, the user activity being associated with the first layer. Second data including representing at least one user engagement parameter may be generated based on the first data. A first discrepancy between the first data and the second data may be determined, where the first discrepancy indicates a first amount of identifiers that include a first metadata tag associated with the first layer and lack a second metadata tag associated with the monitoring layer.

In still yet another example, a system for detecting data bucket discrepancies associated with online experiments is described. The system includes an experimentation system configured to generate a monitoring layer within an online experimentation platform. The experimentation platform includes at least a first layer, and where a first online experiment is associated with the first layer, the monitoring layer includes a monitoring layer data bucket, and the first layer comprises at least a first data bucket. The system also includes a discrepancy detection system configured to obtain first data representing user activity associated with a first plurality of identifiers, the user activity being associated with the first layer. The discrepancy detection system is further configured to determine a first discrepancy between the first data and the second data, where the first discrepancy indicates a first amount of identifiers that include a first metadata tag associated with the first layer and lack a second metadata tag associated with the monitoring layer.

Other concepts relate to software for implementing the present teaching on detecting data bucket discrepancies associated with online experiments. A software product, in accord with this concept, includes at least one machine-readable non-transitory medium and information carried by the medium. The information carried by the medium may be executable program code data, parameters in association with the executable program code, and/or information related to a user, a request, content, or information related to a social group, etc.

In one example, a non-transitory computer readable medium having instructions recorded thereon for detecting data bucket discrepancies associated with online experiments. The instructions, when read by a computer, cause the computer to generate a monitoring layer within an online experimentation platform. The experimentation platform may include at least a first layer, and where a first online experiment is associated with the first layer, the monitoring layer includes a monitoring layer data bucket, and the first layer includes at least a first data bucket. The instructions, when read by the computer, also causes the computer to obtain first data representing user activity associated with a first plurality of identifiers, the user activity being associated with the first layer. The instructions, when read by the computer, further cause the computer to generate second data representing at least one user engagement parameter based on the first data. The instructions, when read by the computer, still further cause the computer to determine a first discrepancy between the first data and the second data, where the first discrepancy indicates a first amount of identifiers that include a first metadata tag associated with the first layer and lack a second metadata tag associated with the monitoring layer.

In still yet another example, a method for identifying data bucket overlap with online experiments implemented on at least one machine including at least one processor, memory, and communications circuitry is described. First data representing a first set of identifiers associated with a first data bucket of a first online experiment may be obtained. Second data representing a second set of identifiers associated with a second data bucket of the first online experiment may be obtained. Based on the first data and the second data, a first number of identifiers that are associated with the first data bucket and the second data bucket may be determined. In response to determining that the first number exceeds a threshold, a data flag may be generated that indicates that results associated with the first online experiment are inconsistent.

In still further yet another example, a system for identifying data bucket overlap with online experiments is described. The system includes a user identifier extraction system configured to obtain first data representing a first set of identifiers associated with a first data bucket of a first online experiment, and obtain second data representing a second set of identifiers associated with a second data bucket of the first online experiment. The system further includes a user identification comparison system configured to determine, based on the first data and the second data, a first number of identifiers that are associated with the first data bucket and the second data bucket. The system still further includes a data bucket abnormality system configured to generate, in response to determining that the first number exceeds a threshold, a data flag indicating that the results associated with the first online experiment are inconsistent.

Other concepts relate to software for implementing the present teaching on identifying data bucket overlap with online experiments. A software product, in accord with this concept, includes at least one machine-readable non-transitory medium and information carried by the medium. The information carried by the medium may be executable program code data, parameters in association with the executable program code, and/or information related to a user, a request, content, or information related to a social group, etc.

In one example, a non-transitory computer readable medium having information recorded thereon for identifying data bucket overlap with online experiments. The information, when read by a computer, causes the computer to obtain first data representing a first set of identifiers associated with a first data bucket of a first online experiment, and obtain second data representing a second set of identifiers associated with a second data bucket of the first online experiment. The information, when read by the computer, further causes the computer determine, based on the first data and the second data, a first number of identifiers that are associated with the first data bucket and the second data bucket. The information, when read by the computer, still further causes the computer to generate, in response to determining that the first number exceeds a threshold, a data flag indicating that results associated with the first online experiment are inconsistent.

Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF THE DRAWINGS

The methods, systems and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 27B is an illustrative flowchart of an exemplary process for generating data indicating overlap, in accordance with various embodiments of the present teachings;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The present disclosure generally relates to systems, methods, medium, and other implementations for providing data buckets for online experiments. The present disclosure generally relates to systems, methods, medium, and other implementations for detecting data bucket discrepancies associated with online experiments. The present disclosure generally relates to systems, methods, medium, and other implementations for identifying data bucket overlap with online experiments.

Figure 1:
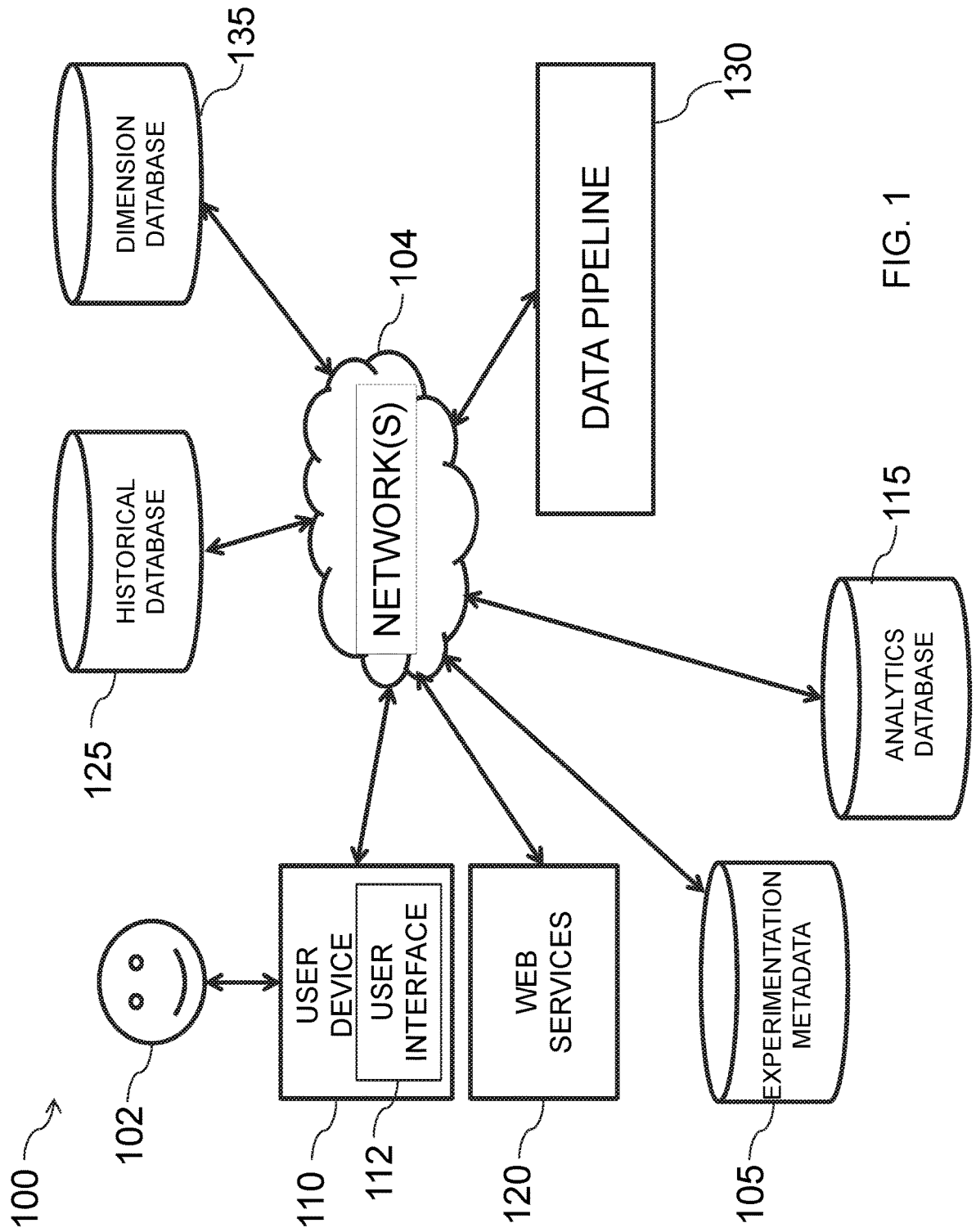
FIG. 1 is an illustrative diagram of an exemplary system for providing valid data buckets for an online experiment, in accordance with various embodiments of the present teachings.

FIG. 1 is an illustrative diagram of an exemplary system for providing valid data buckets for an online experiment, in accordance with various embodiments of the present teachings. In the non-limiting example embodiment, an exemplary system 100 is described. System 100 includes, in one embodiment, a user device 110. A user 102 may interact with user device 110, for example, via user interface 112. User device 102 may correspond to any suitable type of electronic device including, but are not limited to, desktop computers, mobile computers (e.g., laptops, ultrabooks), mobile phones, smart phones, tablets, televisions, set top boxes, smart televisions, personal display devices, personal digital assistants ("PDAs"), gaming consoles and/or devices, smart household devices (e.g., refrigerators, microwaves, etc.), smart vehicles (e.g., cars, trucks, motorcycles, etc.), smart transportation devices (e.g., boats, ships, trains, airplanes, etc.), wearable devices (e.g., watches, pins/broaches, headphones, etc.), and/or smart accessories (e.g., light bulbs, light switches, electrical switches, etc.). Although only one user device 110 is shown within system 100, persons of ordinary skill in the art will recognize that any suitable number of user devices may be included within system 100. Furthermore, various additional details related to user device 110 are described in greater detail below.

In one embodiment, user 102 may access content and/or perform one or more actions using user device 110. In some embodiments, user 102 may access content, such as a website, hosted by a provider by inputting a uniform resource location ("URL") into user device associated with the site. For example, user 102 may input a sports webpage's URL into user interface 112 and, in turn, user device 110 may access the website by communicating with the sports webpage's server across one or more networks 104.

Network(s) 104 may be a single network or a combination of different networks. For example, a network may be a local area network ("LAN"), a wide area network ("WAN"), a public network, a private network, a proprietary network, a Public Telephone Switched Network (PSTN), the Internet, a wireless network, a cellular network, a virtual network, or any combination thereof. A network may also include various network access points, (e.g., wired or wireless access points such as base stations or Internet exchange points) through which a data source may connect to the network(s) 104 in order to transmit information via network(s) 106, and a network node may connect to the network(s) 104 in order to receive information. In one embodiment, the network(s) 104 may correspond to an online advertising network or an ad network, which connects one or more devices, systems, servers, and/or databases/data stores, with one or more other systems, devices, servers, etc.

As illustrated, system 100 may include web services 120, which may allow a user to interact with a website hosted thereby. For example, web services 120 may host a platform with which user 102 may set up an online experiment. As another example, web services 120 may provide content to user device 110 via network(s) 104. Generally speaking, web services 120 may correspond to a suitable service provider/functionality capable of being interacted with by user 102 via user device 110 across network(s) 104.

In some embodiments, system 100 may include one or more databases, which may also be referred to as data stores herein. For instance, system 100 may include an experimentation metadata database 105, an analytics database 115, a historical database 125, and a dimension database 135. Although databases 105, 115, 125, and 135 are each separate in the illustrative embodiment, persons of ordinary skill in the art will recognize that two or more of databases 105, 115, 125, and 135 may be combined. Additionally, data associated with any of databases 105, 115, 125, and 135 may be distributed over one or more computing devices (e.g., server farms, database centers, and the like). In some embodiments, information stored by one or more of databases 105, 115, 125, and 135 may be accessed by user device 110, web services 120, and/or a data pipeline 130, as described in greater detail below, via network(s) 104.

Data pipeline 130, in one example embodiment, may be configured to validate data buckets for use in online experimentation. As described in greater detail herein, data pipeline 130 may include one or more components, and may be capable of communicating with one or more of databases 105, 115, 125, and 135, as well as web services 120 and user device 110 via network(s) 104. In one example, data pipeline 130 may perform offline hashing and hash value validation for online experiments (e.g., A/A validation). For instance, data pipeline 130 may be configured to perform offline hashing using historical data for a certain temporal range (e.g., one day, two days, one week, one month, etc.), rank hash values based on one or more metrics, and validate the hash values. Validated hash values may then be provided to web services 120, in one embodiment, for use in creation and execution of an online experiment.

Figure 2:
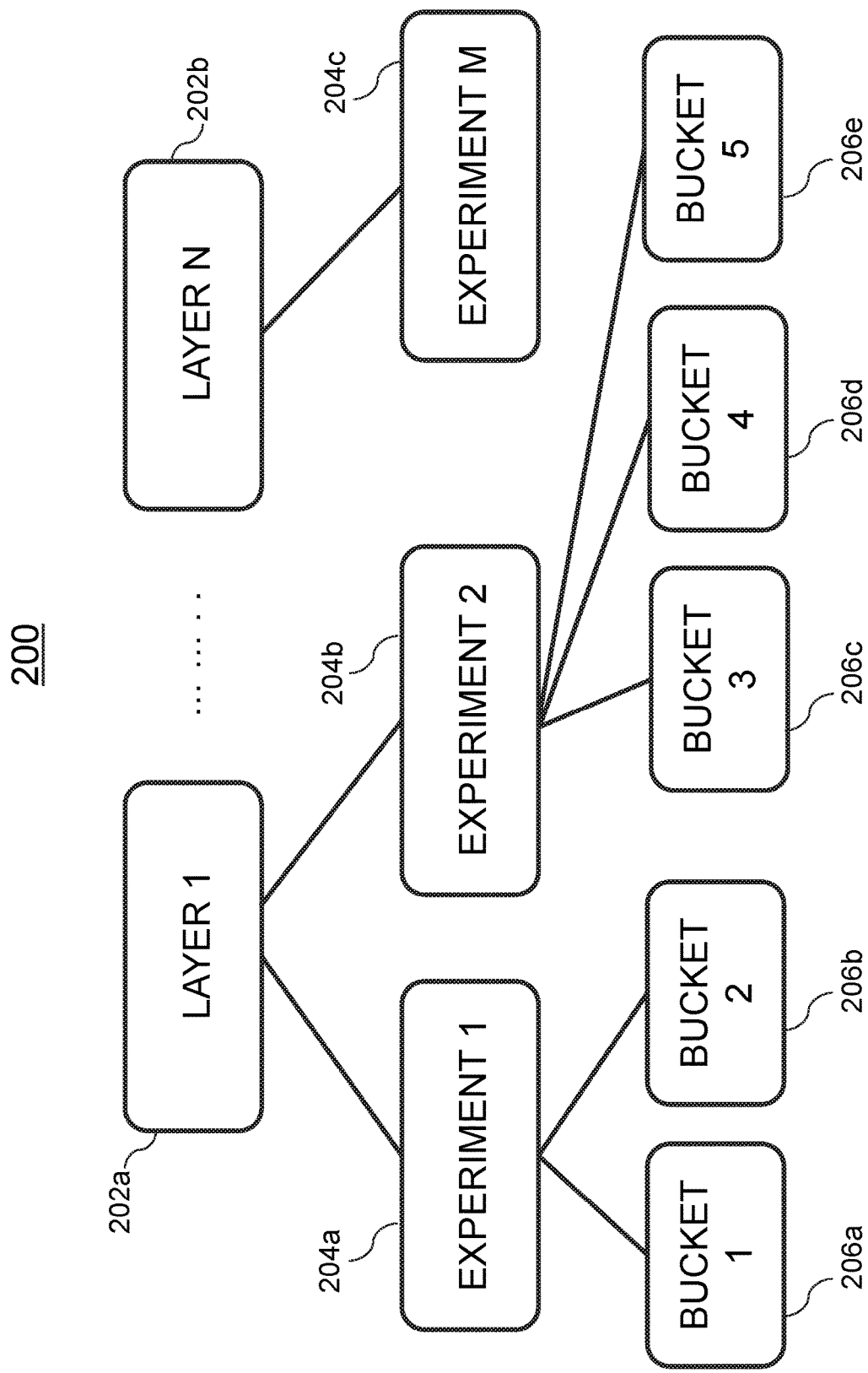
FIG. 2 is an illustrative diagram of an exemplary multi-layer experimental platform, in accordance with various embodiments of the present teachings.

FIG. 2 is an illustrative diagram of an exemplary multi-layer experimental platform, in accordance with various embodiments of the present teachings. Experimental platform 200, in the illustrative embodiment, corresponds to a multi-layer platform including two or more layers. For example, multi-layer experimental platform 200 may include a first layer 202a (e.g., Layer 1), and a second layer 202b (e.g., Layer N). In the illustrative embodiment, platform 200 may include N layers. Each layer may have one or more experiments existing thereon. For example, first layer 202a (e.g., Layer 1) may include a first experiment 204a (e.g., Experiment 1) and a second experiment 204b (e.g., Experiment 2). Second layer 202b (e.g., Layer N) may include a single experiment 204c (e.g., Experiment M). Furthermore, each experiment may include one or more data buckets, with which a user will be assigned to. As seen in the illustrative embodiment, first experiment 204a (e.g., Experiment 1) may include a first data bucket 206a (e.g., Bucket 1) and a second bucket 206b (e.g., Bucket 2). For example, first data bucket 206a (e.g., Bucket 1) may correspond to a control bucket, whereas second bucket 206b (e.g., Bucket 2) may correspond to an experimental bucket. Further still, as seen in the illustrative embodiment, second experiment 204b (e.g., Experiment 2) may include a first data bucket 206c (e.g., Bucket 3), a second data bucket 206d (e.g., Bucket 4), and a third data bucket 206e (e.g., Bucket 5). For example, data bucket 206c may correspond to a control bucket, and each of data buckets 206d and 206e may correspond to an experimental bucket, where each of data buckets 206d and 206e may provide a different experimental variant to be tested.

In some embodiments, an experiment may use an identifier associated with each user as the experimental unit, where the experimental unit corresponds to the item to be randomized into a data bucket. As an illustrative example, an identifier that may be used is a browser cookie associated with each user device 110 that accesses web services 120 and/or data pipeline 130, however persons of ordinary skill in the art will recognize that additional types of identifiers may be employed, and the use of browser cookies is merely exemplary. The various user identifiers (e.g., browser cookies), may be grouped into data buckets, where user devices 110 of a particular data bucket are provided with a same user experience, as described below with reference to FIGS. 3A and 3B.

Web services and the data pipeline, in some embodiments, correspond to components of the experimentation platform. The data pipeline may be configured to process data produced by the experiments and store that information in the data store. This enables the other components of the experiment system to access information. Web services may correspond to a hosted service which a layer between the UI component data component. The web server serves a web page that receives user requests and/or processes a request to enable a component to run. Experiments may be created via a web page user interface, which may be served by web services. Experiments that may be set up through a webpage user interface may be backed by a web service and saved in a database offline. The data buckets (experiment metadata) may then be provided to the user while browsing apps and/or webpages by another web service at run time. Thus, when an experiment is "running," this may correspond to the experiment being set up and data buckets being served to users.

Figure 3B:
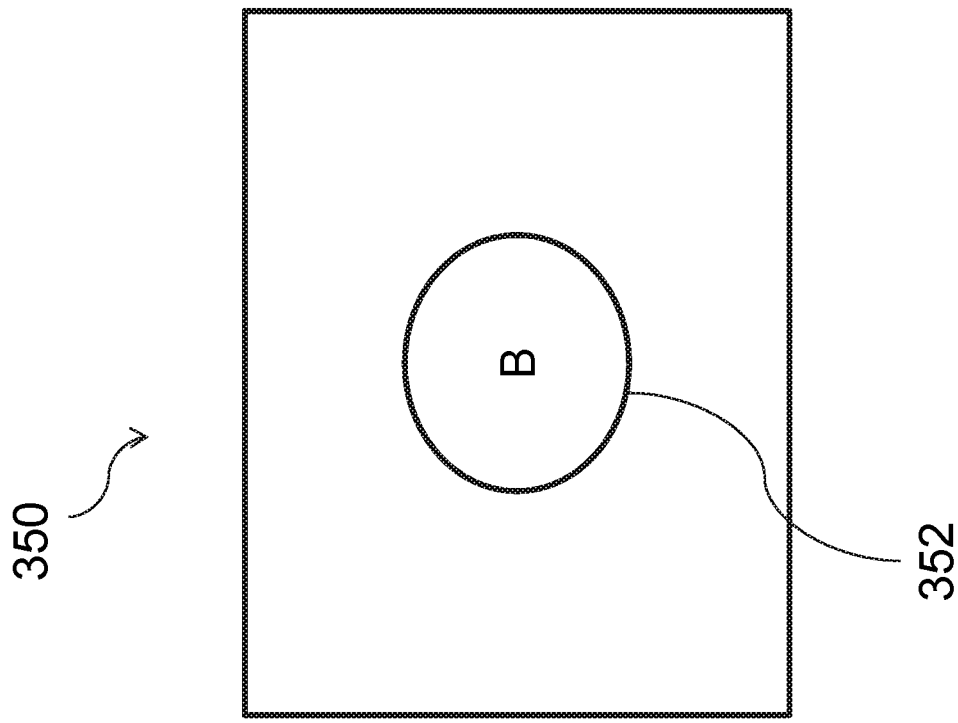
FIGS. 3A and 3B are illustrative diagrams of an exemplary control user experience and an exemplary experimental user experience, respectively, in accordance with various embodiments of the present teachings.
Figure 3A:
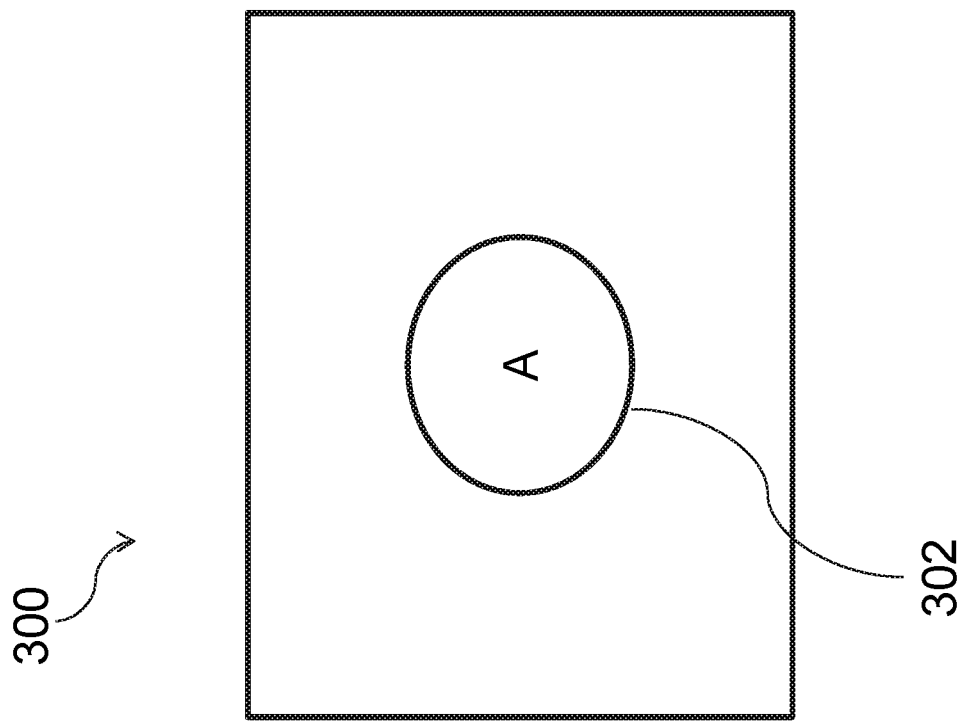

FIGS. 3A and 3B are illustrative diagrams of an exemplary control user experience and an exemplary experimental user experience, respectively, in accordance with various embodiments of the present teachings. User experience 300 of FIG. 3A, in one embodiment, may correspond to a control user experience. In this particular scenario, for example, a website may be configured to display a first button 302. However, an experiment designer may want to determine how receptive users would be to a change to the website where, instead of displaying first button 302, a different button, button 352, is displayed.

In order to determine the effectiveness of the new design (e.g., including button 352 as opposed to button 302), an experiment designer may create an experiment (e.g., experiment 204a) within a layer (e.g., layer 202a), which includes two data buckets (e.g., data buckets 206a and 206b). Users who access the website may be randomly placed into one of the two data buckets. Depending on which data bucket they are assigned to, one of user experience 300, including button 302, or user experience 350 of FIG. 3B, including button 352, may be provided to a corresponding user. If positive feedback is obtained regarding user experience 350, the experiment designer may modify his/her website such that instead of providing all users with user experience 300, all users are provided with user experience 350. Conversely, if the feedback received is poor regarding user experience 350, then user experience 300 may be retained.

Returning to FIG. 2, as described above, each user associated with a user identifier that is placed in one of an experiment's data buckets is provided with a same user experience. For instance, all of the users whose user identifiers are placed in a control data bucket may be provided with user experience 300, whereas all of the users whose user identifiers are placed in an experimental data bucket may be provided with user experience 350.

In some embodiments, each user identifier may be hashed (e.g., assigned and/or attributed) with an integer value within a pre-determined integer value range. For example, browser cookies for various user devices 110 may be hashed to an integer in the range of 0 to 999 (e.g., [0, 999]). Each data bucket of an experiment is assigned a range of these hash values, where a length of the range is associated with a desired size of that data bucket. In one embodiment, data buckets are sized in increments of 0.1% of total traffic volume for a particular website, however this is merely exemplary. As an illustrative example, a front webpage for a site may have, on average, daily traffic of 30 million users accessing the site. In this particular example, each hash value would correspond to 30,000 users. So, if the experiment designer wants to create a data bucket having a size of 5% of daily traffic, then 50 hash values would be allocated for that bucket.

Each experiment, as mentioned above, includes one or more data buckets. In one embodiment, each experiment may include two or more data buckets. For instance, each experiment may include one control data bucket and one or more test, or experimental, data buckets. All of the test data buckets may be compared with the control data bucket to test a particular feature associated with that test data bucket. For example, user experience 300 of FIG. 3A may be associated with a control data bucket, and user experience 350 of FIG. 3B may be associated with a test data bucket. User activity data associated with the user identifiers of the control data bucket may be analyzed and compared with the user activity data associated with the user identifiers of the test data bucket. If, for example, one or more additional user experiences are to be tested, then another test data bucket is created, and user activity associated with user identifiers that are provided with the additional user experience of that test data bucket may also be analyzed and compared with the user activity data associated with the user identifiers of the control data bucket.

In one embodiment, each experiment, and therefore the data buckets associated therewith, exists on a single layer of platform 200. Each layer covers an entire range of integer values (e.g., [0, 999]), and thus data buckets and experiments on a same layer are mutually exclusive as every user identifier is deterministically hashed to a same single hash value. Thus, a total bucket size over all experiments may not exceed 100% of the total traffic volume. Each layer has a unique seed that it is assigned, which is different and random, and may be used by a hash function to hash each user identifier to a particular integer. Therefore, each layer of platform 200 includes all available traffic, however traffic may be split across layers, and each layer is orthogonal to one another. Each user identifier may only be placed into, at most, one data bucket/experiment on each layer, but may also be placed into multiple buckets/experiments on different layers.

Figure 4:
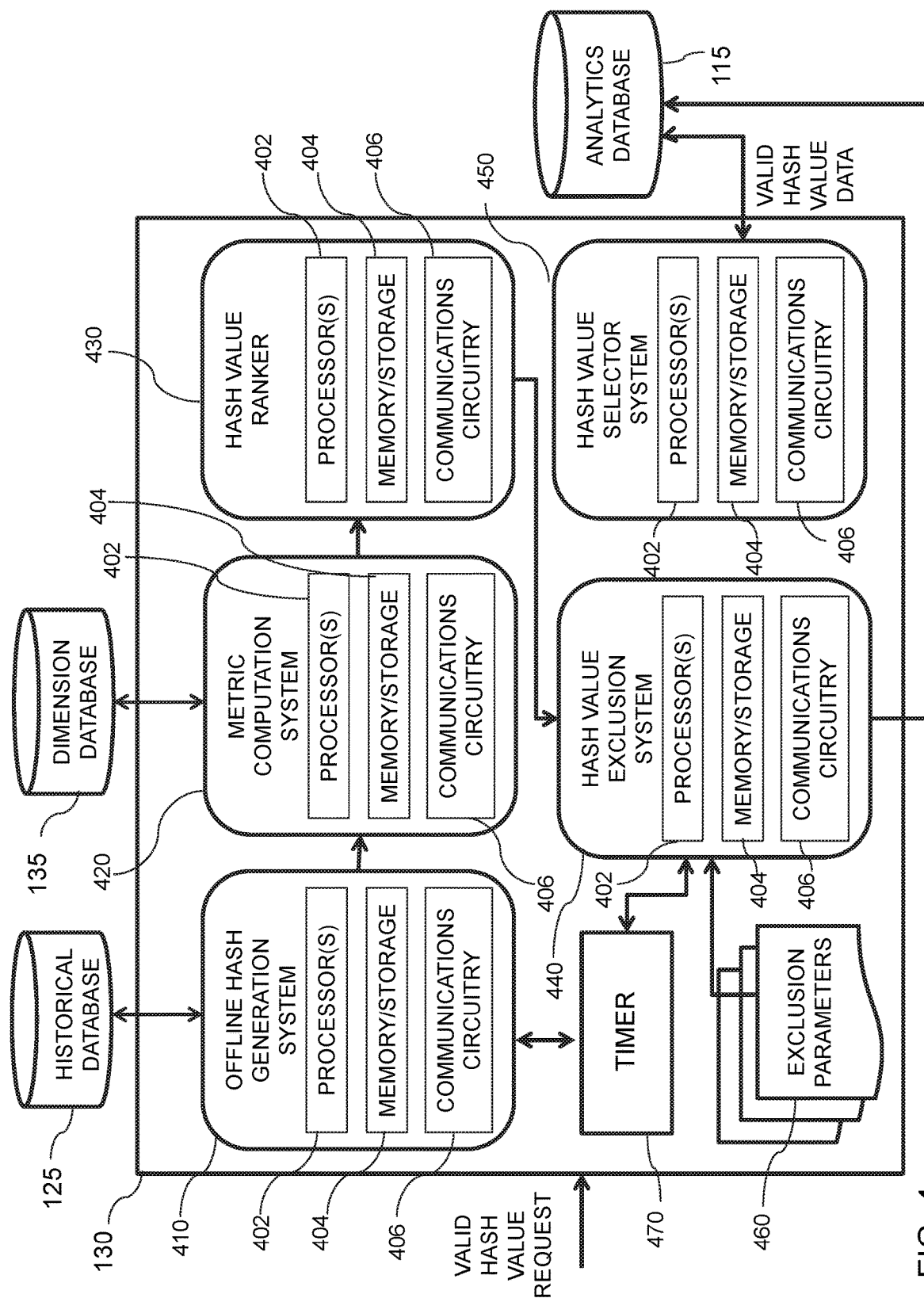
FIG. 4 is an illustrative diagram of an exemplary data pipeline system, in accordance with various embodiments of the present teachings.

FIG. 4 is an illustrative diagram of an exemplary data pipeline system, in accordance with various embodiments of the present teachings. Data pipeline system 130, in the non-limiting embodiment, includes an offline hash generation system 410, a metric computation system 420, a hash value ranker 430, a hash value exclusion system 440, and a hash value selector system 450. Each of offline hash generation system 410, metric computation system 420, hash value ranker 430, hash value exclusion system 440, and hash value selector system 450 may include one or more processor(s) 402, memory/storage 404, and communications circuitry 406, amongst other components.

Processor(s) 402 may include any suitable processing circuitry capable of controlling operations and functionality of one or more components/modules of data pipeline system 130, as well as facilitating communications between various components within data pipeline system 130 and/or with one or more other systems/components of system 100. In some embodiments, processor(s) 402 may include a central processing unit ("CPU"), a graphic processing unit ("GPU"), one or more microprocessors, a digital signal processor, or any other type of processor, or any combination thereof. In some embodiments, the functionality of processor(s) 402 may be performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, each of processor(s) 402 may include its own local memory, which may store program systems, program data, and/or one or more operating systems. However, processor(s) 402 may run an operating system ("OS") for one or more components of data pipeline system 130 (e.g., offline hash generation system 410, metric computation system 420, hash value ranker 430, hash value exclusion system 440, and hash value selector system 450), and/or one or more firmware applications, media applications, and/or applications resident thereon. In some embodiments, processor(s) 402 may run a local client script for reading and rendering content received from one or more websites. For example, processor(s) 402 may run a local JavaScript client for rendering HTML or XHTML content received from a particular URL.

Storage/memory 404 may include one or more types of storage mediums such as any volatile or non-volatile memory, or any removable or non-removable memory implemented in any suitable manner to store data for one or more of offline hash generation system 410, metric computation system 420, hash value ranker 430, hash value exclusion system 440, and/or hash value selector system 450. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, storage/memory 404 may be implemented as computer-readable storage media ("CRSM"), which may be any available physical media accessible by processor(s) 402 to execute one or more instructions stored within storage/memory 404. In some embodiments, one or more applications (e.g., gaming, music, video, calendars, lists, etc.) may be run by processor(s) 402, and may be stored in memory 404.

Communications circuitry 406 may include any circuitry allowing or enabling one or more components of data pipeline system 130 to communicate with one another, and/or with one or more additional devices, servers, and/or systems. For example, communications circuitry 406 may facilitate communications between two or more of offline hash generation system 410, metric computation system 420, hash value ranker 430, hash value exclusion system 440, and/or hash value selector system 450, or between one or more components of data pipeline system 130, or between one or more components of system 100. In some embodiments, communications between one or more components of system 100 may communicate with user devices 110 and/or data pipeline system 130 and/or web services 120 across network(s) 104 via communications circuitry 406. For example, network(s) 104 may be accessed using Transfer Control Protocol and Internet Protocol ("TCP/IP") (e.g., any of the protocols used in each of the TCP/IP layers), Hypertext Transfer Protocol ("HTTP"), WebRTC, SIP, and/or wireless application protocol ("WAP"). Various additional communication protocols may be used to facilitate communications between various components of data pipeline system 130 and/or to/from data pipeline system 130, including, but not limited to, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS 136/TDMA, iDen, LTE or any other suitable cellular network protocol), infrared, BitTorrent, FTP, RTP, RTSP, SSH, and/or VOIP.

Communications circuitry 406 may use any communications protocol, such as any of the previously mentioned exemplary communications protocols. In some embodiments, one or more components of data pipeline system 130 (e.g., offline hash generation system 410) may include one or more antennas to facilitate wireless communications with a network using various wireless technologies (e.g., Wi-Fi, Bluetooth, radiofrequency, etc.). In yet another embodiment, one or more components of user activity detection system may include one or more universal serial bus ("USB") ports, one or more Ethernet or broadband ports, and/or any other type of hardwire access port so that communications circuitry 406 facilitates communications with one or more communications networks.

Offline hash generation system 410, in an example embodiment, may be configured to performing hashing and metric computation using historical data stored by historical database 125. Offline hash generation system 410 may be capable of accessing data stored by historical database 125 via network(s) 104, however alternatively and/or additionally, offline hash generation system 410 may access data from historical database 125 directly without network(s) 104. In some embodiments, offline hash generation system 410 may be configured to obtain historical data, such as, and without limitation, user activity data associated with one or more webpages for one or more user identifiers, for various temporal intervals. For example, offline hash generation system 410 may be configured to obtain user activity data associated with user activities from a previous N days.

User activity data may be stored by historical database 125 with temporal metadata indicating a time/date with which the activity occurred. The user activity data may be obtained at predefined temporal intervals (e.g., every minute, every hour, every day, etc.), and/or upon a request being received by data pipeline system 130. For example, in response to receiving a valid hash value request, user activity may be accessed from historical database 125. Data pipeline system 130, in one embodiment, may include a timer 470, which offline hash generation system 410 may be operatively in communication with, to determine when to obtain user activity data from historical database 125. For instance, timer 470 may count various temporal intervals, and at each temporal interval, timer 470 may notify offline hash generation system 410 to obtain user activity data from historical database 125 representing user activity occurring within a particular amount of time prior to an expiration of that temporal interval. For example, every day, offline hash generation system 410 may access user activity data associated with a past seven days of user activity from historical database 125.

Metric computation system 420, in one embodiment, may be configured to compute values for one or more metrics based on the user activity data obtained from offline hash generation system 410. Metric computation system 420 may be in communication with dimension database 135. Dimensions database 135, in one embodiment, may store dimension information indicating metric computation parameters, techniques, and processes, such that metric computation system may perform the one or more metric computations. For example, metric computation system 420 may access dimension information from dimension database 135 across network(s) 135. As another example, metric computation system 420 may access dimension information from dimension database 135 directly.

As described in greater detail below with reference to FIGS. 6A and 6B, metric computation system 420 may be configured to compute one or more metrics for each user identifier from historical user activity data. Various types of metrics that may be computed on a user identifier basis may include, but are not limited to, a days visited metric, a page view (PV) metric, and a session-based metric. In some embodiments, a number of distinct identifiers may also be computed. The various types of user identifiers that may be used as a basis for the metric computation include, but are not limited to, browser cookie (e.g., b-cookie), IP address, device identifier, MAC address, telephone number, and the like. As an illustrative example, metric computation system 420 may obtain, for each browser cookie, activity data for user engagement parameters such as days visited, page view, sessions, as well as a distinct number of browser cookies from the user activity data. In one embodiment, however, dimension database 135 may store user engagement parameters, and thus metric computations for such user engagement parameters, which may be obtained by metric computation system 420.

Hash value ranker system 430, in one embodiment, may be configured to rank each hash value based on the one or more metrics that have been computed by metric computation system 420. For instance, hash value ranker system 430 may rank the user engagement parameters such as days visited, page view, sessions, and distinct identifiers, separately, to produce a ranked list of these hash values for each parameter. In some embodiments, for each hash value, a mean hash value for each user engagement parameter may be computed, and the mean hash value may be used for the ranking. The net result of hash value ranker system 430 may be one or more lists that indicate, for each hash value, a rank of that hash value for each user engagement parameter that has been computed. A more detailed explanation of hash value ranker system 430 may be seen below with reference to FIG. 7A.

Hash value exclusion system 440, in one embodiment, may determine an exclusion range for hash values from the ranked hash values obtained by hash value ranker system 430. In some embodiments, the hash value exclusion range may be based on one or more exclusion parameters 460. After obtaining the ranked hash value list, hash value exclusion system 440 may be configured to identify the exclusion range to be employed for a particular user activity range. In some embodiments, this determination may be based on temporal information obtained from timer 470. For instance, the exclusion range may vary depending on the historical range of data and/or the frequency of which that data is received. Additionally, in some embodiments, hash value exclusion system 440 may be configured to remove any hash values associated with one or more of the user engagement parameters falling within the exclusion range identified from exclusion range parameters 460. After the excluded hash values are removed from the hash value list, the remaining hash values, which may correspond to a homogenous hash value set, may be stored in analytics database 115. A more detailed explanation of hash value exclusion system 440 may be seen below with reference to FIG. 8A.

Hash value selector system 450, in one embodiment, may be configured to facilitate creation of an online experiment using validated hash values, such as those stored by analytics database 115. In some embodiments, in response to receiving a request to create an experiment, an experiment may be created within a layer of multi-layer experimentation platform 200. The request, for example, may be received by web services 120 from user interface 112 of user device 110. Hash value selector system 450 may be configured to determine a data bucket size for the experiment, as requested by the user, and fill each of the one or more data buckets with hash values from the homogenous hash value set stored by analytics database 115. Upon the data buckets being filled, hash value selector system 450 may provide a notification to web services 120, which relies the notification to user interface 112, indicating that the experiment is ready and may proceed. A more detailed explanation of hash value selector system 450 may be seen below with reference to FIG. 9A.

Figure 5:
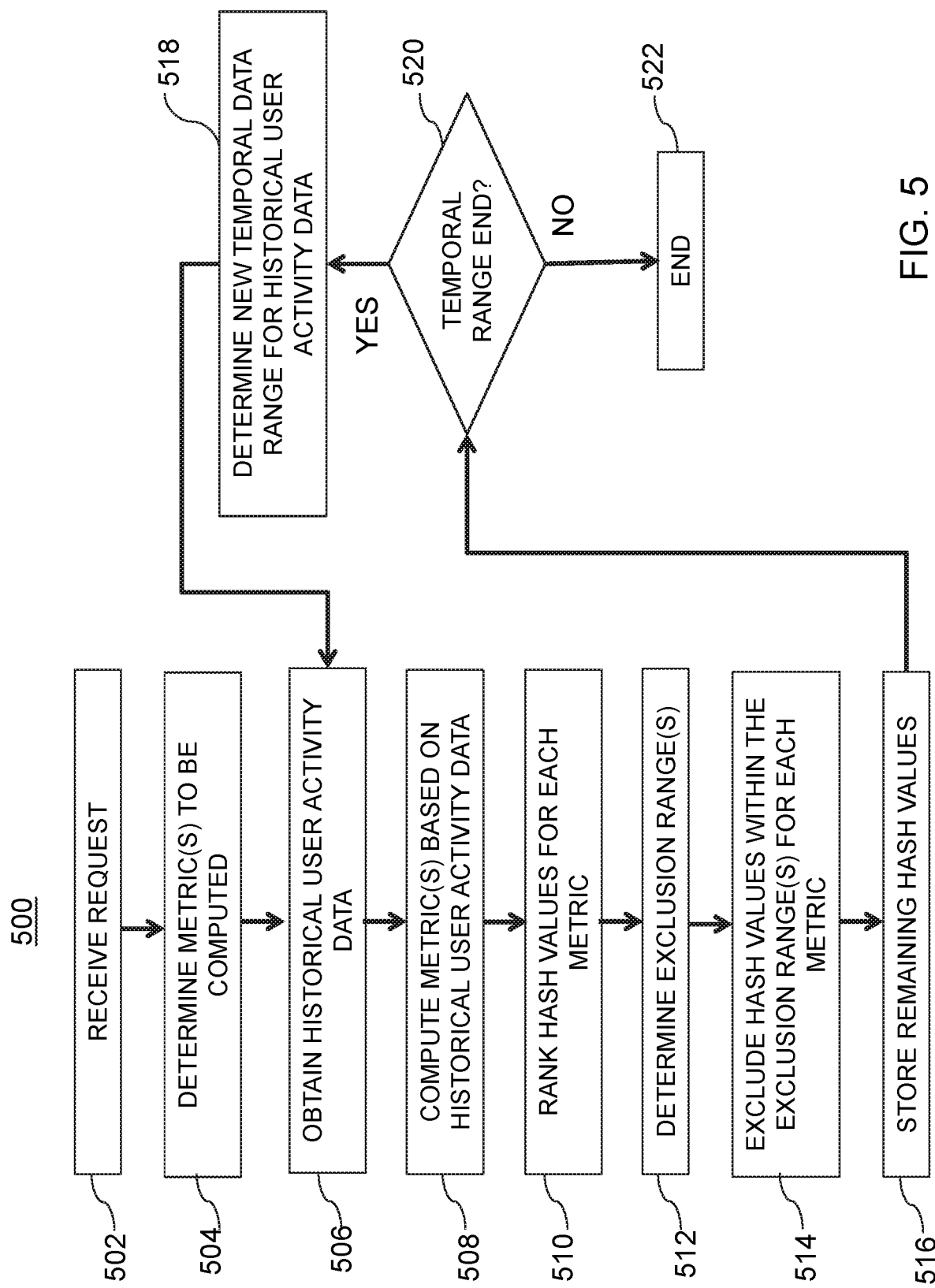
FIG. 5 is an illustrative flowchart of an exemplary processor for generating a homogenous value set of hash values, in accordance with various embodiments of the present teachings.

FIG. 5 is an illustrative flowchart of an exemplary processor for generating a homogenous value set of hash values, in accordance with various embodiments of the present teachings. Process 550, in a non-limiting embodiment, may begin at step 502. At step 502, a request may be received. For example, user 102 may submit a request via user interface 112 of user device 110 to web services 120 via network(s) 104. The request may be for an experiment to be created, to update a homogenous value set of hash values, or may be any other suitable type of request. In some embodiments, data pipeline system 130 may receive the request from web services 120 and/or user device 110 via network(s) 104.

At step 504, one or more metrics to be computed are determined. The one or more metrics may, in some embodiments, correspond to user engagement parameters. For example, days visited, page views, sessions, as well as a total number of distinct user identifiers, may all correspond to metrics to be determined.

At step 506, historical user activity data may be obtained. For instance, offline hash value generation system 410 may obtain historical user activity data from historical database 125. In some embodiments, the historical user activity data may correspond to user activity that occurred within a predetermined temporal range. For example, the obtained historical user activity data may represent user activity from a past seven days, however persons of ordinary skill in the art will recognize that the historical user activity data may represent user activity from any suitable previous amount of time, and the use of seven days is merely exemplary. In some embodiments, offline hash generation system 410 may determine what data to obtain from historical database 125 based on a current time, indicated from time 470.

At step 508, the one or more metrics may be computed based on the historical user activity data that was obtained. In this particular example, user engagement parameters of days visited, page views, and sessions may be computed as metrics based on each user identifier included within the historical user activity data. Furthermore, the number of distinct user identifiers included within the historical user activity data may also be determined.

At step 510, hash values for each metric may be ranked. After the metrics are computed for each user identifier (e.g., daily visits metric, page view metric, sessions based metric), in some embodiments, each user identifier may be hashed to an integer within a particular integer range. For example, there may be 1,000 integers in the integer range [0, 999] (e.g., 0 to 999). Each user identifier may then be assigned to one of those integers, and then the identifiers may be grouped for the particular integer values assigned thereto. As described in greater detail below, the hashing may be performed by a hash function that randomly assigns the user identifiers to a particular integer based on a unique seed. In some embodiments, a mean value for each of the user engagement parameters may be computed for each hash value (e.g., [0, 999]). In one embodiment, a data bucket size—or in other words a count of distinct identifiers—may also be computed for each hash value. The hash values may then be ranked for each metric.

At step 512, one or more exclusion ranges may be determined. In some embodiments, the exclusion range(s) may be determined based on one or more exclusion parameters 460. As an illustrative example, a top fifty and a bottom fifty hash values may correspond to one exemplary exclusion range. At step 514, hash values within the exclusion range(s) for each metric may be excluded from the list of hash values. For example, the hash values in the top 50 and the bottom 50 of the ranked list for the page view user engagement parameter may be removed. A similar process may also occur for the any additional user engagement parameters that are employed. As a result, a substantially homogenous hash value set may be obtained. At step 516, the remaining hash values (e.g., the homogenous hash value set) may be stored within analytics database 115.

At step 520, a determination may be made as to whether or not a temporal range has ended. For example, a determination may be made as to whether or not a new set of historical user activity data is needed. If not, then process 550 may proceed to step 522, where process 550 may end. However, in some embodiments, process 550 may continually loop at step 520 until it is determined that the temporal range has ended. If, at step 520, it is determined that the temporal range has ended, then process 550 may proceed to step 518, where a new temporal data range for historical user activity data is determined. For example, the historical user activity data may correspond to user activity occurring during a past seven days, and the historical user activity data may be updated every six hours. If a temporal difference between a time when the request is received, and a time when a determination as to whether the temporal range has ended is less than then a threshold amount of time (e.g., one minute, one hour, six hours, one day, etc.), then no new historical user activity data may be obtained. However, if the temporal difference is greater than the threshold amount of time, then process 550 may return to step 504 where new historical user activity data associated may be obtained. As an illustrative example, the threshold amount of time may be one day. If the previous historical data corresponded to June 1 to June 7, then after the threshold amount of time has elapsed, the new historical data may correspond to June 2 to June 8.

Figure 6A:
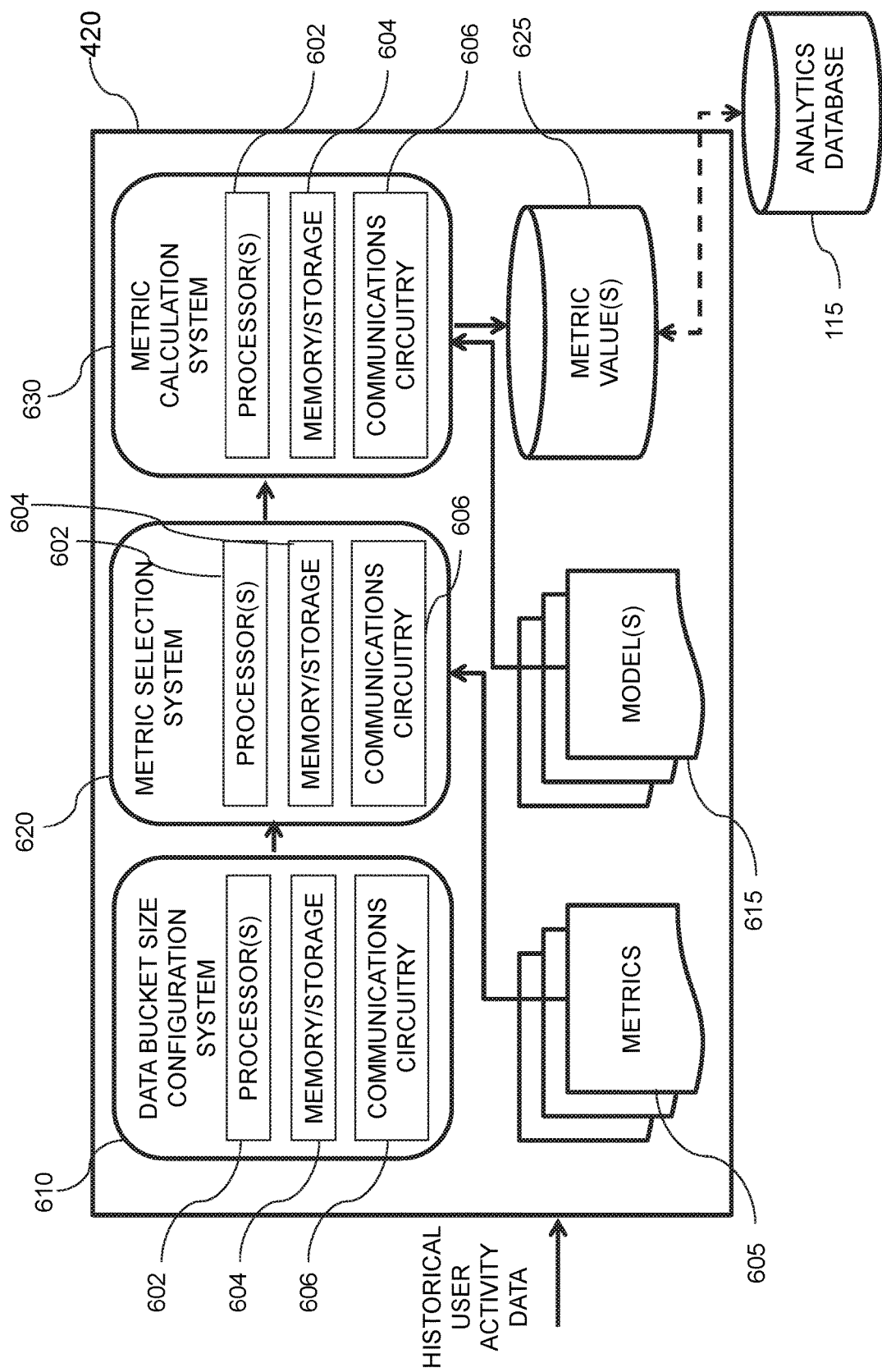
FIG. 6A is an illustrative diagram of an exemplary metric computation system, in accordance with various embodiments of the present teachings.

FIG. 6A is an illustrative diagram of an exemplary metric computation system, in accordance with various embodiments of the present teachings. Metric computation system 420, in the non-limiting, illustrative embodiment, may include a data bucket size configuration system 610, a metric selection system 620, and a metric calculation system 630. Each of data bucket size configuration system 610, metric selection system 620, and metric calculation system 630 may include one or more processors 602, memory/storage 604, and communications circuitry 606, amongst other components. In some embodiments, processor(s) 602, memory/storage 604, and communications circuitry 606 may be substantially similar to processor(s) 402, memory/storage 404, and communications circuitry 406 of FIG. 4, and the previous descriptions may apply.

Data bucket size configuration system 610 may, in one embodiment, be configured to receive historical user activity data from offline hash generation system 410 and/or historical database 125. Furthermore, data bucket size configuration system 610 may, in one embodiment, be configured to determine a size of a data bucket to be created for an online experiment based on a request for creating an experiment that was received by data pipeline 130. For example, if the request indicates that the data buckets to be created are 5% of the daily traffic, then data bucket size configuration system 610 may determine a total amount of daily traffic, and may determine a number of hash values to use to provide data buckets meeting the specifications of the request. Still further, in some embodiments, data bucket size configuration system 610 may be configured to determine a historical data range for user activity data to be obtained, or that has been obtained. For example, a determination may be made that seven days of user activity data may be needed, and data bucket size configuration system 610 may request that data from historical database 125 (and/or offline hash generation system 410).

Metric selection system 620 may be configured to determine and/or select, in one embodiment, the one or more metrics to be used for user engagement analysis and hash value selection. For instance, metric selection system 620 may select one or more metrics 605 to use for calculating user engagement associated with the historical user activity data. Metrics 605 may correspond to user engagement parameters that are computed. For example, the various types of user engagement parameters may include, but are not limited to, daily visits, page views, sessions, and the like. A metric for a particular user engagement determines a value for that user engagement parameter that may be selected by metric selection system 620 to be computed. Additionally, a metric associated with an amount of distinct user identifiers within the user activity data may also be determined. In some embodiments, certain metrics may be selected by metric selection system 620 as opposed to others based on a particular experiment, or based on a request from a user. Generally speaking, metrics for determining user engagement may be selected based on data integrity. For example, it may be determined that days visited, page view, and sessions user engagement parameters produce historically accurate metrics quantifying usage of a particular website and/or product in terms of visitation frequency and level of interaction. Persons of ordinary skill in the art will recognize that additional user engagement parameters may be employed for metrics 605 and/or substituted for one or more of the previously mentioned parameters, and the aforementioned is merely exemplary.

Metric calculation system 430, in one embodiment, may be configured to calculate the one or more metrics that have been selected based on the historical user activity data. In some embodiments, one or more models 615 may be employed by metric calculation system 630 to calculate/compute the one or more metrics. Model(s) 615, for instance, may describe formulations to be employed to compute each metric 605 that has been selected by metric selection system 620. For example, model(s) 615 may include a days visited model used for a days visited metric, a page view model for a page view metric, and a sessions model for a sessions based metric, however additional models may be used as well. In some embodiments, metric calculation system 430 may calculate metric values for each user identifier, where metric values correspond to the metrics for each user engagement parameter that have been computed analyzed. Upon completion, the metrics values for each user engagement parameter may be stored by metric value(s) database 625. In some embodiments, metric value(s) database 625 may be in communication with analytics database 115 such that, upon computation of the various metric values, the metric values may be stored additionally, or alternatively, by analytics database 115. In some embodiments, metric value(s) database 625 may serve as a temporary storage for the various metric values computed, however this is merely exemplary.

Figure 6B:
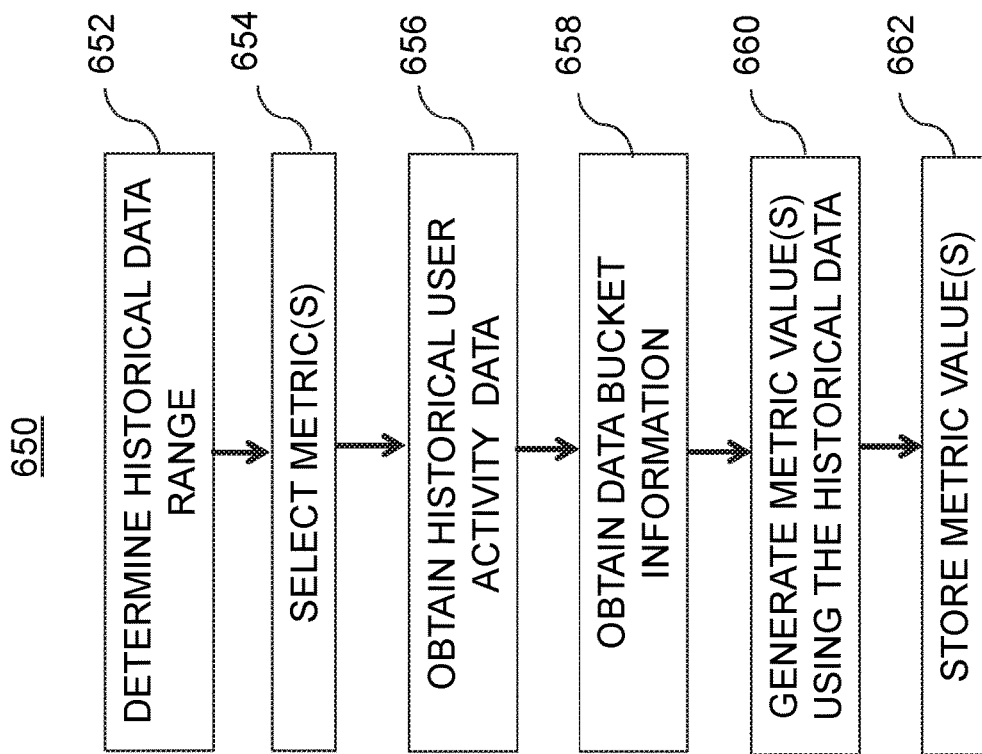
FIG. 6B is an illustrative flowchart of an exemplary processor for generating and storing one or more metric values, in accordance with various embodiments of the present teachings.

FIG. 6B is an illustrative flowchart of an exemplary processor for generating and storing one or more metric values, in accordance with various embodiments of the present teachings. Process 650, in a non-limiting embodiment, may begin at step 652. At step 652, a historical data range may be determined. For instance, an amount of time with which user activity data is to be obtained may be determined. As an illustrative example, user activity data representing user activity occurring over a past seven days may be desired. Therefore the historical data range, in this particular scenario, would correspond to seven days.

At step 654, one or metrics to be computed are selected. For example, metric selection system 620 may select one or more metrics 605 to be used for determining/quantifying user engagement. In one example embodiment, days visited metrics, page view metrics, and sessions based metrics may be selected. Additionally, a distinct number of user identifiers (e.g., browser cookies, MAC addresses, device identifiers, etc.) may be determined.

At step 656, the historical user activity data may be obtained. In some embodiments, the historical user activity data may be obtained from historical database 125, which may store user activities occurring on a website for each user identifier whose corresponding user device 110 accessed the site. The historical user activity data may represent various user activities that occurred. For example, user activities, which may also be referred to as interactions, with content being rendered, such as images, text, video, hyperlinks, and the like, may include, but is not limited to clicks, dwelling, hovering on/over, tapping, swiping, scrolling, flicking, etc., the content. In the context of at least one embodiment, user activities related to the content may be observed and used to explore, calculate, determined, and/or enhance the effectiveness of the content and the user experience.

At step 658, data bucket information may be obtained. For instance, the data bucket information may indicate a desired data bucket size. The data bucket size, for instance, may reflect the distinct number of user identifiers associated with the historical user activity data.

At step 660, one or more metric values, corresponding to the one or more metrics selected to be computed, may be generated using the historical data. For example, a metric value or values for the days visited metric may be generated using the historical user activity data. At step 662, the metric value(s) may be stored within metric value(s) database 625. In some embodiments, the metric value(s) may be additionally and/or alternatively stored within analytics database 115.

Figure 7A:
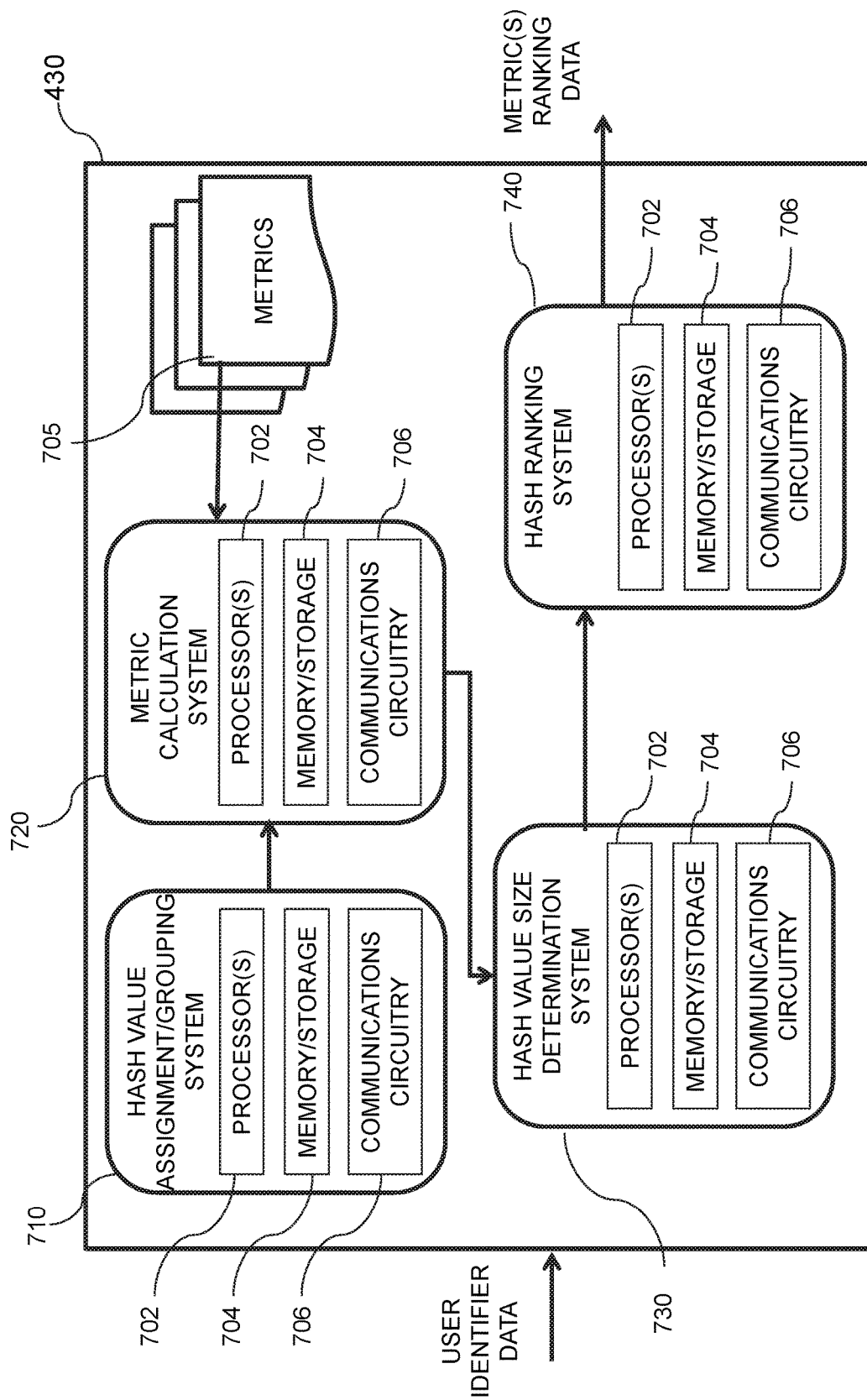
FIG. 7A is an illustrative diagram of an exemplary hash value ranker system, in accordance with various embodiments of the present teachings.

FIG. 7A is an illustrative diagram of an exemplary hash value ranker system, in accordance with various embodiments of the present teachings. Hash value ranker system 430, in the illustrative, non-limiting embodiment, may include a hash value assignment/grouping system 710, a metric calculation system 720, a hash value size determination system 730, and a hash ranking system 740. Each of hash value assignment/grouping system 710, metric calculation system 720, hash value size determination system 730, and hash ranking system 740 may include one or more processors 702, memory/storage 704, and communications circuitry 706. Processor(s) 702, memory/storage 704, and communications circuitry 706, in one embodiment, may be substantially similar to processor(s) 402, memory/storage 404, and communications circuitry 406 of FIG. 4, and the previous description may apply.

Hash value assignment/grouping system 710, in one embodiment, may be configured to assign each identifier from the user activity data to an integer value (e.g., a hash value). For example, a range of integer values may be chosen, and each user identifier may be assigned to one of those integers. In some embodiments, the assignment of an identifier to a particular integer value, also referred to as a hash value, may be performed by a hash function. The hash function may be a randomizing function that randomly assigns each user identifier to one integer within the integer range using a unique seed. In one embodiment, each layer of a multi-layer experimentation platform may be associated with a unique seed for the hash function.

Hash value assignment/grouping system 710 may further be configured to generate grouping of user identifiers based on an integer value. For example, user identifiers assigned to a same integer may be grouped together. This may yield integer values including a number of user identifiers which have each been assigned thereto. Typically, the hash function employed distributes user identifiers uniformly across each hash value (e.g., 0, 1, 999), and the means of each metric representing a particular user engagement parameter are normally distributed by that hash value.

Metric calculation system 720, in one embodiment, may be configured to determine an average of each metric associated with a corresponding user engagement parameter for each hash value. For example, for each hash value including a grouping of user identifiers, an average (e.g., a mean) metric value for that user engagement parameter may be determined. In some embodiments, metrics 705 may be employed to calculate the metric values by metric calculation system 720. Metrics 705 may be substantially similar to metrics 605 of FIG. 6 and the previous description may apply. In some embodiments, metrics 705 may also include information for determining the means for each metric to be calculated by metric calculation system 720.

Hash value size determination system 730, in one embodiment, may be configured to determine a quantity of distinct user identifiers within each set of hash values of each user engagement parameter. For example, data bucket determination system 730 may determine a number of unique user identifiers within each grouping of hash values. The quantity of user identifiers for each grouping of hash values should be substantially similar across each hash value, however in some embodiments there may be slight variations. Generally speaking, a good hash function will provide a relatively homogenous distribution of user identifiers across each hash value.

Hash ranking system 740, in one embodiment, may be configured to determine a ranking of each set of values representing each of the user engagement parameters with which metrics were computed. For example, based on the mean hash values for each user engagement parameter, as well as the number of unique identifiers, a rank of the hash values for each user engagement parameter may be produced. The rank may list each user engagement parameter's top ranked hash value to its least ranked hash value.

Figure 7B:
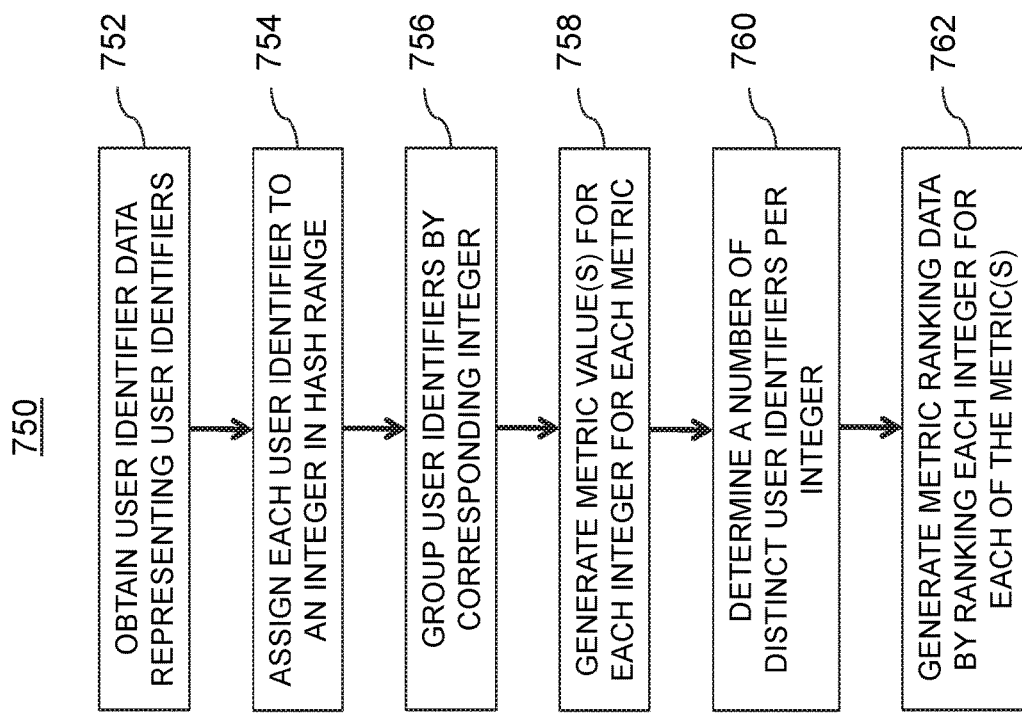
FIG. 7B is an illustrative flowchart of an exemplary processor for generating metric ranking data for one or more metrics, in accordance with various embodiments of the present teachings.

FIG. 7B is an illustrative flowchart of an exemplary processor for generating metric ranking data for one or more metrics, in accordance with various embodiments of the present teachings. Process 750 may, in a non-limiting embodiment, begin at step 752. At step 752, user identifier data representing user identifiers may be obtained. In some embodiments, the user identifier data may be included within user activity data. For example, the user activity data may represent user activity for each of a plurality of user identifiers. The user identifier data may include, in one embodiment, each user identifier that accessed the webpage/website with which the online experimentation is to be associated with. For example, the user identifier data may represent a plurality of browser cookies, device identifiers, MAC address, and the like, that interact with particular content (e.g., a webpage).

At step 754, each user identifier of the user identifier data may be assigned to an integer in a hash range. For instance, the hash range may correspond to a set of hash values (e.g., integers). In one example, the hash range may include 1,000 integers ranging from 0 to 999 (e.g., [0, 999]). In one embodiment, hash value assignment/grouping system may be configured to apply a hash function to each user identifier to generate a plurality of values, where each user identifier is assigned to one value of the plurality of values. In some embodiments, assigning each user identifier to an integer may include attributing a metadata tag associated with a particular hash value to that identifier. For example, a metadata tag may be attributed to a first user identifier indicating that the first user identifier is associated with a first hash value.

At step 756, the user identifiers may be grouped together by a corresponding integer. Continuing the example above, hash value assignment/group system 710 may be configured to determine which user identifiers have been attributed with a same metadata tag, and may group those user identifiers together. Typically, the number of user identifiers within each grouping is fairly consistent, however this may depend on the hash function used to assign user identifiers to integer values (e.g., hash values).

At step 758, one or more metric values for each integer may be generated for each metric. In some embodiments, a metric value for each hash value may be generated for each user engagement parameter's associated metric. For example, if the user engagement parameters are associated with days visited, page views, and sessions, then the metrics would correspond to a days visited metric, a page views metric, and a sessions based metric. Thus, a metric value, or values, may be generated, for each of these metrics, for each of the hash values. As an illustrative example, a metric value associated with a page views metric for each hash value may be generated. In some embodiments, a mean value for each metric value may be determined. For example, a mean value for each user engagement metric may be computed for each hash value.

At step 760, a number of distinct user identifiers per integer may be determined. For example, the number of distinct user identifiers grouped into each integer value may be determined by hash value size determination system 730. In some embodiments, the number of distinct user identifiers grouped into each integer value (e.g., hash value) is consistent across the various hash values. However, persons of ordinary skill in the art will recognize that variations across the number of distinct user identifiers grouped into each integer value may also occur.

At step 762, metric ranking data may be generated by ranking each integer value for each of the metrics. For example, the various hash values may be ranked based on their computed metric value. In some embodiments, the ranking may be based on the mean metric value. Furthermore, in some embodiments, the ranking may be based on the various metric values computed as well as the number of distinct user identifiers within each of the integer values. The metric ranking data, therefore, may indicate which hash values have a greatest ranking for each selected metric, and which hash values have a lowest ranking for each selected metric. In one example embodiment, if there are 1,000 hash values, then rankings may rank each of those 1,000 hash values from the greatest metric value for a particular metric to the lowest metric value for that particular metric. More detail regarding the metric ranking may be seen from Table I, below.

TABLE 1

| Hash Value | Page View Rank | Sessions Rank | Days Visited Rank | Distinct Identifier Count Ranke |
|---|---|---|---|---|
| 0 | 623 | 426 | 83 | 289 |
| 1 | 135 | 33 | 836 | 526 |
| 2 | 827 | 234 | 931 | 583 |
| . | | | | |
| . | | | | |
| . | | | | |
| 457 | 389 | 457 | 320 | 971 |
| . | | | | |
| . | | | | |
| . | | | | |
| 998 | 19 | 209 | 347 | 836 |
| 999 | 95 | 883 | 346 | 467 |

Figure 8A:
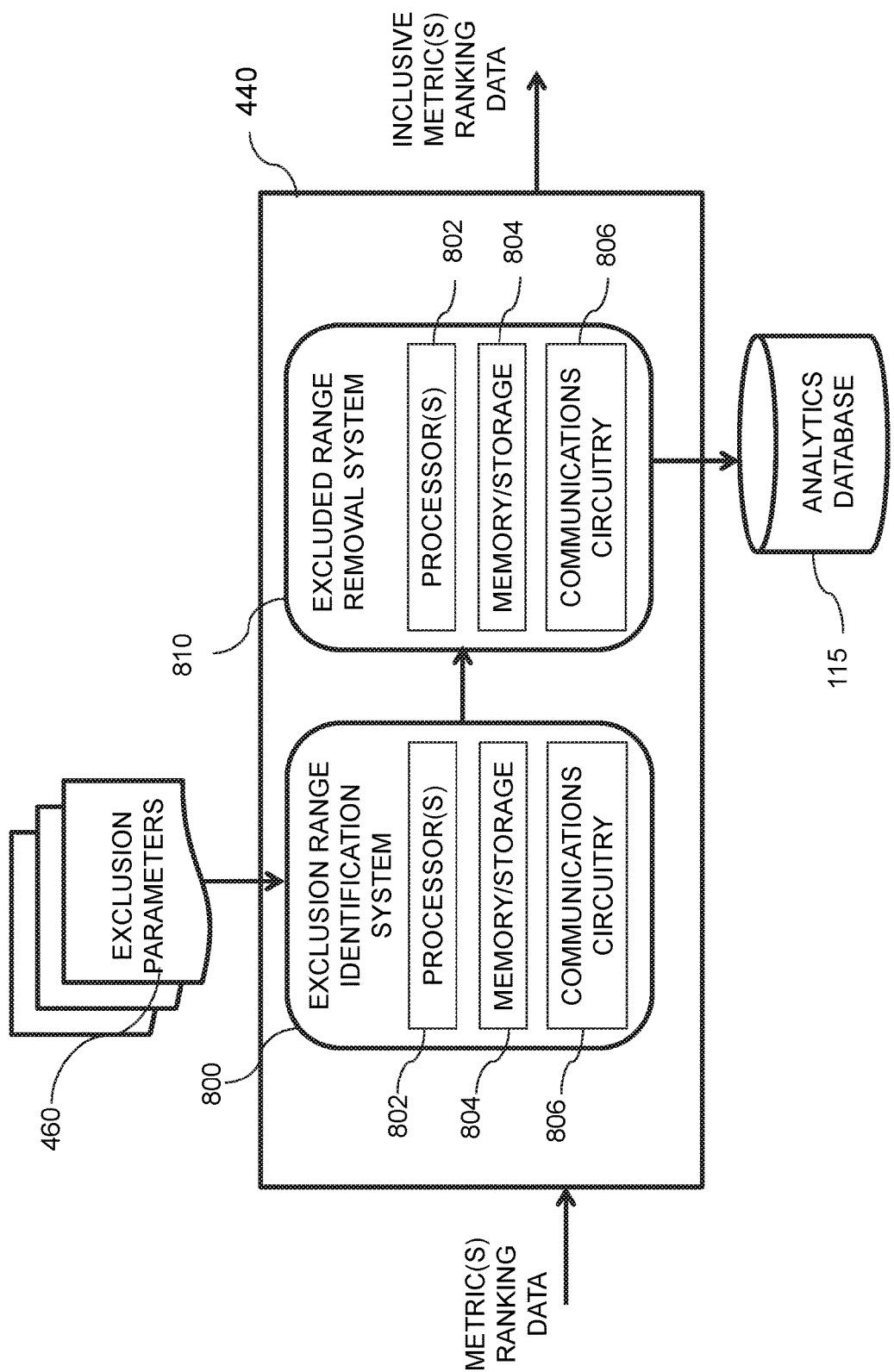
FIG. 8A is an illustrative diagram of an exemplary hash value exclusion system, in accordance with various embodiments of the present teachings.

FIG. 8A is an illustrative diagram of an exemplary hash value exclusion system, in accordance with various embodiments of the present teachings. Hash value exclusion system 440, in one non-limiting embodiment, may include an exclusion range identification system 800 and an exclude range removal system 810. Each of exclusion range identification system 800 and exclude range remove system 810 may include one or more processors 802, memory/storage 804, and communications circuitry 806, amongst other components. Processor(s) 802, memory/storage 804, and communications circuitry 806 may, in some embodiments, be substantially similar to processor(s) 402, memory/storage 404, and communications circuitry 406 of FIG. 4, and the previous description may apply.

Exclusion range identification system 800 may be configured, in some embodiments, to determine which hash value from each ranking of hash values fall within an exclusion range. The exclusion range may be selected from exclusion parameters 460, and may be based on a user preference, and experimental preference, or a default setting. As an illustrative example, the exclusion range may specify that hash values falling within the top 50 and bottom 50 are to be removed from consideration. However, persons of ordinary skill in the art will recognize that these values are merely exemplary. In some embodiments, the exclusion range may be symmetric (e.g., top X and bottom X hash values), whereas asymmetry between the top and bottom hash values may also be considered. Generally speaking, as the means of each of the user engagement metrics typically are distributed in a Gaussian distribution, the Central Limit Theorem would predict that an upper tail and a lower tail of the distribution would provide hash values that would traditionally fail A/A validation. Thus, restriction to a central part of the Normal distribution may occur.

Looking at Table 1, for hash value 1, may be identified as a removal candidate as the session's metric for hash value 1 has a ranking of 33 (e.g., if the exclusion range corresponds to the top 50 and bottom 50 hash values). Similarly, hash value 457 may also be removed as the distinct identifier count metric has a ranking of 971. Further still, hash value 998 may also be a candidate for removal as the page view metric ranking for hash value 998 is 19.

Excluded range removal system 810, in some embodiments, may be configured to remove the hash values that have been determined to fall within the exclusion range. Thus, excluded range removal system 810 may be configured to generate a substantially homogenous value set by removing each of the number of values of the exclusion range from each ranked set, leaving the remaining hash value set (e.g., the homogenous hash value set) corresponding to user identifiers that are available to be placed in an experiment's data bucket. In some embodiments, excluded range removal system 810 may be configured to apply a metadata tag to each user identifier that falls within the exclusion range(s) such that the identifiers associated with those hash values are prevented from being selected for an experiment's data bucket. Alternatively, excluded range removal system 810 may be configured to apply a metadata tag to each user identifier that does not fall within the exclusion range(s) such that those identifiers may be used for selection into an experiment's data bucket. The remaining hash values may be stored by analytics database 115 for future use with an experiment.

As an illustrative example, looking at Table 1, a first metadata tag may be applied to user identifiers associated with hash value 0, hash value 2, and hash value 999, where the first metadata tag indicates that the corresponding user identifiers are available for use in an experiment. Continuing this example, a second metadata tag may be applied to user identifiers associated with hash value 1, hash value 457, and hash value 998, where the second metadata tag indicates that the corresponding user identifier is unavailable for us in the experiment.

Figure 8B:
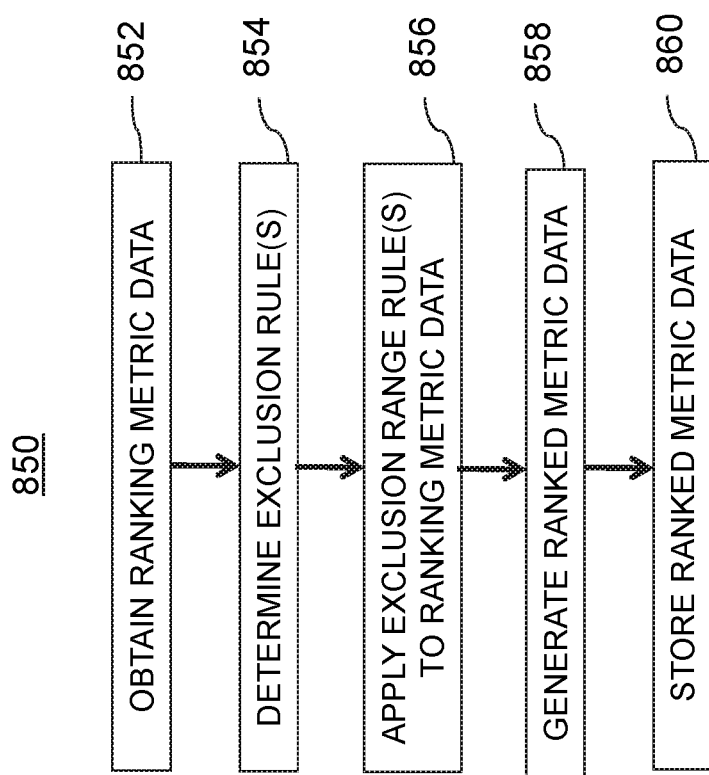
FIG. 8B is an illustrative flowchart of an exemplary processor for generating and storing ranked metric data, in accordance with various embodiments of the present teachings.

FIG. 8B is an illustrative flowchart of an exemplary processor for generating and storing ranked metric data, in accordance with various embodiments of the present teachings. Process 850, in a non-limiting embodiment, may begin at step 852. At step 852, ranking metric data may be obtained. For example, metric data representing the ranked list of user engagement parameters may be obtained from hash value ranker system 430. At step 854, one or more exclusion rules may be determined. For instance, exclusion rules 460 may be selected, indicating that hash values associated with a top X metric values are to be excluded, and a bottom Y metric values are to be excluded. In some embodiments, X and Y may be integers of equal value.

At step 856, exclusion range rules may be applied to the ranking metric data. For instance, if the exclusion range indicates that has values associated with the top X metric values are to be excluded (e.g., removed from consideration), then those hash values may be excluded. In some embodiments, hash values that are determined to be excluded may have a metadata tag applied thereto to indicate that those hash values are unavailable for placement in an experiment's data bucket. At step 858, ranked metric data may be generated. The ranked metric data may represent a homogenous value set including hash values that are available for use in an experiment (e.g., to be placed in an experiment's data bucket). At step 860, the ranked metric data may be stored. For instance, the ranked metric data representing the homogenous value set may be stored in analytics database 115. In some embodiments, the ranked metric data may include the excluded hash values, albeit those hash values may be flagged (e.g., metadata tag applied thereto) to indicate that the user identifiers associated with those hash values are unavailable and/or should not be used.

Figure 9A:
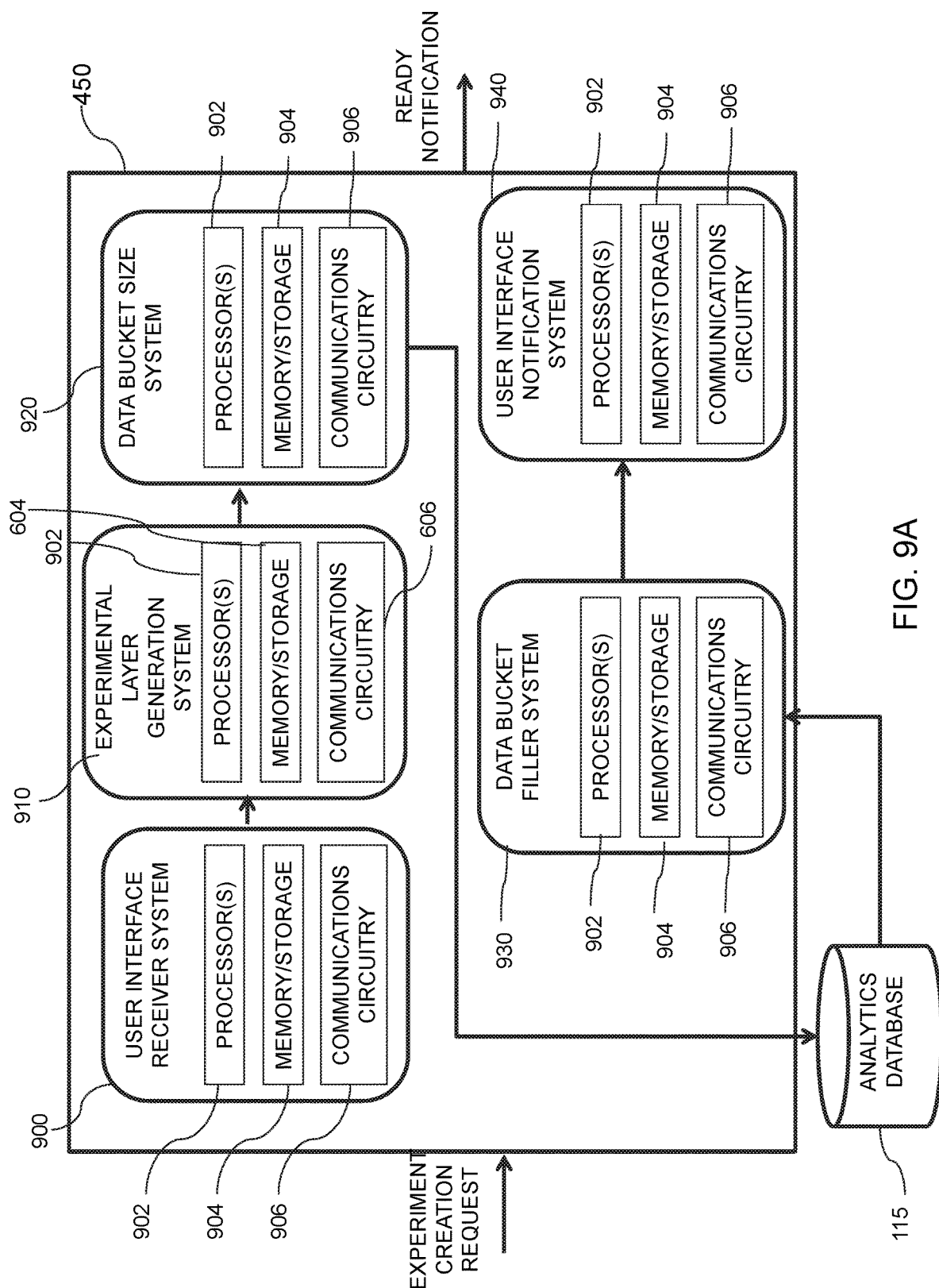
FIG. 9A is an illustrative diagram of an exemplary hash value selector system, in accordance with various embodiments of the present teachings.

FIG. 9A is an illustrative diagram of an exemplary hash value selector system, in accordance with various embodiments of the present teachings. Hash value selector system 450, in the illustrative embodiment, includes a user interface receiver system 900, an experiment layer generation system 910, a data bucket size system 920, a data bucket filler system 830, and a user interface notification system 940. Each of user interface receiver system 900, experiment layer generation system 910, data bucket size system 920, data bucket filler system 830, and user interface notification system 940 includes one or more processors 902, memory/storage 904, and communications circuitry 906, amongst other components. Processor(s) 902, memory/storage 904, and communications circuitry 906, in one embodiment, may be substantially similar to processor(s) 402, memory/storage 404, and communications circuitry 406 of FIG. 4, and the previous description may apply.

User interface receiver system 900 may, in one embodiment, be configured to receive a request to populate two or more data buckets for an online experiment. For instance, an experiment designer (e.g., user 102) may create, or seek to create, an online experiment (e.g., as described in greater detail above with reference to FIGS. 2, 3A, and 3B). The experiment designer may create two or more data buckets (e.g., a control data bucket and a test data bucket or buckets), and may desire for these data buckets to be populated by user identifiers with which the experiment will be conducted with. The request may be transmitted by user device 110 to web services 120 via network(s) 104. In turn, web services 120 may provide the request to data pipeline 130, and/or receive the request independently.

Experimental layer generation system 910 may be configured to generate an experiment within a layer of multi-layer experimentation platform 200, in some embodiments. For example, in response to receiving the request, a layer may be selected, and the experiment may be generated within that layer. In some embodiments, the experiment may encompass the entire layer, whereas in other embodiments, the experiment may only encompass a portion of that layer.

Data bucket size system 920 may be configured, in one embodiment, to determine a size of the data buckets to be used for the experiment being created. For example, the request from user 102 may indicate that a 5% data bucket is desired. Therefore, as data buckets may be sized in increments of 0.1% of total traffic volume for a particular website, if the site has, on average, daily traffic of 30 million users accessing the site, then each hash value would correspond to 30,000 users. So, if the experiment designer wants to create a data bucket having a size of 5% of daily traffic, then 50 hash values would be allocated for that bucket. In response to determining the size of the data buckets, data bucket size system 920 may provide data bucket size information to analytics database 115 for filling of the data buckets.

Data bucket filler system 930 may, in one embodiment, be configured to randomly select a plurality of user identifiers to be placed in one of the control data bucket or a test data bucket. Data bucket filler system 930 may receive user identifiers from a homogenous set of values stored by analytics database 115. As mentioned previously, the homogenous hash value set may previously be validated from A/A validation, and thus an experiment designer need not wait to perform A/A validation tests prior to conducting the experiment. Data bucket filler system 930 may further be configured to assign a metadata tag associated with a corresponding data bucket that each user identifier has been assigned to, to each user identifier. This metadata tag may persist throughout the experiment such that that user identifier is continually provided with the user experiences attributed to that data bucket with which it is assigned. In some embodiments, a random assignment function may be used to randomly assign each user identifier to one of the data buckets of the online experiment. Persons of ordinary skill in the art will recognize that any suitable random assignment function may be employed.

User interface notification system 940 may be configured, in one embodiment, to generate and send a notification to user device 110 indicating that the data buckets have been filled, and that the experiment may begin. For instance, visualization data representing a graphical user interface may be generated and sent to user device 110 for rendering by user interface 112. In some embodiments, the graphical user interface may indicate that the experiment is ready for use, as well as present analytics to be monitored for the experiment.

Figure 9B:
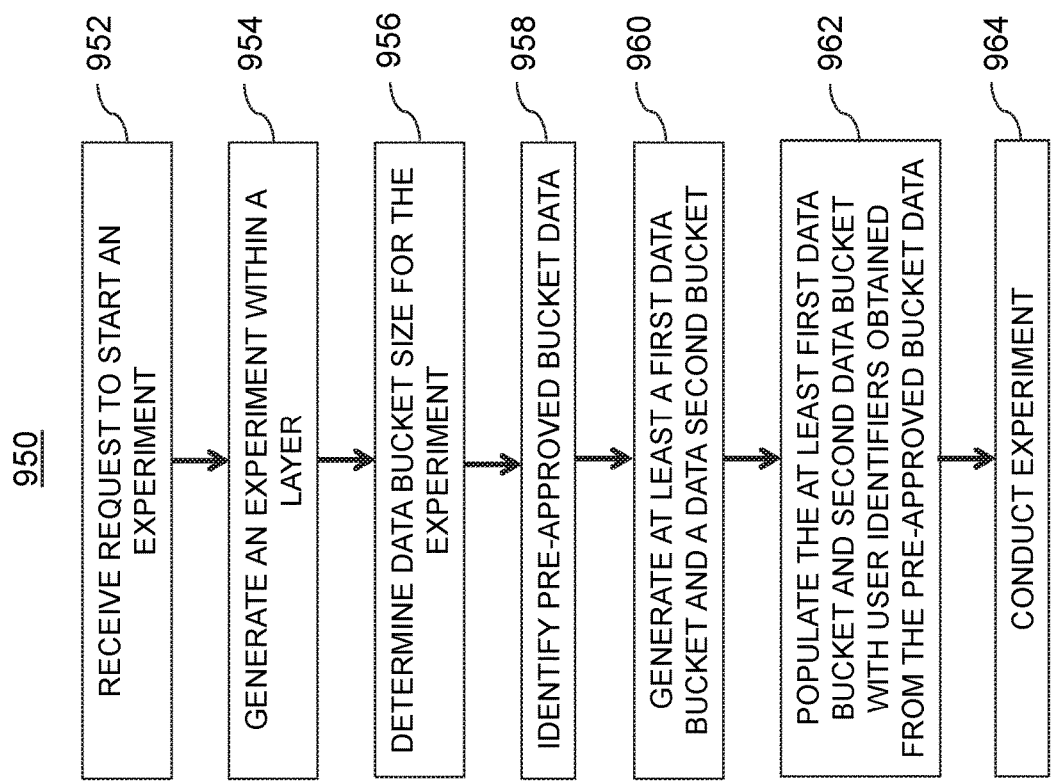
FIG. 9B is an illustrative flowchart of an exemplary processor for populating data buckets with user identifiers from pre-approved bucket data, in accordance with various embodiments of the present teachings.

FIG. 9B is an illustrative flowchart of an exemplary processor for populating data buckets with user identifiers from pre-approved bucket data, in accordance with various embodiments of the present teachings. Process 950, in one embodiment, may begin at step 952. At step 952, a request to start an experiment may be received. The request may indicate a data bucket size for the experiment, a name of the experiment, a number of data buckets needed for the experiment, and the like. At step 954, an experiment may be generated within a layer. For example, an experiment may be generated within a layer of multi-layer experimental platform 200. At step 956, a data bucket size for the experiment may be determined. In some embodiments, the data bucket size may be determined from the previously received request. However, alternatively, the data bucket size information may be obtained after the experiment has been generated.

At step 958, pre-approved bucket data may be identified. For example, the metric ranking data previously stored in analytics database 115 may be identified. The pre-approved bucket data may correspond to the metric ranking data representing a homogenous hash value set, which may include user identifiers that have been pre-approved for A/A validation. At step 960, at least a first data bucket and a second data bucket may be generated for the experiment. For example, at least a control data bucket and one test data bucket may be generated. The control data bucket may provide a control user experience to each user with whose user identifier is assigned thereto, whereas a test user experience may be provided to each user whose user identifier is assigned to a particular test data bucket. While it is possible to use a single data bucket within an experiment, the results may not provide an accurate estimation of the effects of the experiment as there may be no basis for comparison. Therefore, typically, experiments will employ one control data bucket and one or more test data buckets.

At step 962, the first data bucket and the second data bucket may be populated with user identifiers obtained from the pre-approved bucket data. The user identifiers may be randomly assigned to one of the first data bucket and the second data bucket. When a user identifier is assigned to a particular data bucket, a metadata tag is attributed to that data bucket such that the user experience associated with that data bucket is maintained for that particular user identifier. In some embodiments, the user identifier and metadata data pairing may be stored by analytics database 115 for continually monitoring of the user activity data of that particular user.

At step 964, the experiment may be conducted. For instance, the control user experience for the control data bucket may be provided to the corresponding users whose user identifiers are associated with the control data bucket. Further, the test user experience for the test data bucket may be provided to the corresponding users whose user identifiers are associated with the test data bucket.

Figure 10:
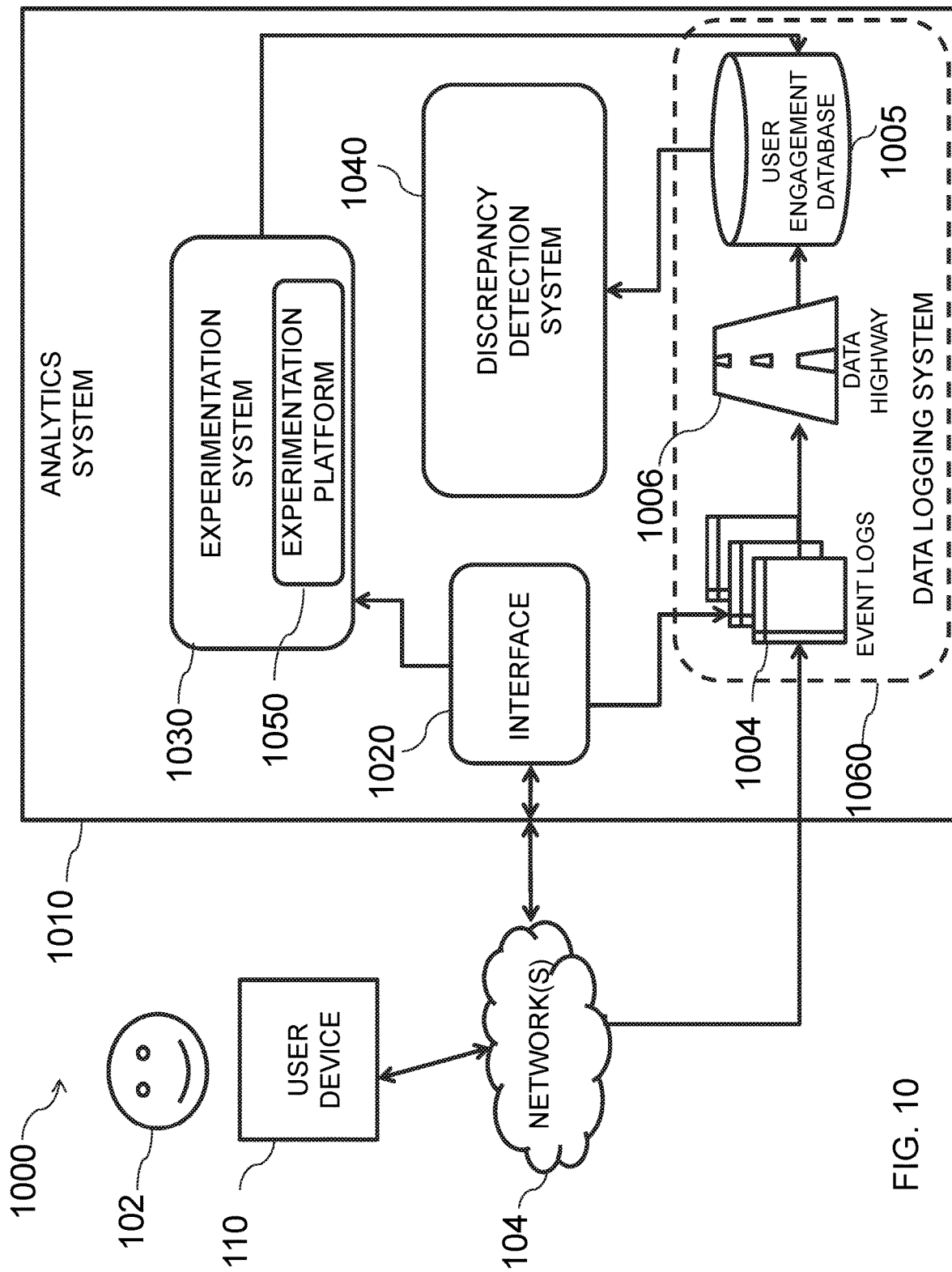
FIG. 10 is an illustrative diagram of a system for detecting data bucket discrepancies associated with online experiments, in accordance with various embodiments of the present teachings.

FIG. 10 is an illustrative diagram of a system for detecting data bucket discrepancies associated with online experiments, in accordance with various embodiments of the present teachings. System 1000, in the illustrative non-limiting embodiment, may include user device 110 operated by user 102, which may communicate with analytics system 1010 via network(s) 104. In some embodiments, content may be provided to user 102 on user device 110. For example, a user experience associated with an online experiment hosted by an experimentation system 1030 may be provided.

In some embodiments, user 102 may interact with the content associated with the user experience being provided for a particular online experiment. The interactions with the content may be detected by user device 110 and transmitted via network(s) 104 to analytics system 1010. In some embodiments, each interaction that occurs with the provided content may be logged within a data logging system 1060. For instance, event logs 1004 may store records of each user interaction that occurs. Event logs 1004 may be created by data highway 1006 which may correspond to a centralized event and log collection service. User engagement database 1005, in one embodiment, may store events and user activity data associated with discrepancy monitoring data buckets. In some embodiments, user activity data associated with discrepancy monitoring data buckets may be aggregated hourly, daily, weekly, etc., and which point the aggregated user activated data may also be stored by user engagement database 1005.

Analytics system 1010 may also include an interface 1020. Interface 1020 may be configured to receive user requests, and provide responses to those user requests. For example, if user experience 350 of FIG. 3B is provided to user device 110, and user 102 clicks on button 352, the indication that the click occurred may be received by user interface 1020. In response, user interface 1020 may be configured to receive, from experimentation system 1030, a predetermined response to the clicking of button 352. The response may in turn be communicated back to user device 110 for consumption by user 102.

Analytics system 1010 may further include an experimentation platform 1030, which may be in communication with interface 1020, as mentioned above. Experimentation system 1030 may be configured to host one or more online experiments to be provided to one or more users. In some embodiments, analytics system 1050 may facilitate operation of an experimentation platform 1050. For example, experimentation platform 1050 may correspond to a multi-layer experimental platform, such as multi-layer experimental platform 200 of FIG. 2. Experimentation system 1030 may further be in communication with user engagement database 1005 such that interactions associated with discrepancy monitoring may be stored thereby.

Analytics system 1040 may further include, in one embodiment, a discrepancy detection system 1040. Discrepancy detection system 1040 may be configured, in one embodiment, to determine a discrepancy between an expected amount of user identifiers and an actual amount of user identifiers. This discrepancy, or gap, may reflect a difference between an expected sample size of an experiment and the actual sample size of the experiment. Large discrepancies may lead to inaccurate experimentation results and poor user experience. Therefore, reducing/minimizing the discrepancy is of upmost importance. Further still, identifying experiments where discrepancy exists, and in particular where large discrepancy exists, is crucial.

Figure 11:
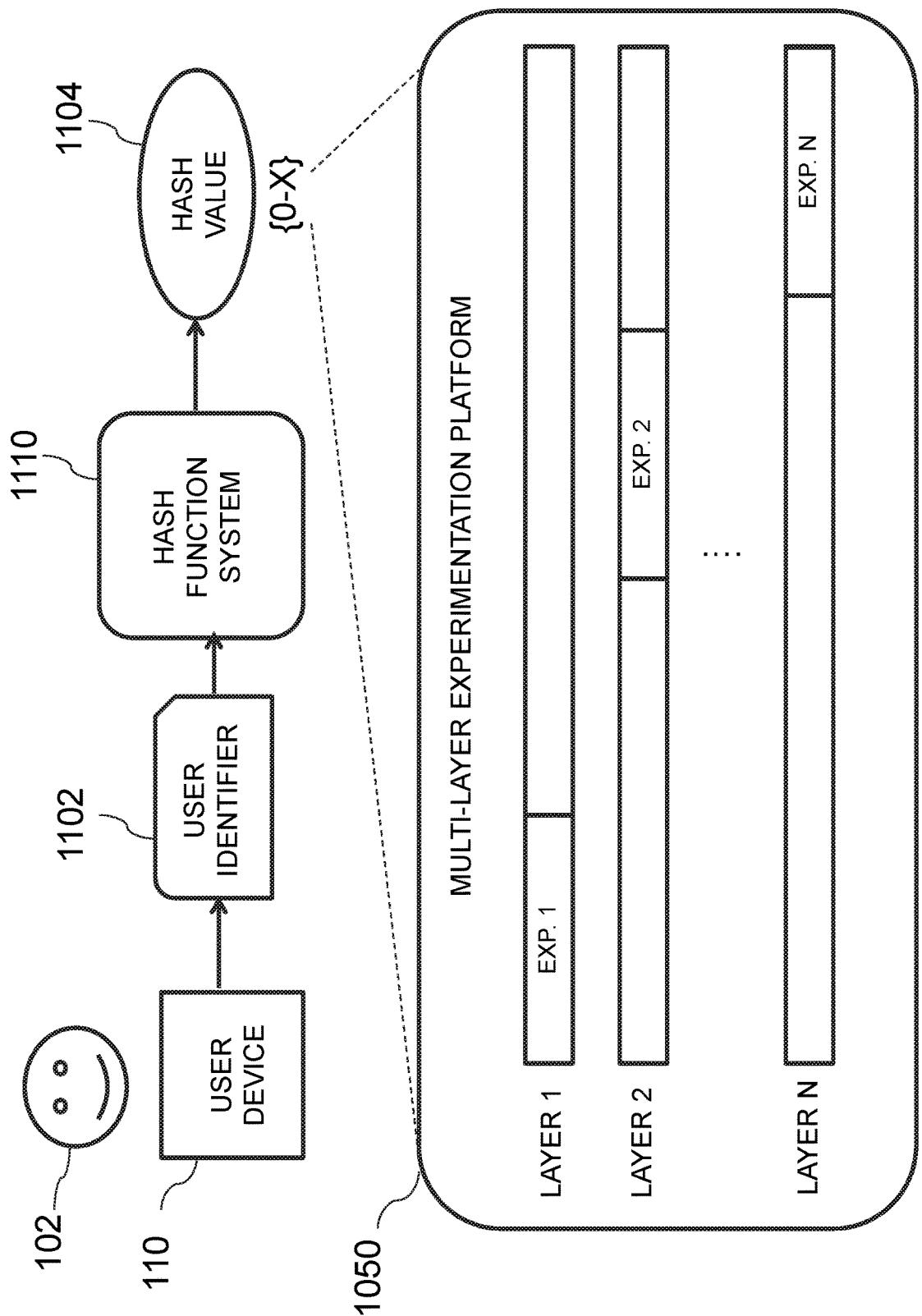
FIG. 11 is an illustrative diagram of a system for hashing a user device identifier into one or more layers of a multi-layer experimental platform, in accordance with various embodiments of the present teachings.

FIG. 11 is an illustrative diagram of a system for hashing a user device identifier into one or more layers of a multi-layer experimental platform, in accordance with various embodiments of the present teachings. FIG. 11 illustrates one embodiment of a multi-layered experimentation platform, such as that described by FIG. 2. Each user 102 may be associated with a corresponding user device 110, and each user device may be associated with a particular user identifier 1102. Various types of user identifiers 1102 may include, but are not limited to, browser cookies, device identifiers, MAC identifiers, IP addresses, telephone numbers, and the like. Each user identifier 1102 may be provided to a hash function system 1110, which may be configured to hash the user identifier to a particular hash value 1104. Hash function system 1110 may, for example include a hash function that randomly assigns each user identifier to a hash value 1104.

In some embodiments, each layer of the multi-layer experimentation platform 1050 may include a unique seed for the hash function. In some embodiments, hash values 1104 may encompass integer values within the range of 0 to 999 (e.g., [0, 999]), however persons of ordinary skill in the art will recognize that this is merely exemplary. Each layer of multi-layer experimentation platform 1050 may be orthogonal to the other layers, such that the same hash function of hash function system 1110 may be used for each layer with a corresponding unique seed associated with that layer. Thus, a user identifier may be hashed into a same segment in a given layer, however that user may be hashed into a different segment in a different layer.

Figure 12A:
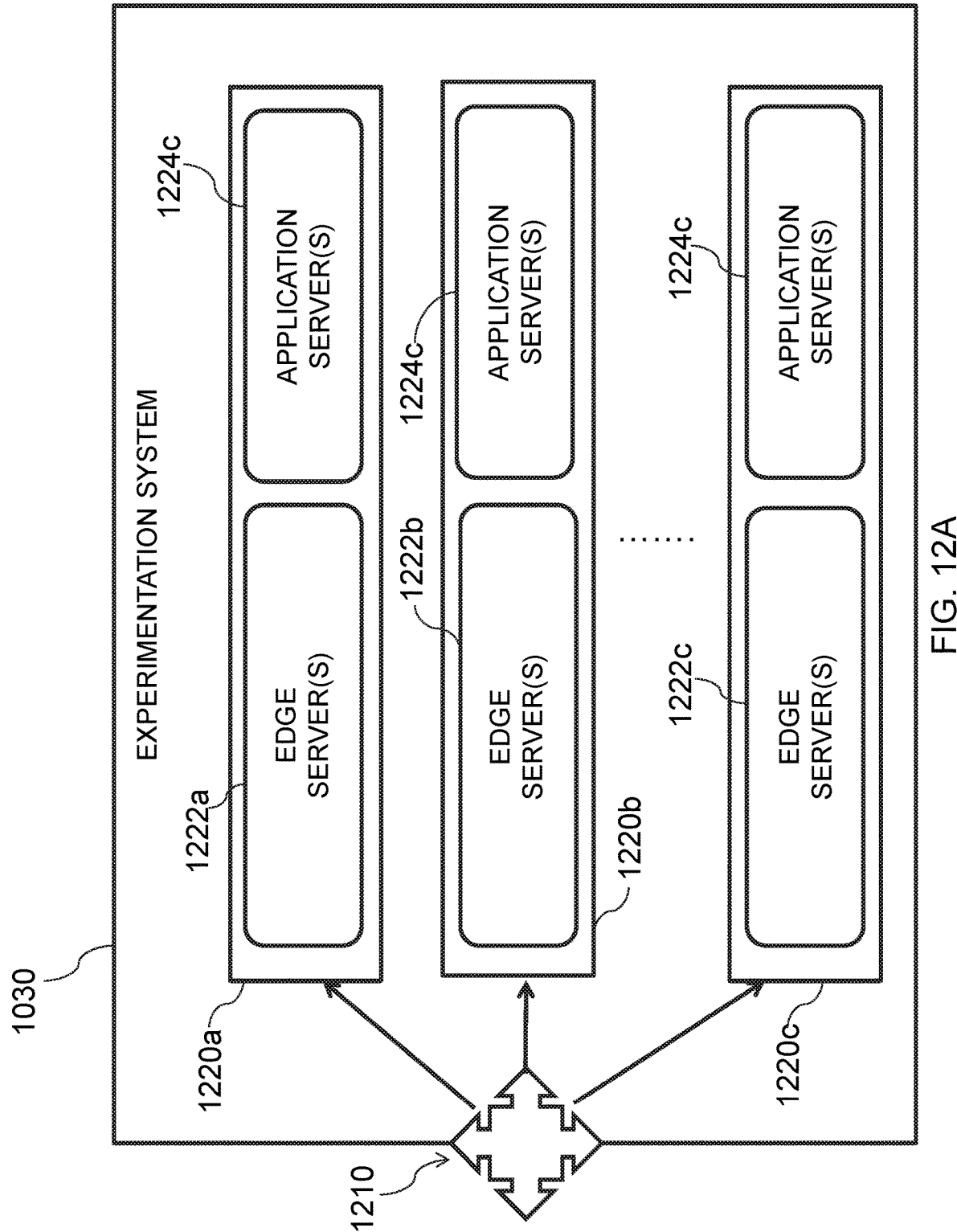
FIG. 12A is an illustrative diagram of an exemplary experimentation system, in accordance with various embodiments of the present teachings.

FIG. 12A is an illustrative diagram of an exemplary experimentation system, in accordance with various embodiments of the present teachings. In the non-limiting embodiment, experimentation system 1030 one or more locations 1220a, 1220b, and 1220c. When a request comes in to experimentation platform 1030, it is routed to a nearest location by a load-balancer 1210. Load-balancer 1210, in one embodiment, may be configured to distribute incoming requests to one or more locations 1220a-c based on that locations proximity to a user device that sent the request, bandwidth restrictions of network(s) 104, bandwidth settings of the various servers and processors of each of locations 1220a-c, and the like.

Each of locations 1220a-c includes, in one embodiment, one or more edge servers and one or more application servers. For instance, location 1220a may include edge server(s) 1222a and application server(s) 1224a, location 1220b may include edge server(s) 1222b and application server(s) 1224b, and location 1220c may include edge server(s) 122c and application server(s) 1224c. Each of edge servers 1222a-c, which may collectively referred to as edge server(s) 1222, may include one or more proxy servers configured to route requests received by that edge server to a corresponding location's application server(s). In some embodiments, the one or more proxy servers may include support for data traffic splitting as well as infrastructure for meta-data distribution. Edge server(s) 1222 may run sampling functions to randomize the user identifiers, for example. Application servers 1224a-c, which collectively may be referred to as application server(s) 1224, may process received requests routed thereto and may be configured to generate and send back a response with an appropriate user experience to an end user's requesting user device 110.

Figure 12B:
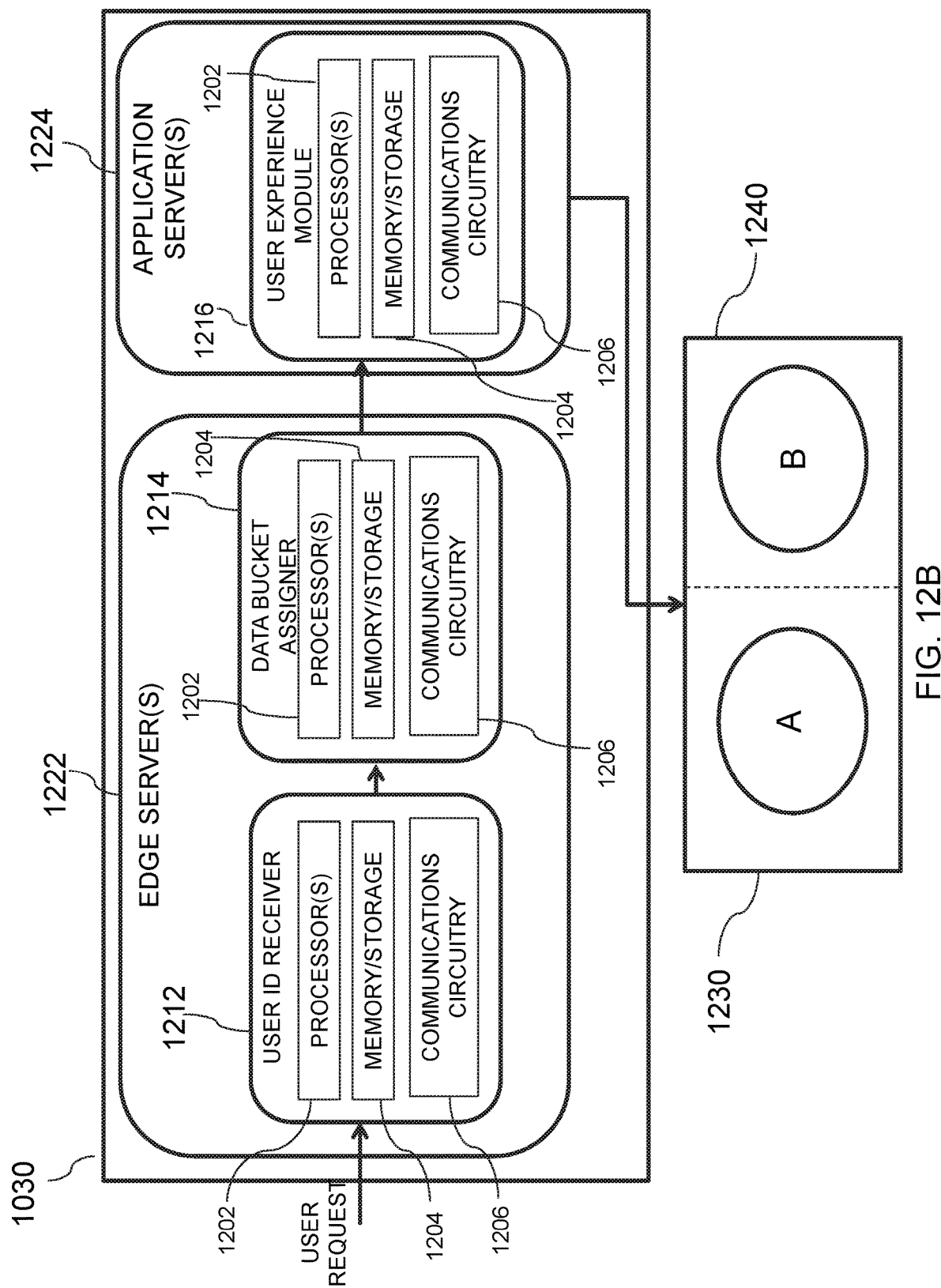
FIG. 12B is an illustrative diagram of the exemplary experimentation system of FIG. 12A capable of providing various user experiences, in accordance with various embodiments of the present teachings.

FIG. 12B is an illustrative diagram of the exemplary experimentation system of FIG. 12A capable of providing various user experiences, in accordance with various embodiments of the present teachings. As mentioned above, experimentation system 1030 may include one or more locations 1220, each of which may include one or more edge server(s) 1222 and one or more application server(s) 1224.

In some embodiments, edge server(s) 1222 may include a user identifier ("ID") receiver system 1212 and a data bucket assigner system 1214. Each of user ID receiver system 1212 and data bucker assigner system 1214 may include one or more processor(s) 1202, memory/storage 1204, and communications circuitry 1206. Each of processor(s) 1202, memory/storage 1204, and communications circuitry 1206 are, in some embodiments, substantially similar to processor(s) 402, memory/storage 404, and communications circuitry 406 of FIG. 4, and the previous description may apply.

User ID receiver system 1212 may, in some embodiments, be configured to receive incoming user requests received by experimentation platform 1030 and determine a user identifier associated with the user device with which the request is associated. For instance, requests received from user device 110 may be distributed to one of locations 1220a-c. Upon receipt at one of locations 1220a-c, a corresponding user ID receiver system 1212 of that location may determine a user ID associated with the user device that sent that the request. In some embodiments, the user identifier, or other characteristics used to identify the particular user that sent the request, may be determined using any suitable user identifier determination technique such as, and without limitation, user agent string analysis.

Data bucket assigner 1214 may be configured to determine a data bucket with which a user identifier that has been identified by user ID receiver system 1212 is to be assigned to. For example, data bucket assigner system 1214 may include a randomizer function that is configured to randomly assign a user identifier to a particular data bucket such that that user identifier's associated user device will receive a particular user experience. In one example embodiment, data bucket assigner system 1214 may input the user identifier into the randomizer function that will randomly pick a data bucket to assign that user identifier too. For example, the randomizer function may randomly assign the user identifier to one of a control data bucket or a test data bucket associated with a particular online experiment. In some embodiments, data bucket assigner system 1214 may determine that a user identifier associated with an incoming request is already associated with a particular data bucket. For example, the user identifier may have a metadata tag attributed thereto that indicates a data bucket that the user identifier has previously been assigned to.

Application server(s) 1224 may, in some embodiments, include one or more user experience modules 1216. User experience module(s) 1216 may be configured to receive the user identifier and corresponding data bucket assignment from data bucket assigner system 1214, and may retrieve an appropriate user experience to be rendered fro that user identifier. For example, user experience module 1216 may determine that a user identifier that is received is attributed with a control data bucket, and therefore is to be provided with a control user experience 1230. As another example, user experience module 1216 may determine that a user identifier that is received is attributed with a test data bucket, and therefore is to be provided with a test user experience 1240. In response, application server(s) 1224 may be configured to send data representing the appropriate user experience (e.g., one of control user experience 1230 and test user experience 1240) to the user device (e.g., user device 110) associated with the user identifier that the request is associated with.

Figure 13:
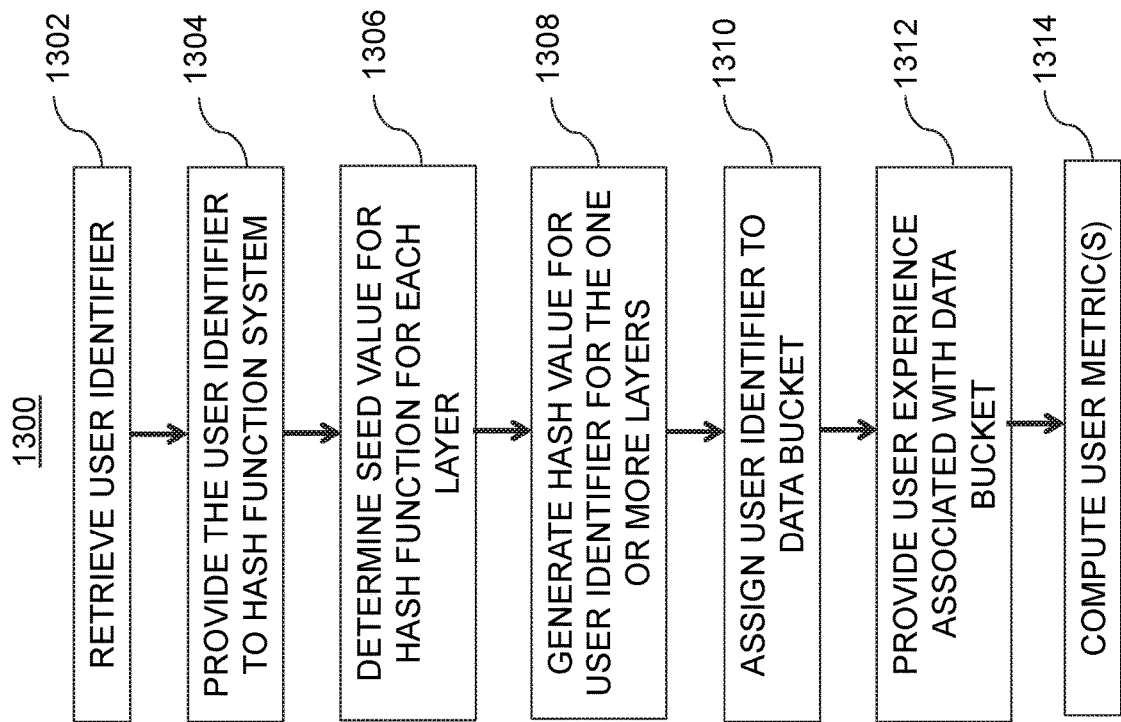
FIG. 13 is an illustrative flowchart of an exemplary process for providing user experience(s) to data bucket(s) and computing user metric(s), in accordance with various embodiments of the present teachings.

FIG. 13 is an illustrative flowchart of an exemplary process for providing user experience(s) to data bucket(s) and computing user metric(s), in accordance with various embodiments of the present teachings. Process 1300 may, in a non-limiting embodiment, begin at step 1302. At step 1302, a user identifier may be retrieved. For instance, upon a request being received, a user identifier associated with the user device that provided the request may be determined. The request, in some embodiments, may correspond to a request for a user experience to be provided, or a general request for content. For example, inputting of a URL into a web browser by user 102 on user device 110 may correspond to one type of request. Alternatively, a request may correspond to an interaction with content already rendered by user device 110, such as, and without limitation, a click on a hyperlink, a click on an advertisement, a scroll, a tap, a swipe, or any other type of interaction, or any combination thereof. In any of the aforementioned instances, the user identifier associated with the received request may be determined by user ID receiver system 1212. In some embodiments, however, the user identifier may previously be determined, and therefore at step 1302, the user identifier may be retrieved from local storage (e.g., memory/storage 1204).

At step 1304, the user identifier may be provided to a hash function system. The hash function system may be part of data bucket assigner system 1214. The hash function, which may also be referred as a randomizer function, may be configured to randomly assigned the user identifier to a particular data bucket, which may be associated with a particular user experience (e.g., control user experience 1230, test user experience 1240). At step 1306, a seed value for the hash function for each online experiment may be determined. As mentioned previously, each experiment may exist on a layer in the multi-layer experimental platform. Each layer may include a unique seed value for the hash function, which is used for randomly assigning user identifiers to data buckets associated with that layer. At step 1308, a hash value for the user identifier for each layer may be determined. For example, as seen in FIG. 11, a same user identifier may be assigned to a different hash value in different layers. Persons of ordinary skill in the art will recognize that each user identifier need not be assigned to each layer of the multi-layer experimental platform. The generated hash value may also indicate the data bucket with which the user identifier is to be assigned.

At step 1310, the user identifier is assigned to a data bucket. For example, the user identifier may be assigned to a data bucket based on the hash value. At step 1312, a user experience associated with the data bucket that the user identifier has been assigned to may be provided to a corresponding user device. For example, if the user identifier has been assigned to a control data bucket, then the corresponding user device associated with that user identifier may be provided with a control user experience (e.g., control user experience 1230). As another example, if the user identifier has been assigned to a test data bucket, then the corresponding user device associated with that user identifier may be provided with the test user experience (e.g., test user experience 1240). At step 314, one or more use engagement metrics may be computed. For example, a days visited metric, a page view metric, and/or a sessions-based metric may be computed.

Figure 14A:
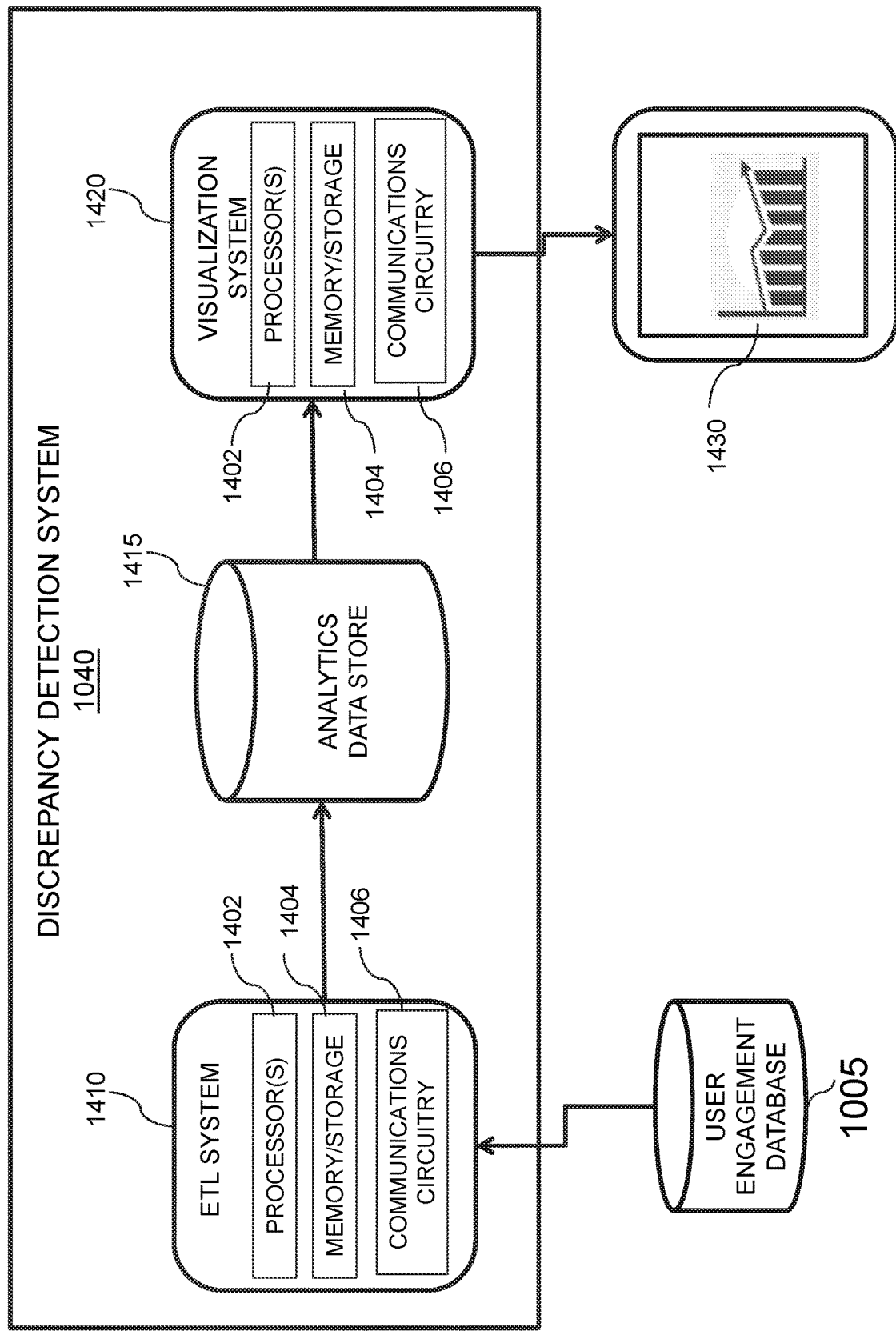
FIG. 14A is an illustrative diagram of an exemplary discrepancy detection system, in accordance with various embodiments of the present teachings.

FIG. 14A is an illustrative diagram of an exemplary discrepancy detection system, in accordance with various embodiments of the present teachings. Discrepancy detection system 1040, in a non-limiting embodiment, may include an Extract Transform and Load ("ETL") system 1410, a visualization system 1420, and an analytics data store 1415. ETL system 1410 and visualization system 1420, in one embodiment, may include one or more processors 1402, memory/storage 1404, and communications circuitry 1406. In some embodiments, processor(s) 1402, memory/storage 1404, and communications circuitry 1406 may be substantially similar to processor(s) 402, memory/storage 404, and communications circuitry 406 of FIG. 4, and the previous description may apply.

ETL system 1410, in some embodiments, may be configured to receive user engagement data from user engagement database 1005. ETL system 1410 may aggregate the user engagement data such that hourly and daily user engagement data is generated, which ETL system 1410 may in turn provide to analytics data store 1415 for storage. For example, ETL system 1410 may call on user engagement database 1005 periodically (e.g., every few seconds, every minute, every few minutes, every hour, etc.) to obtain user engagement data representing user activities with experimentation platform 1030 that occurred. Upon receipt, ETL system 1410 may aggregate temporally common data, which may be based on a particular temporal period with which the aggregation is to occur, and may generate the aggregated user engagement data and send the aggregated user engagement data to analytics data store 1415 for storage. In some embodiments, user engagement database 1005 may perform and/or obtain some or all of the aggregated user engagement data, and thus when user engagement database 1005 is called on by ETL system 1410, the previously aggregated user engagement data may be provided to ETL system 1410 and then transmitted to analytics data store 1415.

Analytics data store 1415, in the illustrative embodiment, stores the aggregated user engagement data for use in real time data analytics and reporting. Analytics data store 1415 may, in some embodiments, be configured to perform/facilitate aggregation of user engagement data, however persons of ordinary skill in the art will recognize that this is merely exemplary. In one non-limiting embodiment, analytics data store 1415 may be a column-oriented distributed data store, however any suitable data structure configuration may be employed for storing the data received from ETL system 1410.

Visualization system 1420 may, in some embodiments, be configured to process aggregated user engagement data received from analytics data store 1415, and may generate visualization data representing one or more graphics (e.g., images, text, video, etc.) to be displayed within a user interface 1430 for a user. Visualization system 1420 may be configured to employ various filters for visualizing and segmenting data for review by an experiment designer (e.g., user 102). For example, a visualization of a discrepancy between stamped user identifiers (e.g., user identifiers that have been properly flagged for a particular experiment) and non-stamped user identifiers (e.g., user identifiers that have been mistakenly or mysteriously assigned to a data bucket of an experiment).

Figure 14B:
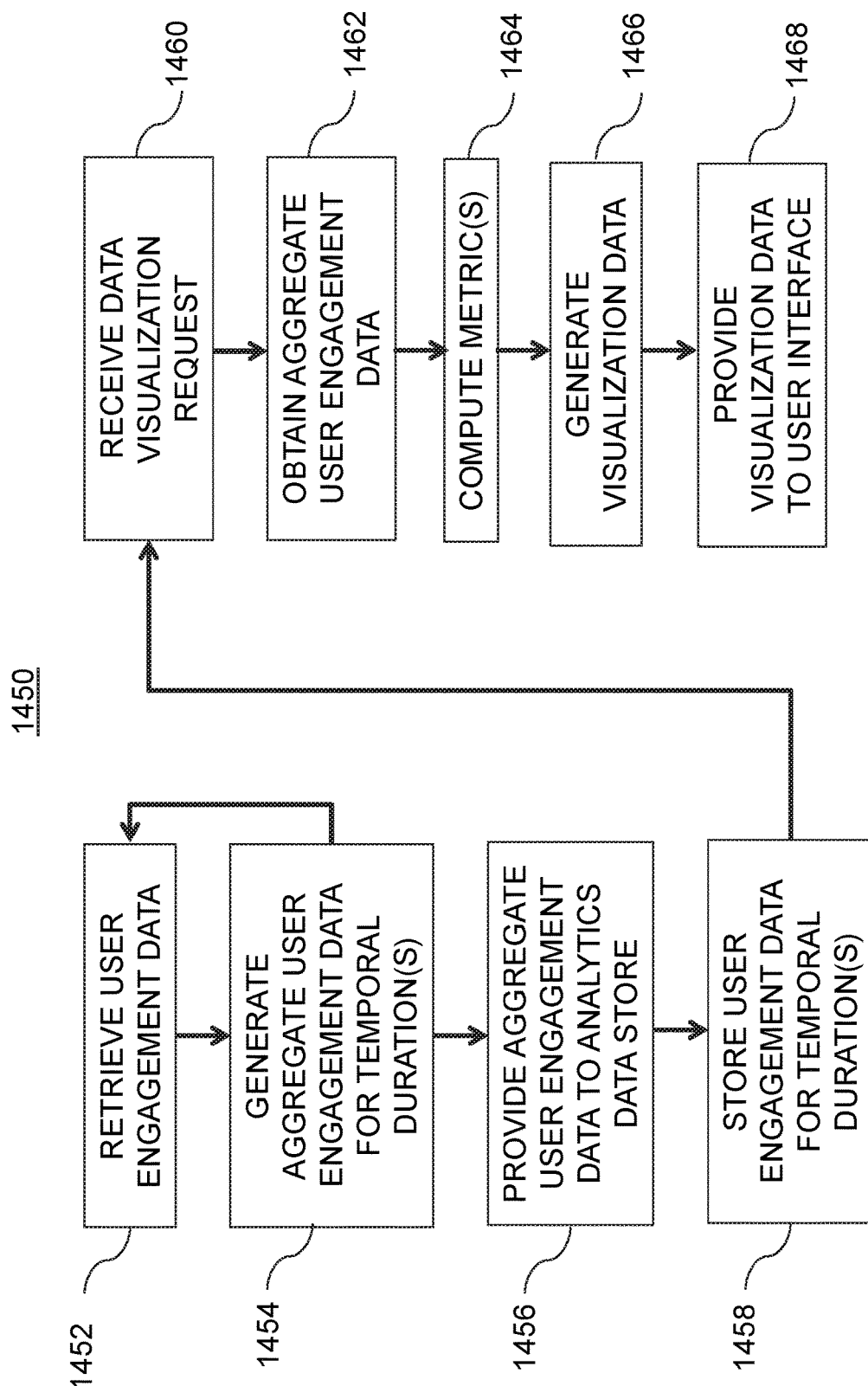
FIG. 14B is an illustrative flowchart of an exemplary processor for providing visualization data for various metrics, in accordance with various embodiments of the present teachings.

FIG. 14B is an illustrative flowchart of an exemplary processor for providing visualization data for various metrics, in accordance with various embodiments of the present teachings. Process 1450, in one embodiment, may begin at step 1452. At step 1452, user engagement data may be retrieved. For example, user engagement data representing user activities/user engagement information with content associated with an online experiment rendered by experimentation platform 1030 may be retrieved from user engagement database 1005.

At step 1454, aggregate user engagement data may be generated for one or more temporal durations. In some embodiments, ETL system 1410 may generate the aggregate user engagement data. For example, the user engagement data may be aggregated for hourly user engagement data and/or daily user engagement data, or any other suitable temporal duration of user engagement data. At step 1456, the aggregate user engagement data that was generated by ETL system 1410 may be provided to analytics data store 1415, and at step 1458, the aggregate user engagement data may be stored by analytics data store 1415. At step 1460, a data visualization request may be received by visualization system 1420. The data visualization request may be received from user device 110, from the experiment designer, or may be received automatically upon each instance of user engagement data being aggregated by ETL system 1410. At step 1462, the aggregate user engagement data may be obtained from analytics data store 1462. In some embodiments, the aggregate user engagement data may be obtained for a particular amount of time, which may be specified by the data visualization request. For example, the data visualization request may indicate the discrepancy data for a past seven days is to be presented, and therefore visualization system 1420 may obtain seven days' worth of aggregate user engagement data from analytics data store.

At step 1464, one or more metrics reflective of one or more user engagement parameters to be visualized may be computed. For example, a discrepancy between a number of user identifiers assigned to a data bucket for an online experiment as compared to a number of user identifiers expected to be assigned to the data bucket may be determined. At step 1466, visualization data representing the computed metric(s) may be generated. For example, visualization data representing the discrepancy between the expected size of a data bucket (e.g., number of user identifiers assigned to that data bucket) and the actual size of the data bucket (e.g., number of user identifiers receiving a metadata tag for that data bucket) may be generated. At step 1468, the visualization data may be provided to the user interface such that the computed metrics may be visualized by one or more users and/or experiment designers. For example, graphs 1800 and 1900 of FIGS. 18 and 19, respectively, may correspond to various types of visualization data that may be rendered by a user interface to detail discrepancy information associated with user engagement data.

Figure 15A:
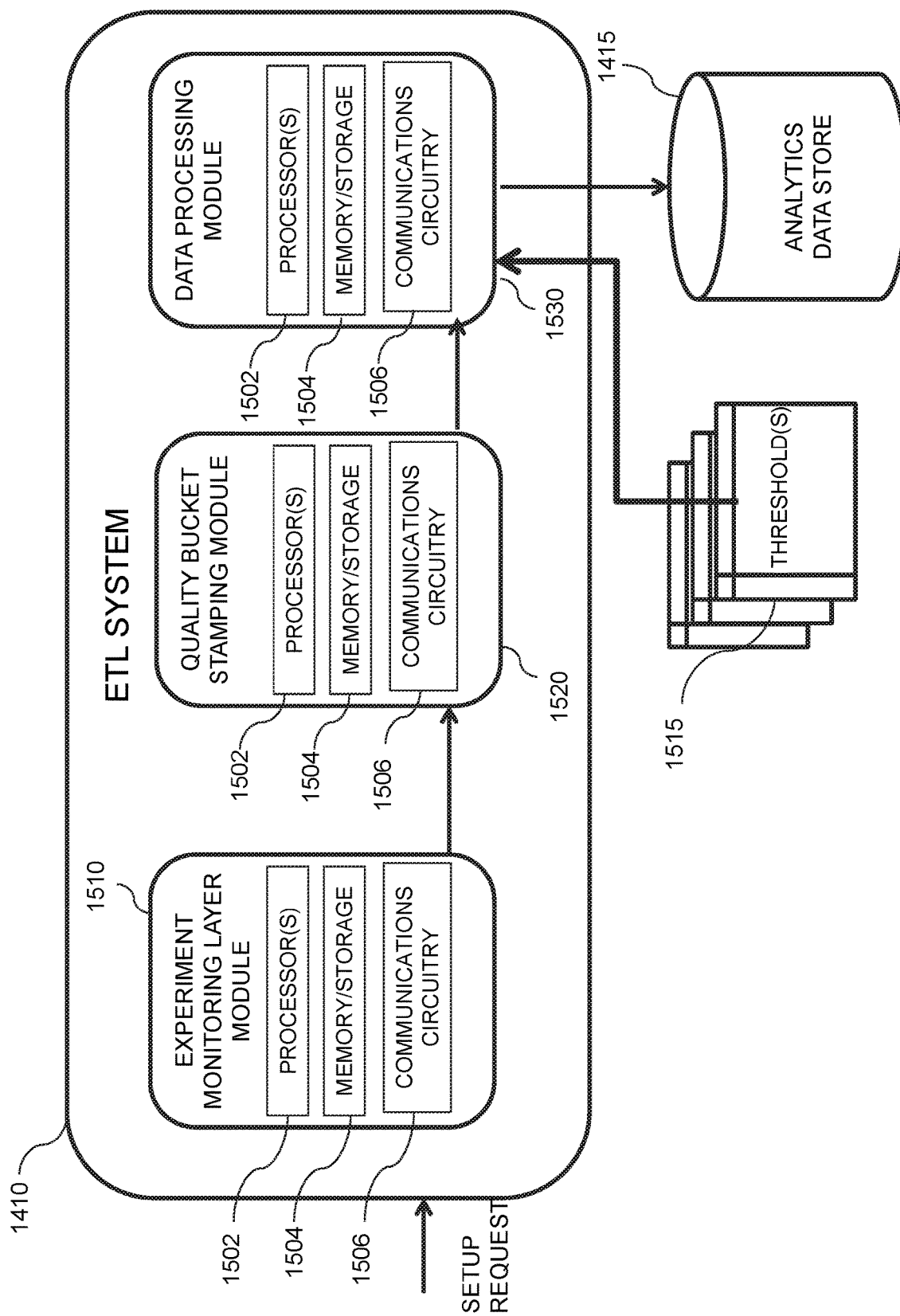
FIG. 15A is an illustrative diagram of an exemplary ETL system, in accordance with various embodiments of the present teachings.

FIG. 15A is an illustrative diagram of an exemplary ETL system, in accordance with various embodiments of the present teachings. In the non-limiting embodiment, ETL system 1410 may include an experiment monitoring layer module 1510, a quality bucket stamping module 1520, and a data processing module 1530. Each of experiment monitoring layer module 1510, quality bucket stamping module 1520, and data processing module 1530 may include one or more processors 1502, memory/storage 1504, and communications circuitry 1506. Processor(s) 1502, memory/storage 1504, and communications circuitry 1506 may, in some embodiments, be substantially similar to processor(s) 402, memory/storage 404, and communications circuitry 406 of FIG. 4, and the previous description may apply.

Experiment monitoring layer module 1510 may, in one embodiment, be configured to receive a setup request to set up an online experiment, or to set up discrepancy monitoring for an online experiment. In response to the request, experiment monitoring layer module 1510 may create a monitoring layer within the experimental platform (e.g., experimental platform 200, 1050). The monitoring layer may be a special layer which will be used for tracking quality issues associated with one or more experiments operating within the multi-layer experimentation platform 1050. The monitoring layer may, for instance, include a single data bucket, which may be referred to as a "quality bucket," and this data bucket uses 100% of the monitoring layer.

Quality bucket stamping module 1520 may be configured to assign a metadata tag to each user identifier placed into the monitoring layer. This process, which may also be referred to as "stamping," causes each user identifier to be attributed to the monitoring layer. Therefore, as platform 1050 is a multi-layer platform, the user identifiers not assigned into the monitoring layer may be subject to one or more underlying issues that may lead to discrepancies between actual data bucket size and expected data bucket size.

Data processing module 1530 may, in some embodiments, be configured to provide process the user engagement data that has been stamped by quality bucket stamping module 1520. For instance, data processing module 1530 may aggregate the user engagement data for various temporal durations. As an illustrative example, aggregated user engagement data may be generated every hour, every few hours, every day, and the like, and may be provided to analytics data store 1415 for storage. In some embodiments, one or more thresholds 1515 may also be obtained by data processing module 1530 and stored by analytics data store such that visualization system 1430 may generate appropriate visualization data. Threshold(s) 1515 may, for example, indicate whether or not a discrepancy is large enough to invalidate results of an online experiment.

Figure 15B:
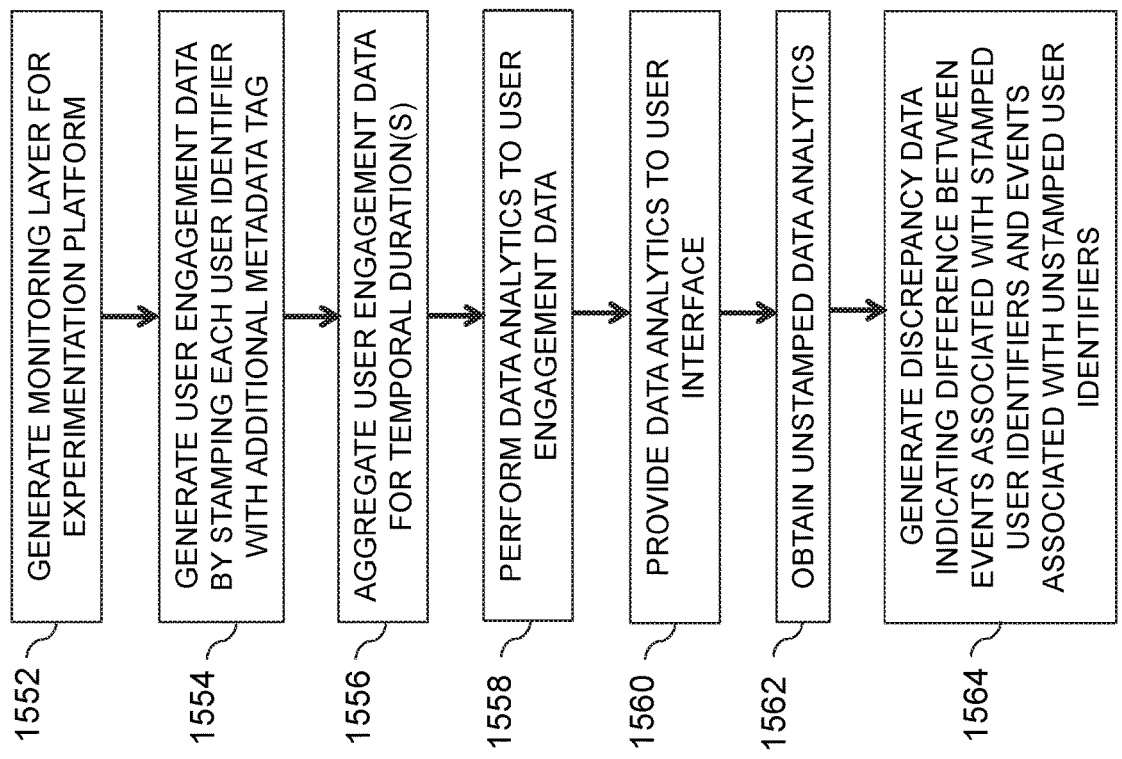
FIG. 15B is an illustrative flowchart of an exemplary processor for generating discrepancy data, in accordance with various embodiments of the present teachings.

FIG. 15B is an illustrative flowchart of an exemplary processor for generating discrepancy data, in accordance with various embodiments of the present teachings. Process 1550 may begin, in one embodiment, at step 1552. At step 1552, a monitoring layer may be generated for a multi-layer experimentation platform. For example, a monitoring layer may be generated within multi-layer experimentation platform 1050. The monitoring layer may include a single data bucket, which may occupy 100% of the monitoring layer.

At step 1554, user engagement data may be generated by stamping each user identifier with an additional metadata tag. For instance, each user identifier may, in addition to be distributed to one or more of the layers of multi-layer experimentation platform 1050, be distributed to the monitoring layer. Therefore, these user identifiers may further receive a metadata tag associated with the monitoring layer or, more particularly, attributed to a data bucket of the monitoring layer.

A user agent string may include a user identifier (e.g., a string of characters unique to a user device, browser, etc.), followed by one or more additional indicators. In some embodiments, some of the additional indicators may indicate whether that user identifier is associated with a particular layer of multi-layer experimentation platform. As an illustrative example, multi-layer experimentation platform 1050 may include a monitoring layer and a first layer. The first layer may include a single online experiment including two data buckets: a control data bucket associated with a control user experience, and a test data bucket associated with a test user experience. The user agent string may, therefore, include a certain amount of characters representative of a user identifier (e.g., abcd1234), followed by two additional characters. The first additional character may correspond to a logical 1 (e.g., "1"), which may indicate that the user identifier has been assigned to the monitoring layer's data bucket. The second additional character may correspond to either a logical 1 or a logical 0 (e.g., "0"), indicating that the user identifier has been assigned to either the control data bucket of the first layer or the test data bucket of the second layer, respectively. Therefore, when the user engagement data is stamped, each user identifier is attributed with an additional character in their user agent string (e.g., logical 1) reflective of the fact that the user identifier has been attributed to the monitoring layer.

At step 1556, the user engagement data may be aggregated for various temporal durations. For example, the user engagement data may be aggregated such that hourly data, daily data, weekly data, and the like may be obtained. At step 1558, data analytics may be performed to the user engagement data. For example, user engagement metrics may be computed describing one or more user engagement parameters based on the user engagement data. In some embodiments, the data analytics that are performed may further be performed to determine a number of user identifiers included within the user engagement data that include the monitoring layer's metadata tag. For example, the user engagement data for a first data bucket of an experiment may indicate that 70% of the user identifiers include a metadata tag associated with the monitoring layer. This may indicate, for example, that 30% of the user identifiers do not include the monitoring layer metadata tag, indicating that there is an abnormality occurring within the system architecture that causes those user identifiers to not be attributed with the additional metadata tag. Therefore, the results of the first experiment may be erroneous, or not completely accurate, as the difference between the number of user identifiers expected to be within the data bucket as opposed to the number of user identifiers actually within the data bucket is greater than expected.

At step 1560, the data analytics may be provided to a user interface. For instance, discrepancy detection system 1040 may provide the data analytics to visualization system 1420. At step 1562, unstamped data analytics may be obtained. In some embodiments, unstamped data analytics may be determined by data processing module 1530. For example, as described above, unstamped data analytics may indicate a number of user identifiers within each data bucket that lack the additional metadata tag associated with the monitoring layer. At step 1564, discrepancy data may be generated that indicates a difference between events associated with stamped user identifiers and events associated with unstamped user identifiers. The discrepancy data, in some embodiments, may take the user engagement data obtained and may determine the difference between the number of user identifiers including the metadata tag associated with the monitoring layer and the number of user identifiers expected to be in the data bucket. In some embodiments, data processing module 1530 may generate the discrepancy data, and may also obtain one or more thresholds 1515. The thresholds may be used to determine whether the discrepancy is large enough that results of the experiment being performed re unable to be used. In some embodiments, the discrepancy data may further be provided to visualization system 1420 for rendering on a user interface.

Figure 16:
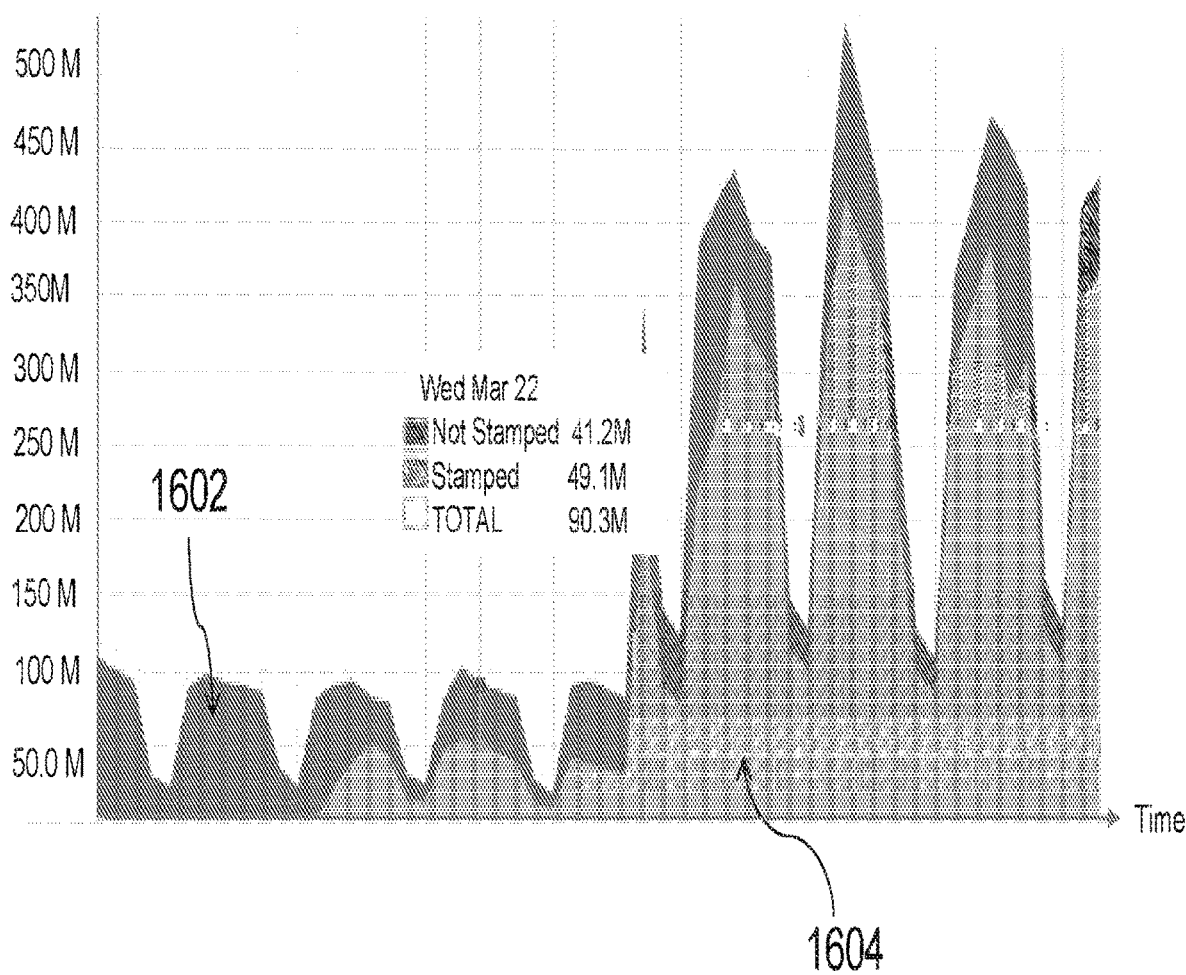
FIG. 16 is an illustrative graph of exemplary discrepancy data indicating a discrepancy for a data bucket of an online experiment, in accordance with various embodiments of the present teachings.

FIG. 16 is an illustrative graph of exemplary discrepancy data indicating a discrepancy for a data bucket of an online experiment, in accordance with various embodiments of the present teachings. Graph 1600 illustrates, in the non-limiting embodiment, discrepancies between stamped used identifiers and unstamped user identifiers over time for a particular experiment. For example, unstamped user identifiers 1602 and stamped user identifiers 1604 may exist in a same data bucket of an experiment. This implies that some user identifiers (e.g., unstamped user identifiers 1602) may be receiving one user experience that is not being measured by experimentation platform 1030. Furthermore, if the total number of user identifiers is the desired amount for a data bucket, then without determining that some of those user identifiers are unstamped, an experiment designer may erroneously read in findings to results of their online experiment. Additionally, user experience may suffer as the particular user experience provided to unstamped user identifiers 1602 may be unknown to the experimentation platform, as the data bucket assignment process may yield null results.

Figure 17:
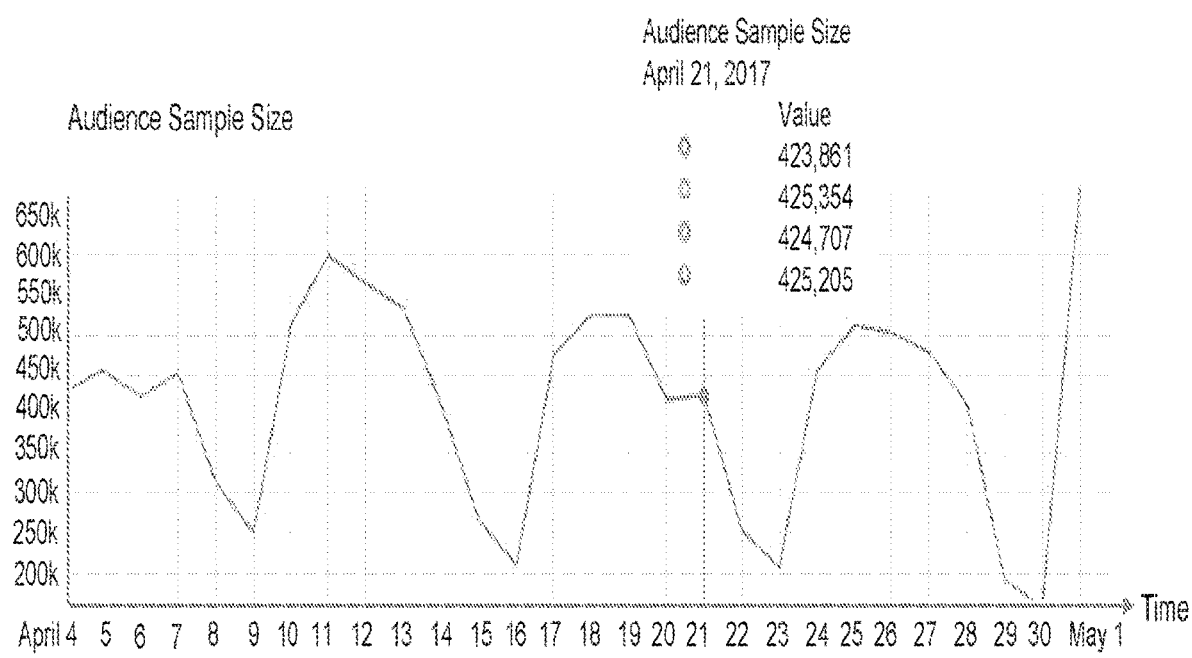
FIG. 17 is an illustrative graph of balanced data buckets where a portion of the user identifiers are not stamped, in accordance with various embodiments of the present teachings.

FIG. 17 is an illustrative graph of balanced data buckets where a portion of the user identifiers are not stamped, in accordance with various embodiments of the present teachings. In the non-limiting embodiment, graph 1700 describes a situation where data bucket size may be balanced across various data buckets of an online experiment. However, in the illustrative embodiment, roughly half of the user activity events receive a quality layer data bucket stamp. Therefore, even though A/A validation and A/B validation for the online experiment may indicate that the size of the data buckets is evenly distributed for each data bucket, at least some of the identifiers of those data buckets have not been stamped with the quality layer's metadata tag.

Figure 18:
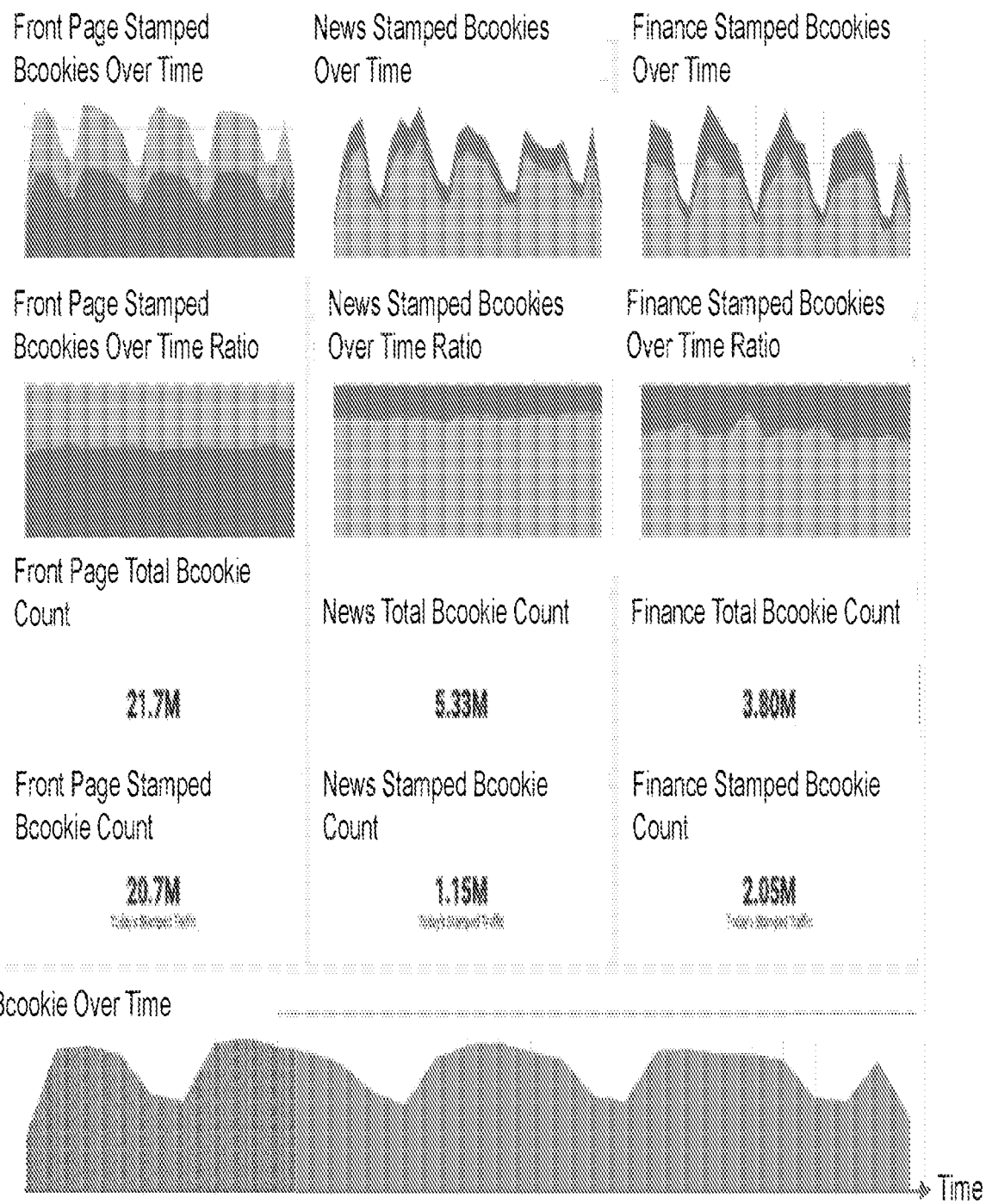
FIG. 18 is an illustrative diagram of various visualization data for rendering on a user interface detailing data bucket discrepancy for an online experiment, in accordance with various embodiments of the present teachings.

FIG. 18 is an illustrative diagram of various visualization data for rendering on a user interface detailing data bucket discrepancy for an online experiment, in accordance with various embodiments of the present teachings. User interface 1800 may, in some embodiments, display discrepancies in data bucket size over time. User interface 1800 may include various types of data analytics, as described above, to indicate an amount of unstamped user identifiers within a data bucket. For example, for a particular website, one or more webpages may be tracked, and a determination of a number of user identifiers that have been stamped and a number of user identifiers that have not been stamped may be displayed for each webpage of the website as they change over time. Furthermore, totals for a daily traffic volume, stamped user identifier volume, and changes in these parameters may also be visualized by user interface 1800.

Figure 19:
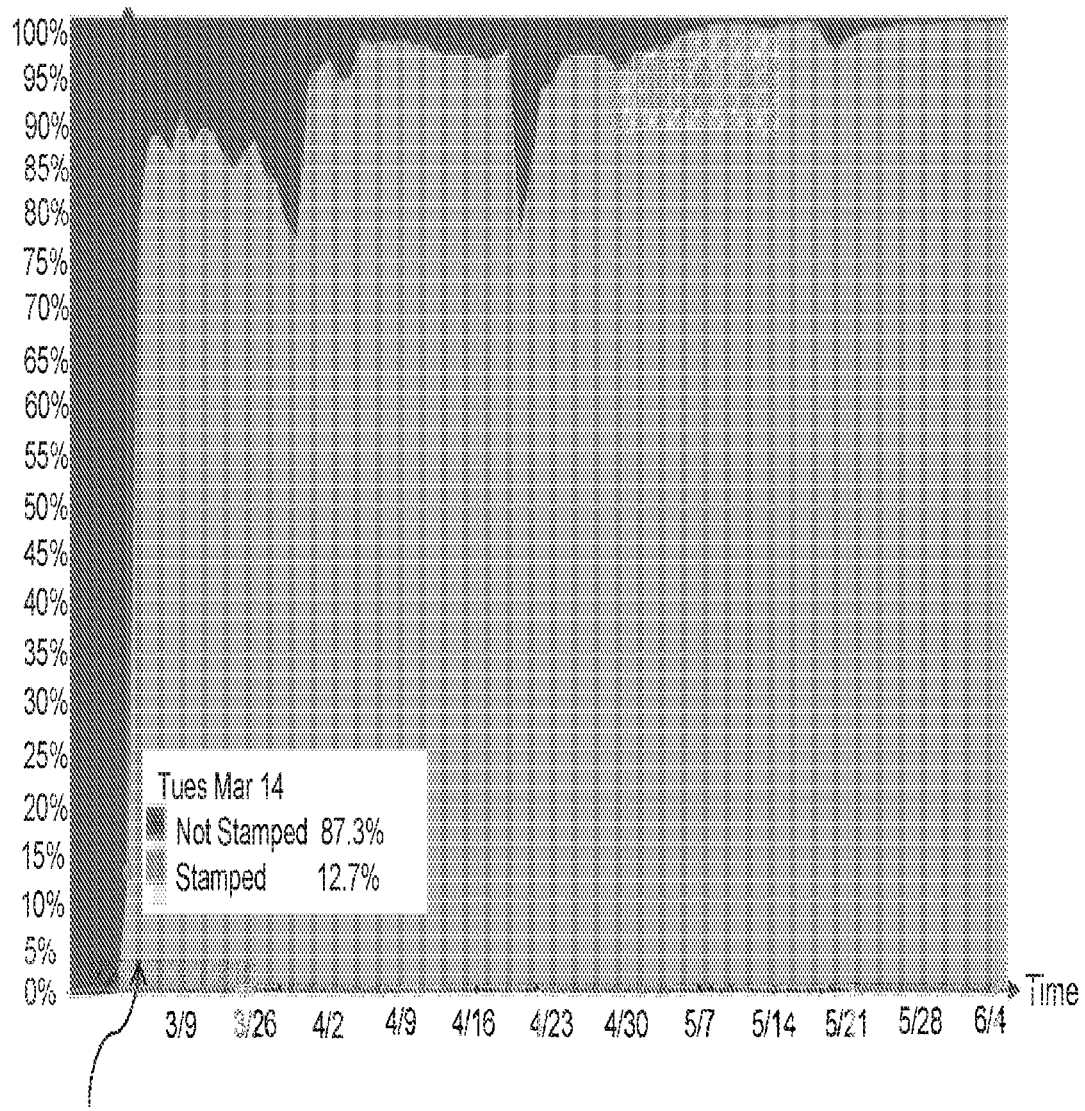
FIG. 19 is an illustrative diagram of an exemplary user interface detailing data bucket discrepancy over time, in accordance with various embodiments of the present teachings.

FIG. 19 is an illustrative diagram of an exemplary user interface detailing data bucket discrepancy over time, in accordance with various embodiments of the present teachings. In the non-limiting embodiment, graph 1900 describes one example graphic that may be rendered by user interface 1800. For instance, a ratio of the number of stamped user identifiers as compared to a number of unstamped user identifiers over a particular amount of time may be presented via graph 1900. As seen from graph 1900, a number of unstamped user identifiers may have accounted for a large portion of the user activity early on, however over time, with implementation of a monitoring layer within the experimentation platform, the ratio may decrease. Therefore, fewer and fewer unstamped user identifiers may remain in a data bucket for an experiment, thereby increasing the reliability of the experiment's results.

An additional benefit to implementing the monitoring layer to detect data bucket discrepancies is the ability to quickly and effectively identify experiments that are experiencing data bucket discrepancies. For example, at a time 1902, discrepancy detection system 1040 may detect that a ratio of unstamped user identifiers to stamped user identifiers for a particular data bucket may be in excess of a threshold (e.g., threshold 1515). In response, an experiment designer may dive into the details associated with the setup of the experiment within online experimentation platform 1030, and may rectify any issues that may exist. As seen from graph 1900, after time 1902, when an underlying issue was discovered, the number of unstamped user identifiers infiltrating the experiment's data bucket decreases.

Figure 20:
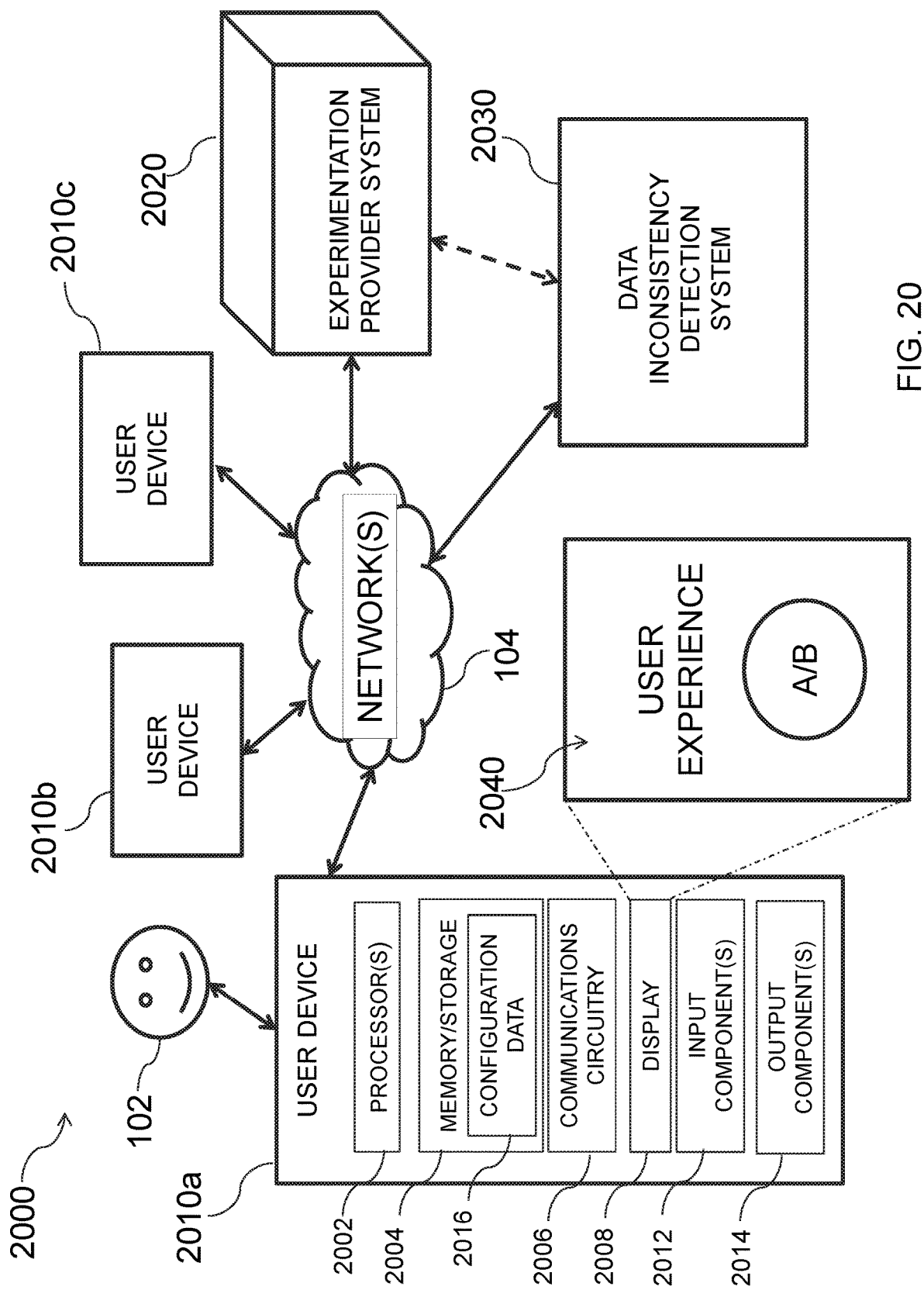
FIG. 20 is an illustrative diagram of an exemplary system for identifying data bucket overlap with online experiments, in accordance with various embodiments of the present teachings.

FIG. 20 is an illustrative diagram of an exemplary system for identifying data bucket overlap with online experiments, in accordance with various embodiments of the present teachings. In the non-limiting example embodiment, a system 2000 may include one or more user devices 2010*a*, 2010*b*, and 2010*c*. User devices 2010*a*, 2010*b*, and 2010*c* may be substantially similar to user device 110 of FIG. 1, and the previous description may apply. Furthermore, additional details associated with user devices 2010*a*, 2010*b*, and 2010*c*, which collectively may be referred to as user device(s) 2010, are described below. Although only three user devices 2010*a-c* are shown within system 2000, persons of ordinary skill in the art will recognize that any number of user devices may be employed, and the use of three user devices is merely exemplary.

User device 2010 may, in some embodiments, include one or more processors 2002, memory/storage 2004, communications circuitry 2006, a display or display functionality 2008, one or more input components 2012, and one or more output components 2014. In some embodiments, processor(s) 2002, memory/storage 2004, and communications circuitry 2006 may be substantially similar to processor(s) 402, memory/storage 404, and communications circuitry 406 of FIG. 4, and the previous description may apply. In some embodiments, memory/storage 2004 may be further configured to store configuration data 2016, which as described in greater detail below, may store user experience information indicating a user experience to be provided by user device 2010 when user device 2010 accesses experimentation provider system 2020.

Display 2008 may correspond to any suitable type of visual output component capable of presenting images and/or videos to user 102 via user device 2010. Various types of displays include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. Display 2008 may, in some embodiments, include a touch screen, such as a touch screen including capacitive sensing panels capable of recognizing touch inputs thereon. For instance, a touch screen may correspond to a projected capacitive touch ("PCT"), screen include one or more row traces and/or driving line traces, as well as one or more column traces and/or sensing lines. As described in greater detail herein, display 2008 may be configured to render a user experience 2040 thereon. User experience 2040 may correspond to one type of user experience associated with an online experiment with which user device 2010 is participating in via user device 2010 accessing experimentation provider system 2020. For example, user experience 2040 may correspond to a control user experience or a test user experience, and the type of user experience 2040 rendered by display 2008 may depend on configuration data 2016. Furthermore, a type of user experience 2040 to be rendered by display 2008 may be determined by experimentation provider system 2020, based on a data bucket assignment process, which is described in greater detail above.

Input components 2012 may correspond to any suitable input mechanism. For example, continuing the aforementioned discussion, if display 2008 includes touch screen capabilities, display screen 2008 may also function as an input component. Additionally, or alternatively, input components 2012 may include, but are not limited to, a mouse, a stylus, a keyboard, voice processing components, a microphone, facial/object recognition functionality, and/or any other suitable input component, or any combination thereof.

Output component(s) 2014 may correspond to any suitable output mechanism for user device 2010. For example, continuing the aforementioned discussion, display 2008 may correspond to one type of output component (e.g., a visual output component). In some embodiments, output component(s) 2014 may correspond to one or more audio output components and/or one or more haptic components. For example, user device 2010 may include one or more speakers and/or transducers for outputting sound, and/or one or more haptic devices for output haptic feedback (e.g., vibrating components). In some embodiments, output component(s) 2014 may further include one or more interfaces that allow user device 2010 to communicate with one or more additional components, devices, and/or systems. For instance, output component(s) 2014 may include a USB interface, and HDMI interface, and/or any other interface component as persons of ordinary skill in the art will recognize.

System 2000 may further include an experimentation provider system 2020, which may be in communication with user device(s) 2010 via network(s) 104. In some embodiments, experimentation provider system 2020 may be configured to provide an online experiment that is to be experienced and interacted with by user devices 2010. For instance, experimentation provider system 2020 may be substantially similar to experimentation system 1030 of FIG. 10, and the previous description may apply.

System 2000 may further include a data inconsistency detection system 2030. Data inconsistency detection system 2030 may be configured, as described in greater detail below, to determine whether any user identifiers have been assigned to two or more data buckets of experimentation provider system 2020. As mentioned previously, user identifiers may be assigned to data buckets for online experiments, and user devices whose user identifiers are assigned to same data bucket may receive a same user experience when accessing the online experiment. However, in the mobile realm, for example, slight differences occur between that of the non-mobile realm.

As mentioned previously, when a user device (e.g., user device 110) access an experimentation system (e.g., experimentation system 1030), a user identifier associated with that user device may be assigned to a data bucket for an experiment. This process may occur randomly, and if performed accurately, attributed each identifier to one data bucket in one layer of the multi-layer experimentation platform (if a multi-layer experimentation platform is employed).

In the mobile setting, however, there are slight variations to the data bucket assignment process. For instance, for mobile devices (e.g., user devices 2010a-c), instead of assigned a user identifier to a data bucket, and then the experimentation system storing the user identifier and assigned data bucket within their system, the mobile device may store an indication of the data bucket assigned thereto locally. For example, user device 2010 may store configuration data 2016 within memory/storage 2004 that indicates a user experience to be provided to user device 2010. When user device 2010 first accesses experimentation provider system 2020, in one embodiment, the data bucket assignment process may occur, and information indicating the corresponding user experience to be provided to user device 2010 may be stored within a configuration file locally on user device 2010. The next instance that user device 2010 accesses experimentation provider system 2020, the configuration file may transmit the corresponding user experience information to experimentation provider system 2020, which in turn may provide the appropriate user experience 2040 to user device 2010.

Figure 21:
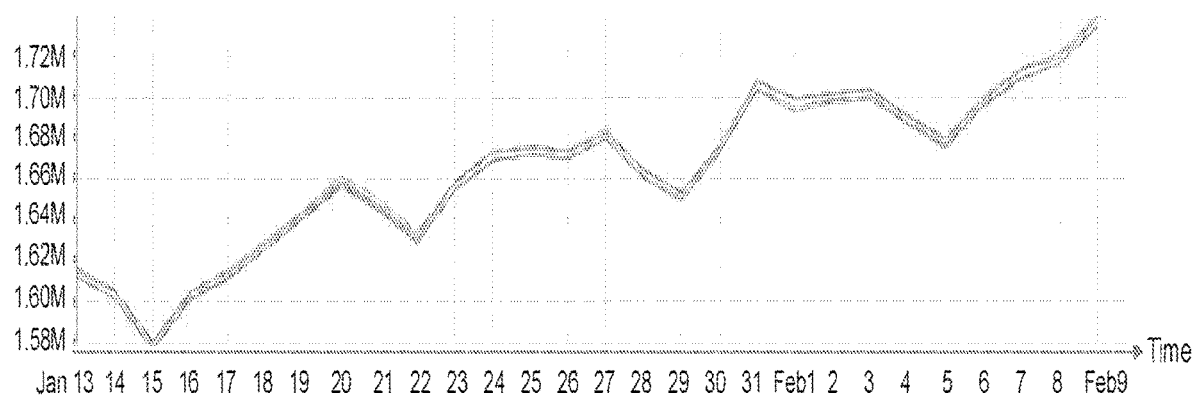
FIG. 21 is an illustrative graph indicating apparent data bucket size consistency over time, in accordance with various embodiments of the present teachings.

FIG. 21 is an illustrative graph indicating apparent data bucket size consistency over time, in accordance with various embodiments of the present teachings. In the illustrative, non-limiting embodiment, graph 2100 includes five different trend lines describing five different data buckets of an online experiment. As seen by graph 2100, each of the five data buckets appears to have a substantially same number of user identifiers. For example, each of the five data buckets appears to have a sample size of approximately 1.7 million. Additionally, as seen by graph 2100, the sample size of each of the five data buckets holds relatively steady compared with one another over time. This may appear as showing good distribution of identifiers to data buckets during experimentation, however there is no way of knowing whether or not one or more identifiers of one data bucket also is assigned to another data bucket or other data buckets. The assumption that there is no overlap of data bucket assignment for identifiers may prove to be detrimental to an experimentations validity and overall user experience. For instance, if one user device receives two or more user experiences associated with a same online experiment, then the results associated with that experiment may not be accurate. Furthermore, this can provide a poor user experience as the user may receive one user experience when accessing a webpage at one instance, but may receive a different user experience when accessing the same webpage at another instance.

Figure 22:
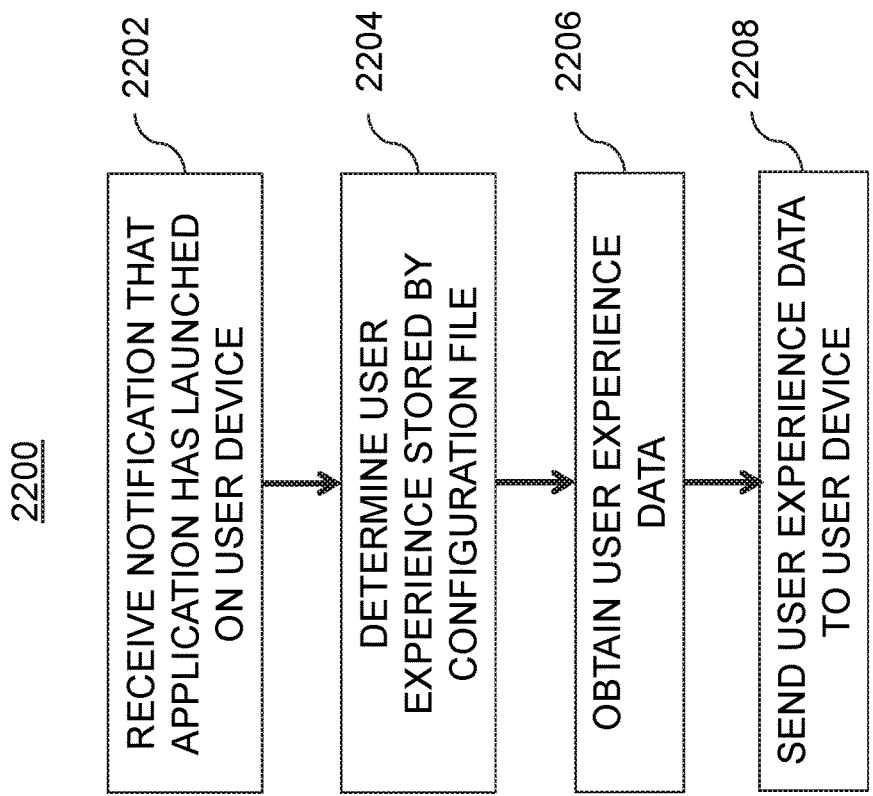
FIG. 22 is an illustrative flowchart of an exemplary process for sending user experience data to a user device based on a configuration file associated with the user device, in accordance with various embodiments of the present teachings.

FIG. 22 is an illustrative flowchart of an exemplary process for sending user experience data to a user device based on a configuration file associated with the user device, in accordance with various embodiments of the present teachings. Process 2200 may, in a non-limiting embodiment, begin at step 2202. At step 2202, a notification may be received by experimentation provider system 2020 that an application has launched on a user device. For instance, user 102 may open an application on user device 2010. An application, as described herein, may correspond to a web application that allows a user to view a website in a mobile setting. For example, the application, which may be stored within memory/storage 2004, may include data that, when read by processor(s) 2002, causes a web view of the website to be rendered by display 2008. As an illustrative example, the application may include JavaScript code that describes the layout and format to be used to render the content associated with the website. The differences between a web view version of a website and a browser view of the website may be primarily in appearance, as the content may be substantially the same, however persons of ordinary skill in the art will recognize that this is merely exemplary. For example, a social media site may have substantially the same content but a different appearance when accessed via one's mobile device as compared to a web browser.

In response to opening the application, which user 102 may accomplish by tapping an icon on display 2008, if display 2008 includes touch screen functionality, pressing a button, or performing any other suitable action. Upon determining that user 102 has invoked the application, the application may generate a notification to be sent by user device 2010 to experimentation provider system 2020 (or to the corresponding website) indicating that user device 2010 is requesting that content be rendered thereby. In some embodiments, the notification may include configuration data 2016, which may indicate, amongst other aspects, a user identifier associated with user device 2010 (e.g., a device identifier, MAC address, IP address), a location of user device 2010, a timestamp with which the request was generated, and/or any other suitable information, and/or any combination thereof.

At step 2204, a user experience stored by a configuration file may be determined. In response to receiving the notification, experimentation provider system 2020 may determine that configuration data 2016 includes a configuration file, which may also be referred to as configuration information and/or user experience information, indicating a user experience to be provided to user device 2010. For example, configuration data 2016 may include information indicating that user device 2010 has been assigned to a control data bucket. Therefore, in the illustrative example, experimentation provider system 2020 may determine that a control user experience is to be provided to user device 2010.

At step 2206, user experience data may be obtained. The user experience data may include visual data, audio data, text data, and/or any other type of data, reflective of the corresponding user experience to be provided to user device 2010. For instance, the user experience data may include a particular web view rendering of a website's content with which display 2008 may be configured to display. In some embodiments, the user experience data may include information capable of being read by user device 2010 (e.g., JavaScript information) such that user device 2010 may render the appropriate content without having to access the content via a web browser functionality of user device 2010. At step 2208, the user experience data may be sent to the user device that the notification was received from. In some embodiments, some aspects of the user experience, and thus portions of the user experience data, may be stored locally by user device 2010 (e.g., within memory/storage 2004), however persons of ordinary skill in the art will recognize that this is merely exemplary.

Figure 23:
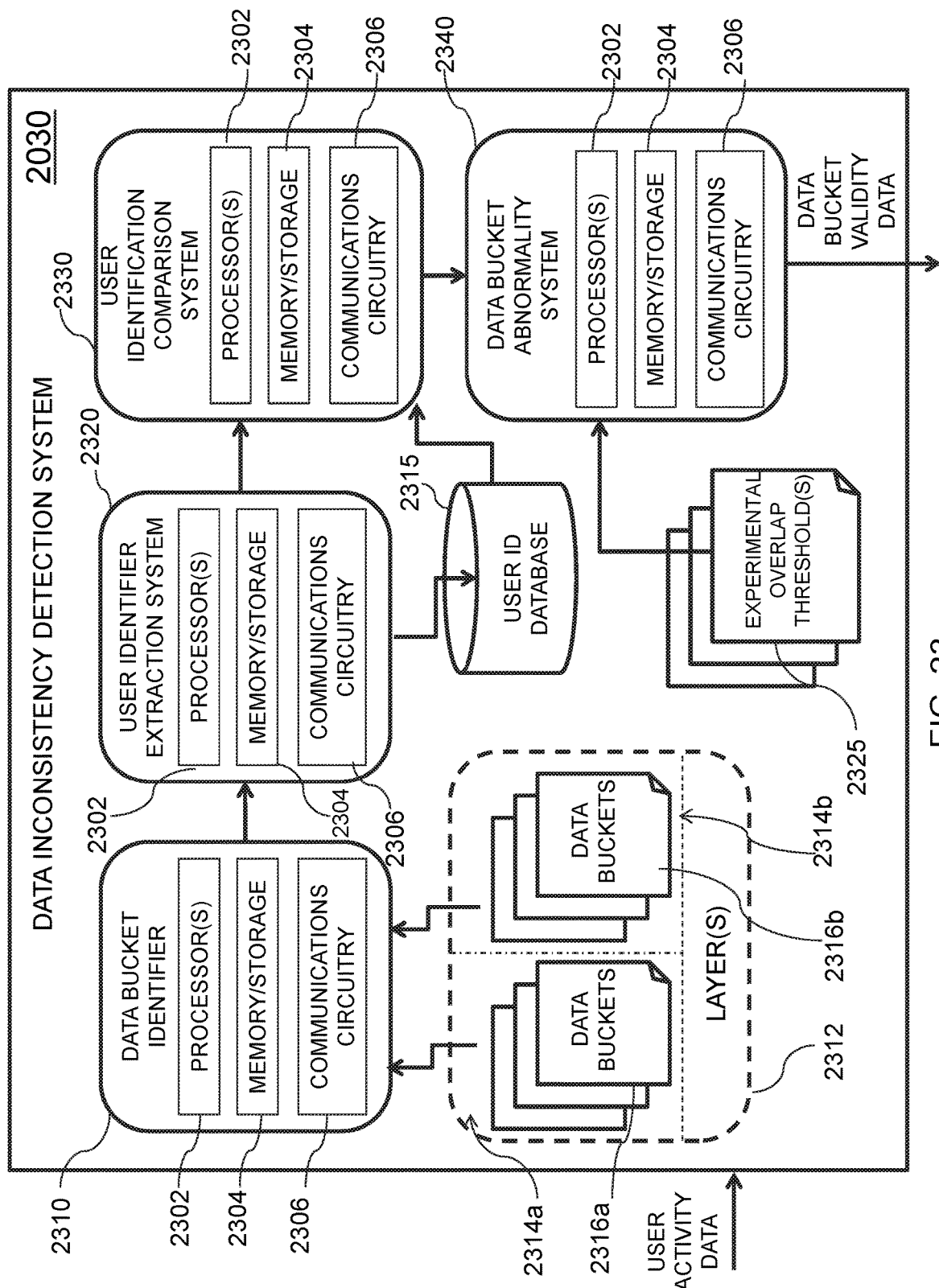
FIG. 23 is an illustrative diagram of an exemplary data inconsistency detection system, in accordance with various embodiments of the present teachings.

FIG. 23 is an illustrative diagram of an exemplary data inconsistency detection system, in accordance with various embodiments of the present teachings. Data inconsistency detection system 2030, as mentioned above, may be in communication with experimentation provider system 2020 directly and/or via network(s) 104. User activity data associated with an online experiment being provided by experimentation provider system 2020 and provided to user device(s) 2010 may additionally be received by data inconsistency detection system 2030. In some embodiments, data inconstancy detection system 2030 and experimentation provider system 2020 may receive the user activity data in parallel, however this is merely exemplary.

Data discrepancy detection system, in a non-limiting embodiment, may include a data bucket identifier 2310, a user identifier extraction system 2320, a user identification comparison system 2330, and a data bucket abnormality system 2340. Each of data bucket identifier 2310, user identifier extraction system 2320, user identification comparison system 2330, and data bucket abnormality system 2340 may include one or more processors 2302, memory/storage 2304, and communications circuitry 2306. Processor(s) 2303, memory/storage 2304, and communications circuitry 2306 may, in some embodiments, be substantially similar to processor(s) 402, memory/storage 404, and communications circuitry 406 of FIG. 4, and the previous description may apply.

In some embodiments, data inconsistency detection system 2030 may include multi-layer experimentation platform 2312, which may correspond to substantially similar experimentation layers provided by experimentation provider system 2020. For instance, data inconsistency detection system 2030 may reproduce the experimentation platform used by experimentation provider system 2020 for accurately monitoring inconstancies in data buckets. In some embodiments, however, platform 2312 may be optional, and thus may be omitted from data consistency detection system 2030. In this particular scenario, information regarding the activities and actions associated with each layer of the experimentation platform may be received from experimentation provider system 2020. In some embodiments, where multi-layer experimentation platform 2312 resides on data inconstancy detection system 2030, platform 2312 may be configured substantially similar to platform 1050 of FIG. 10 and/or platform 200 of FIG. 2, and the previous descriptions may apply.

As described in greater detail above, multi-experimentation platform 2312 may include one or more layers, such as a first layer 2314*a* and a second layer 2314*b*. In the illustrative embodiment, first layer 2314*a* and second layer 2314*b* may be orthogonal to one another, such that a user identifier may be capable of being placed in one data bucket in one layer and another data bucket in another layer. First layer 2314*a* may include one or more data buckets 2316*a*, and second layer 2314*b* may include one or more data buckets 2316*b*. In one embodiment, data buckets 2316*a* and 2316*b* may each correspond to two or more data buckets. For example, each of layers 2314*a* and 2314*b* may include at least a control data bucket and one test data bucket.

User activity data corresponding to activities performed to content associated with each of the layers of platform 2312 may be provided to data bucket identifier system 2310. Upon receipt, data bucket identifier system 2310 may be configured, in some embodiments, to determine a data bucket that a corresponding user identifier is associated. For example, the user activity data may include configuration data 2016, which indicates a data bucket that a corresponding user device has been assigned to. Upon accessing platform 2312, a user experience is provided to user device 2010 based on an assigned data bucket that configuration data 2016 identifies. Data bucket identifier 2310, as described in greater detail below, may be configured to determine the user experience based on which data bucket the corresponding user activity data is obtained from.

User identifier extraction system 2320 may, in some embodiments, be configured to determine a user identifier associated with the user activity data. For instance, in response to determine which data bucket a particular user activity or activities relate(s) to, user identifier extraction system 2320 may determine the user identifier associated with user device 2320. User identifier extraction system 2320 may then provide the user identifier to user ID database 2315. User ID database 2315 may, for instance, store pairing information indicating a user identifier and a corresponding data bucket or buckets that the user identifier is assigned to. In some embodiments, user ID database 2315 may further store a corresponding layer that each of the data buckets for that user identifier is associated with.

User identification comparison system 2330 may, in some embodiments, be configured to compare the user identifier associated with a particular user activity event with additional user identifiers stored by user ID database 2315. As an illustrative example, a first user identifier, ID 1, may be indicated as being associated with data bucket 1, DB 1, of layer 1, L1. Upon extraction by user identifier extraction system 2320, user identification comparison system 2330 may compare ID1 with each of the user identifiers that are also associated with L1. For instance, if layer 1 includes two data buckets, DB1 and DB 2, ID 1 may be compared with each of the user identifiers stored within user ID database 2315 as being associated with DB 2. If ID 1 does not match any of the user identifiers associated with DB 2, then this may indicate that there is no overlap between DB 1 and DB 2, at least with relation to ID 1. However, if ID 1 does match a user identifier associated with DB 2, then this may indicate that there is overlap between DB 1 and DB 2, as configuration data 2016 associated with ID 1 may be attributed to both DB 1 and DB 2, meaning user device 2010 may be capable of receiving two different user experiences. A similar process may also be performed across each of the various layers included within platform 2312 to determine overlap existing for each user identifier between two or more data buckets of each layer.

Data bucket abnormality system 2340 may be configured to receive the comparison results from system 2330 to determine a severity of the inconsistency. For example, a number of overlapping user identifiers between two or more data buckets of a same layer may be received by system 2340. System 2340 may then be configured to compare that number to experimental overlap threshold(s) 2325 to determine the extent of the overlap. In some embodiments, threshold(s) 2325 may be set by an experiment designer, or they may be defaulted to certain parameters. For example, overlaps of 10% or more of total user traffic may signify inconsistencies large enough to invalidate experimental results, however this is merely exemplary.

Figure 24:
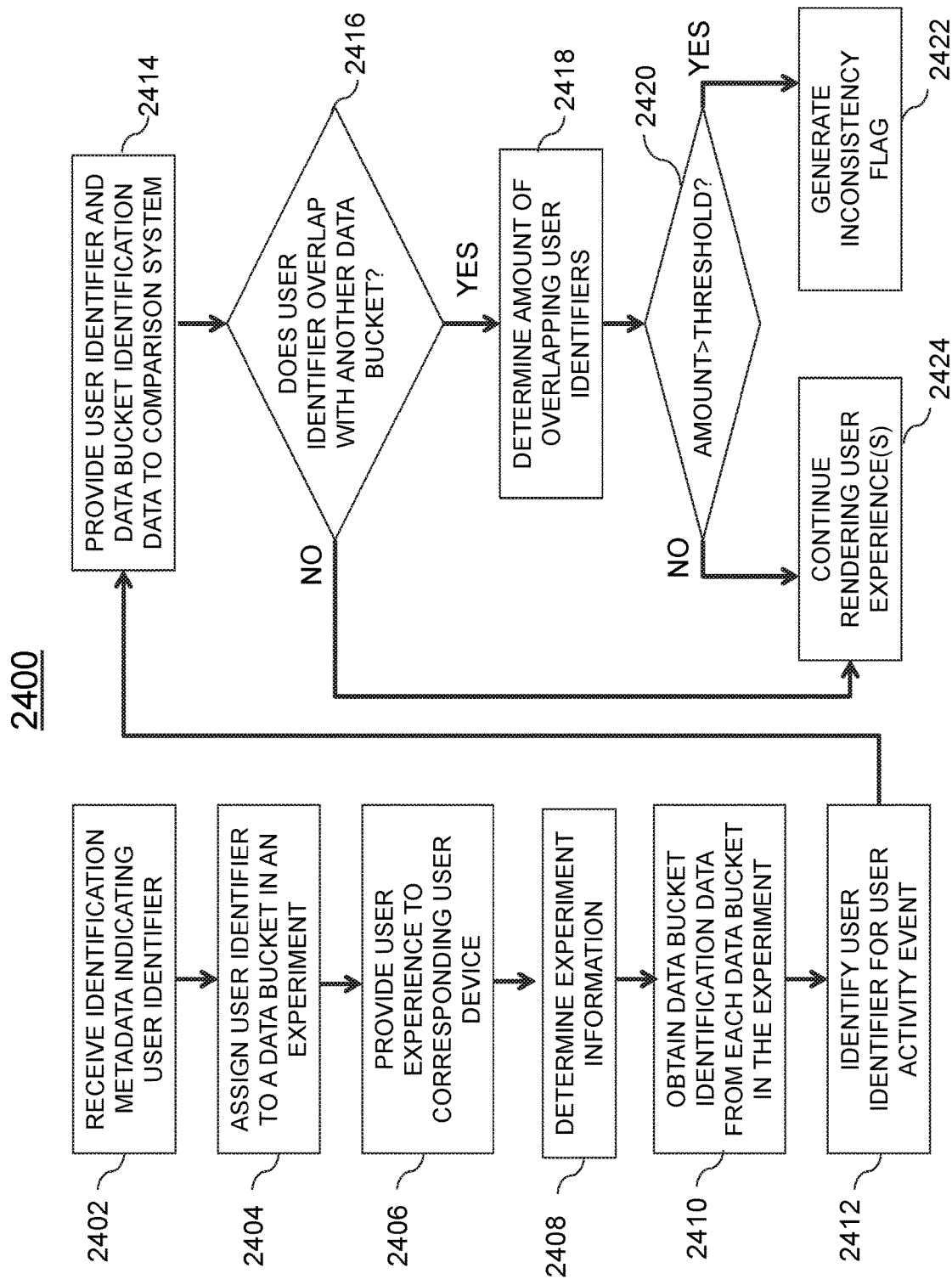
FIG. 24 is an illustrative flowchart of an exemplary processor for detecting data bucket inconsistency, in accordance with various embodiments of the present teachings.

FIG. 24 is an illustrative flowchart of an exemplary processor for detecting data bucket inconsistency, in accordance with various embodiments of the present teachings. In the non-limiting embodiment, process 2400 may being at step 2402. At step 2402, identification metadata indicating a user identifier associated with a user device 2010 may be received. For instance, the identification metadata may be received by platform 2312 and/or experimentation provider system 2020. At step 2404, the user identifier may be assigned to a data bucket in an experiment. For instance, upon first interacting with the online experiment, the user identifier may be assigned to a data bucket associated with the experiment. For example, the user identifier may be assigned to a control data bucket, associated with a control user experience, or a test data bucket, associated with a test user experience.

At step 2406, a user experience associated with the assigned data bucket may be provided to the user device. For example, if the user identifier was assigned to the control data bucket, then the control user experience may be provided to that user device 2010. In some embodiments, user device 2010 may store information indicating which user experience they have been attributed for the online experiment within configuration data 2016. At step 2408, experiment information may be determined. In some embodiments, the experiment information may indicate, amongst other aspects, a number of data buckets associated with the experiment, a number of additional experiments occurring within the platform, a number of user identifiers associated with the experiment, and the like.

At step 2410, data bucket identification data from each data bucket in the experiment may be obtained. The data bucket identification data may include a listing of each user identifier stored within user ID database 2315 for a particular experiment. At step 2412, a user identifier for a user activity event associated with the user activity data that is received may be identified. At step 2414, the user identifier and the data bucket identification data may be provided to comparison system 2330. Comparison system 2330, at step 2416, may be configured to determine whether the user identifier overlaps with any user identifiers associated another data bucket. For instance, the user identifier associated with one user activity event may be compared with the user identifiers associated with each other data bucket of an experiment.

If, at step 2416, comparison system 2330 determines that no overlap occurs, then process 2400 may proceed to step 2424, where the user experience(s) may continue being rendered. For example, an online experiment may include a first data bucket and a second data bucket, DB 1 and DB 2, respectively. A first user identifier ID 1 assigned to DB 1 may be compared with each user identifier associated with DB 2. If ID 1 does not match any of the user identifiers associated with DB 2, then the user experience being provided to ID 1 may continue to be provided thereto.

However, if at step 2416, comparison system 2330 determines that the user identifier does overlap with a user identifier in another data bucket, then process 2400 may proceed to step 2418. At step 2418, an amount of overlapping user identifiers may be determined. Continuing the example above, if ID 1 substantially matches another user identifier, ID 2, of DB 1, then the amount of overlapping user may correspond to one. However, if there are more user identifiers of DB 1 that also are associated with DB 2, then the amount of these identifiers may be determined.

At step 2420, a determination may be made as to whether or not the amount is greater than a threshold. For instance, the amount may be compared with threshold 2315 by system 2340 to determine an extent of the overlap. If, at step 2420, it is determined that the amount is less than or equal to the threshold, then process 2400 may proceed to step 2424. However, if at step 2420 it is determined the amount of overlapping user identifiers is greater than the threshold, then process 2400 may proceed to step 2422. At step 2422, an inconsistency flag may be generated. For instance, data bucket abnormality system 2340 may generate data bucket validity data including an inconsistency flag. The inconsistency flag may indicate to an experiment designer that there is significant overlap of users between data buckets, and therefore the results of the experiment may be inaccurate.

Figure 25A:
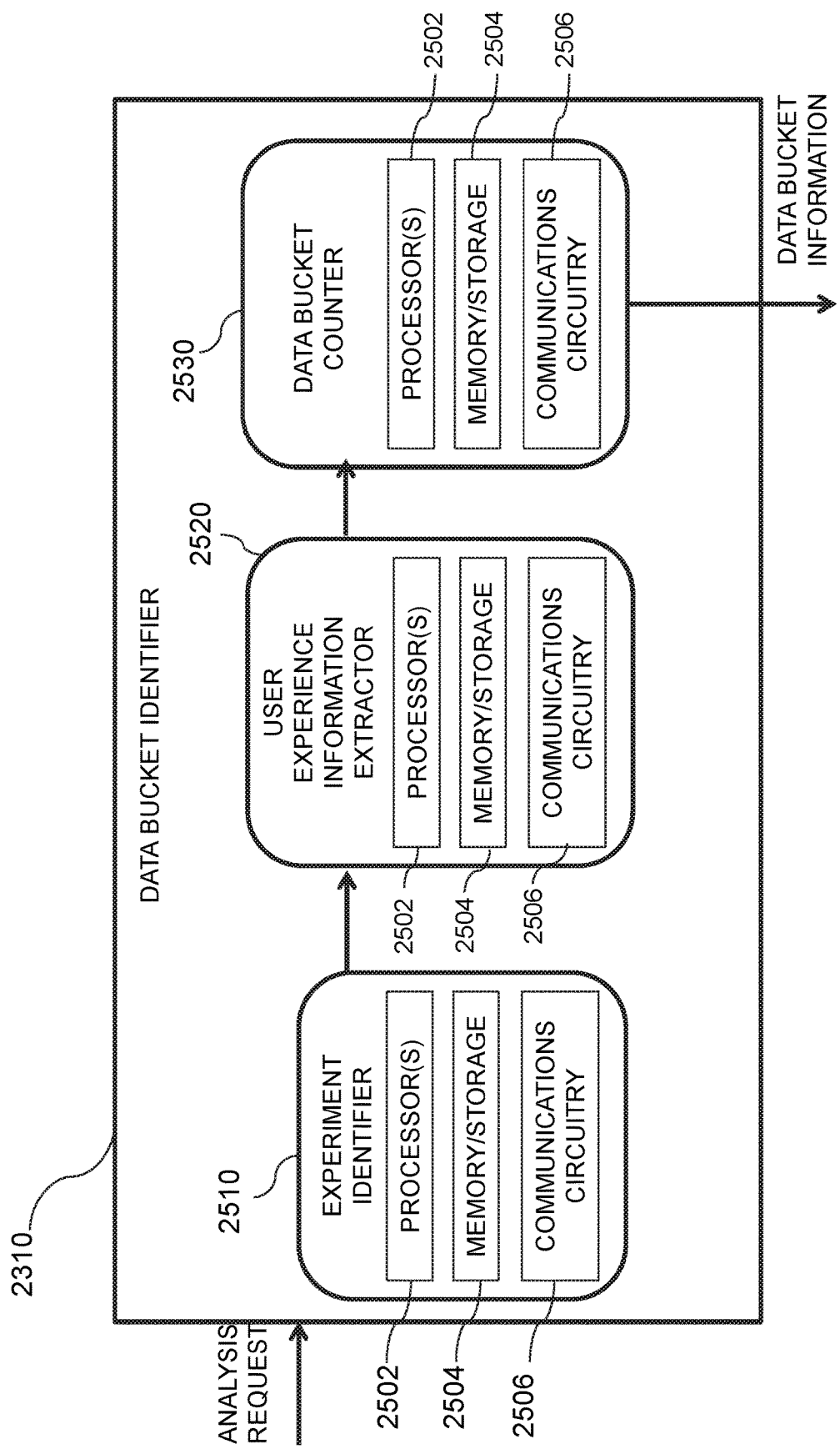
FIG. 25A is an illustrative diagram of an exemplary data bucket identifier system, in accordance with various embodiments of the present teachings.

FIG. 25A is an illustrative diagram of an exemplary data bucket identifier system, in accordance with various embodiments of the present teachings. Data bucket identifier system 2310, in the non-limiting embodiment, may include an experiment identifier system 2510, a user experience information extractor 2520, and a data bucket counter 2530. Each of experiment identifier system 2510, user experience information extractor 2520, and data bucket counter 2530 may include one or more processors 2502, memory/storage 2504, and communications circuitry 2506. In some embodiments, processor(s) 2502, memory/storage 2504, and communications circuitry 2506 may be substantially similar to processor(s) 402, memory/storage 404, and communications circuitry 406 of FIG. 4, and the previous descriptions may apply.

In the non-limiting embodiment, an analysis request received by data bucket identifier system 2310 may be provided to experiment identifier system 2510. Experiment identifier system 2510 may, in some embodiments, be configured to determine an experiment with which the analysis request is associated with. For example, experiment platform 2312 may include multiple experiments corresponding to different layers of platform 2312. Therefore, upon receipt of the request, experiment identifier 2510 may determine which experiment that the current request is associated. Additionally, in some embodiments, experiment identifier system 2510 may be configured to determine a corresponding layer of platform 2312 that the experiment occupies.

User experience information extractor system 2520 may, in some embodiments, be configured to determine user experience information associated with the identified experiment. For example, user experience information extractor system 2520 may determine a number of different data buckets associated with the experiment, and therefore a number of different user experiences capable of being provided for that experiment. Furthermore, user experience information extractor system 2520 may be configured to determine which user experience is a control user experience and which user experience, or experiences, is/are test user experiences.

Data bucket counter system 2530 may, in some embodiments, be configured to determine data bucket information associated with each data bucket of the experiment. For example, data bucket counter system 2530 may determine a total user identifier count (e.g., a sample size) associated with the each data bucket of the experiment, and thus a number of user devices 2010 that will, or that should, receive a particular user experience. Data bucket information, in one embodiment, may thus be output by data bucket counter system 2530, and therefore output by data bucket identifier system 2310, indicating a number of distinct data buckets associated with an experiment, and an approximate sample size of the data buckets.

Figure 25B:
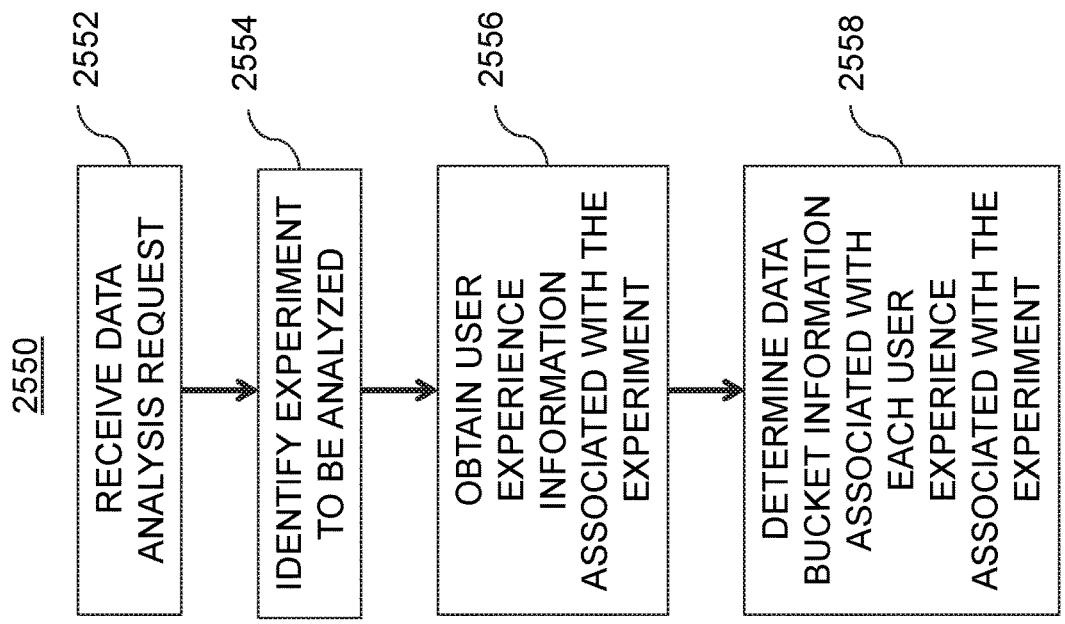
FIG. 25B of an illustrative flowchart of an exemplary process for determining data bucket information associated with each user experience of an online experiment, in accordance with various embodiments of the present teachings.

FIG. 25B of an illustrative flowchart of an exemplary process for determining data bucket information associated with each user experience of an online experiment, in accordance with various embodiments of the present teachings. Process 2550 may, in a non-limiting embodiment, begin at step 2552. At step 2552, a data analysis request may be received by data bucket identifier system 2310. In one embodiment, the request may be received by experiment identifier system 2510. At step 2554, an experiment to be analyzed may be identified by experiment identifier system 2510. For instance, experiment identifier system 2510 may determine an experiment associated with the request (e.g., an experiment associated with user device 2010 with which the request was received).

At step 2556, user experience information associated with the experiment may be obtained. For instance, user experience information extractor system 2520 may determine a number of data buckets associated with the identified experiment, and may determine the number and types of user experiences that are associated with each of the data buckets. At step 2558, data bucket information associated with each user experience associated with the experiment may be determined. For example, data bucket counter system 2530 may determine a total user identifier count (e.g., a sample size) associated with the each data bucket of the experiment, and thus a number of user devices 2010 that will, or that should, receive a particular user experience.

Figure 26A:
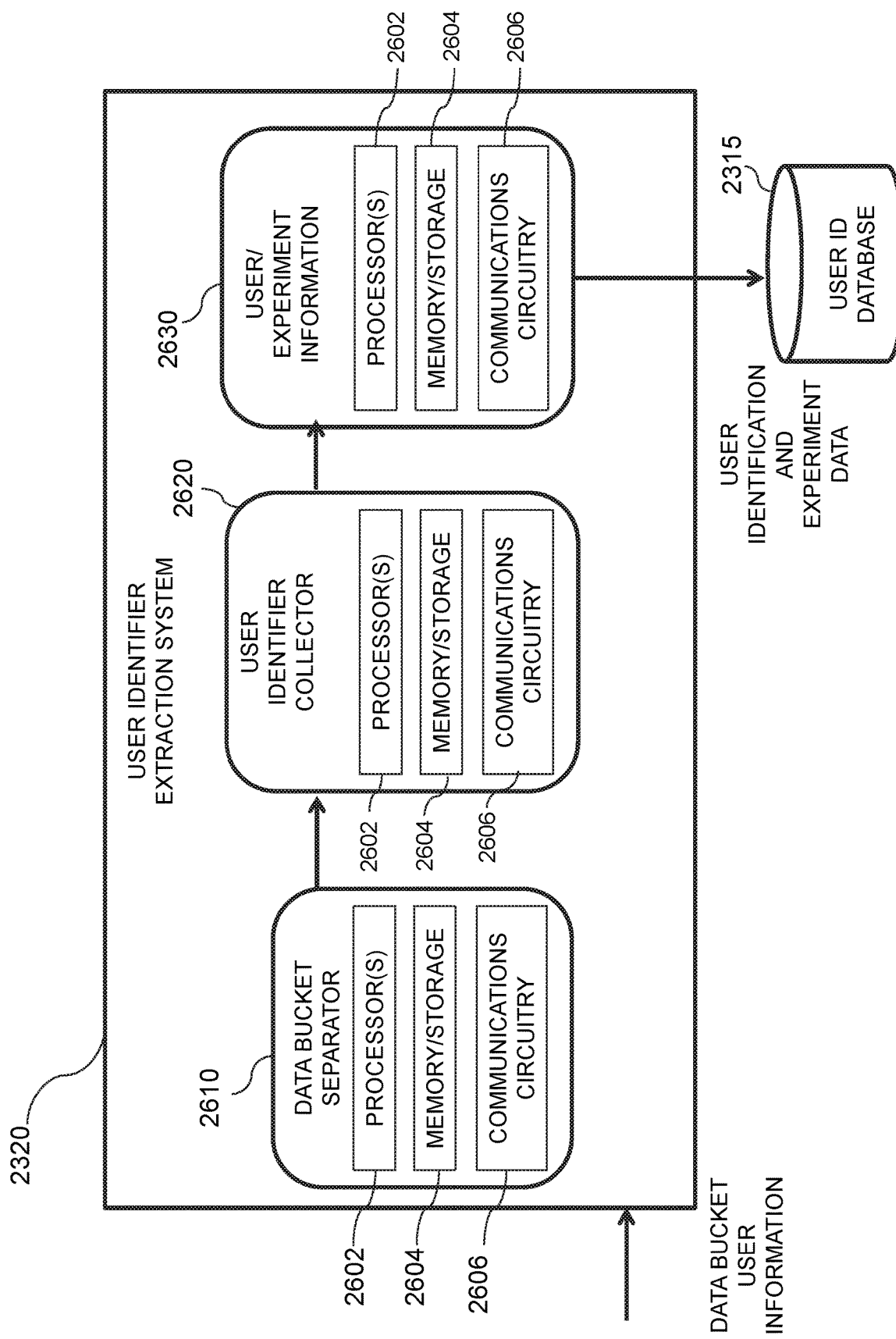
FIG. 26A is an illustrative diagram of an exemplary user identifier extraction system, in accordance with various embodiments of the present teachings.

FIG. 26A is an illustrative diagram of an exemplary user identifier extraction system, in accordance with various embodiments of the present teachings. User identifier extraction system 2320 may, in some embodiments, include a data bucket separator system 2610, a user identifier collector system 2620, and a user/experiment information system 2630. Each of data bucket separator system 2610, user identifier collector system 2620, and user/experiment information system 2630 may include one or more processors 2602, memory/storage 2604, and communications circuitry 2606. Processor(s) 2602, memory/storage 2604, and communications circuitry 2606 may, in some embodiments, be substantially similar to processor(s) 402, memory/storage 404, and communications circuitry 406 of FIG. 4, and the previous description may apply.

Data bucket separator system 2610 may, in some embodiments, be configured to receive data bucket user information. For instance, data bucket separator system 2610 may obtain data including user identifiers associated with an experiment (or more than one experiment), and corresponding data bucket metadata tags associated with those user identifiers. Each user identifier of the experiment should be associated with one data bucket, however in some embodiments, as described herein, additional data buckets of the same experiment may be assigned to a user identifier. Data bucket separator system 2610 may further be configured to separate out the user identifiers into groups by data bucket. For example, if there are two data buckets, DB 1 and DB 2, then data bucket separator system 2610 may group user identifiers together that include a metadata tag associated with DB 1, and may also group user identifiers together that include a metadata tag associated with DB 2.

User identifier collector 2620 may, in some embodiments, be configured to collect user identifiers for each data bucket together. For instance, first data bucket user identifier data may be generated by user identifier collector system 2620, which may include the various user identifiers associated with the first data bucket. Similarly, second data bucket user identifier data may be generated including the various user identifiers associated with the second data bucket. If more than two data buckets exists for a particular experiment, then data including the user identifiers for that bucket may also be included. Additionally, in some embodiments, user identifier data for data buckets of other experiments may also be collected by user identifier collector 2620 such that data for each data bucket of each experiment may be obtained.

User/experiment information system 2630 may, in some embodiments, be configured to determine the experiment associated with each collection of data generated by user identifier collector system 2620. For instance, system 2630 may determine a name associated with each experiment, a sample size designed for the data buckets of the experiments, and/or any other additional information, and/or any combination thereof. The user identification data and the experiment data may then be provided to user ID database 2315 for storage. User ID database 2315 may, therefore, be capable of storing data indicating, for each experiment existing in the experimentation platform 1050, a number of data buckets associated with each experiment, an expected data bucket size of each experiment, and the user identifiers that have been assigned to those data buckets.

Figure 26B:
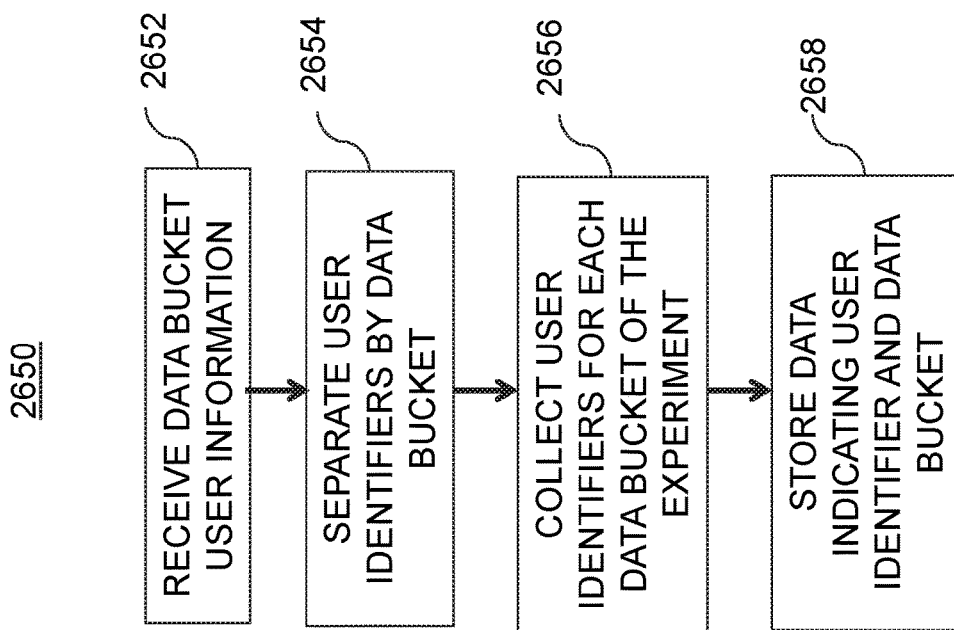
FIG. 26B is an illustrative flowchart of an exemplary processor for storing data indicating user identifiers and data buckets therefore, in accordance with various embodiments of the present teachings.

FIG. 26B is an illustrative flowchart of an exemplary processor for storing data indicating user identifiers and data buckets therefore, in accordance with various embodiments of the present teachings. Process 2650, in one example embodiment, may begin at step 2652. At step 2652, data bucket user information may be received. For example, data bucket user information may be received by data bucket separator system 2610 of user identifier extraction system 2320. At step 2654, user identifiers may be separated by data bucket based on the data bucket user information. For instance, data bucket separator system 2610 may be configured to separate the user identifiers based on the data bucket with which they are attributed to. At step 2656, the user identifiers for each data bucket of the experiment may be collected. For example, user identifier collector 2620 may collect, or otherwise group, user identifiers attributed with a common metadata tag associated with a same data bucket. In this way, all of the user identifiers having a metadata tag associated with a first data bucket may be grouped together, and all of the user identifiers having a metadata tag associated with a second data bucket may be grouped together. At step 2658, data indicating the user identifiers and data buckets associated therewith may be stored by user ID database 2315. In some embodiments, experiment information system 2630 may further provide information associated with the experiment(s) corresponding to those data buckets such that the information may also be stored by user ID database. For example, user ID database 2315 may store an expected sample size of a data bucket, and/or other information associated with the data buckets and experiments (e.g., whether a data bucket is a control data bucket or a test data bucket, a user experience associated with a data bucket, etc.).

Figure 27A:
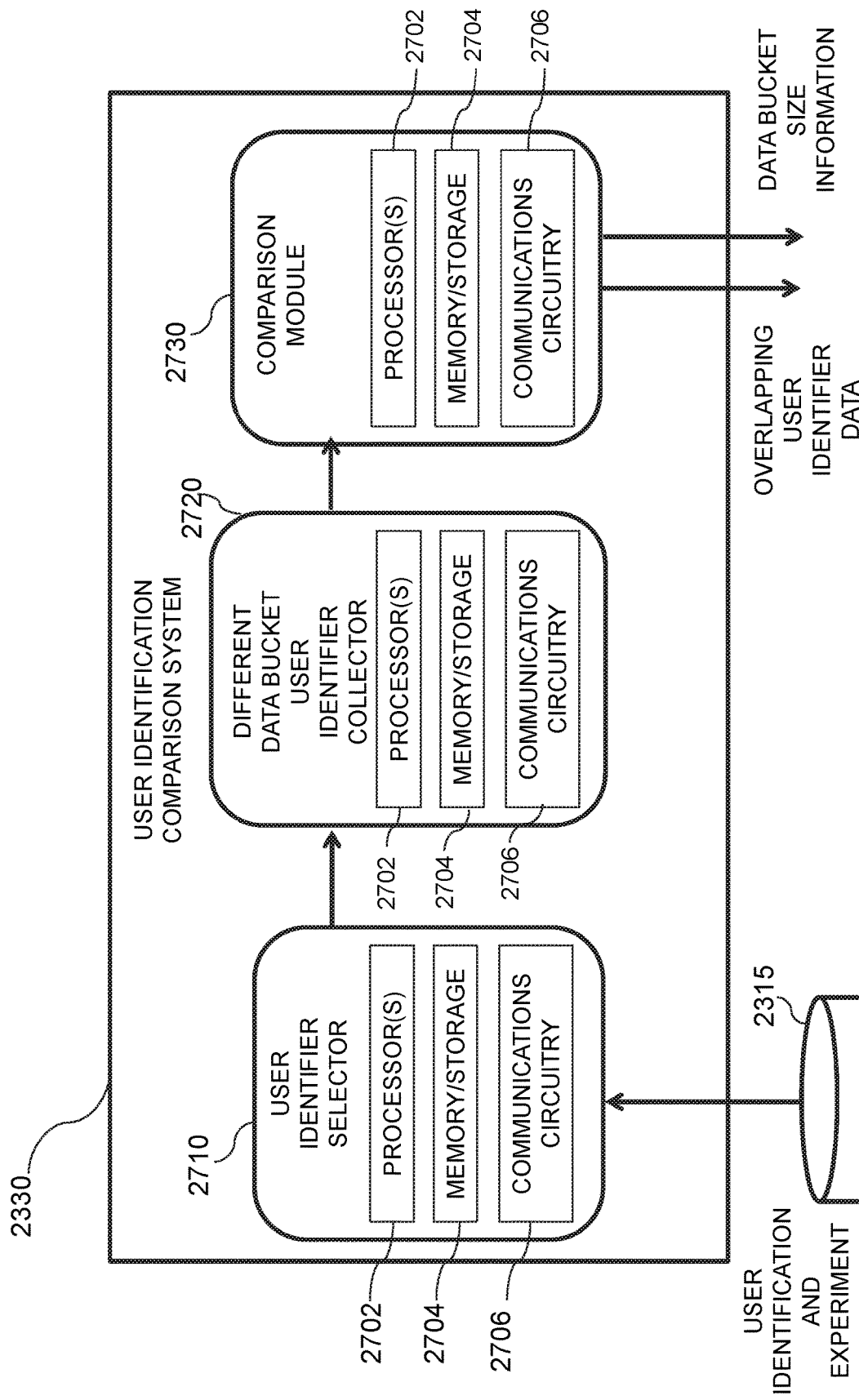
FIG. 27A is an illustrative diagram of an exemplary user identification comparison system, in accordance with various embodiments of the present teachings.

FIG. 27A is an illustrative diagram of an exemplary user identification comparison system, in accordance with various embodiments of the present teachings. In the non-limiting embodiment, user identification system 2330 may include a user identifier selector system 2710, a different data bucket user identifier collector system 2720, and a comparison module 2730. Each of user identifier selector system 2710, different data bucket user identifier collector system 2720, and comparison module 2730 may include one or more processors 2702, memory/storage 2704, and communications circuitry 2706. In some embodiments, processor(s) 2702, memory/storage 2704, and communications circuitry 2706 may be substantially similar to processor(s) 402, memory/storage 404, and communications circuitry 406, and the previous description may apply.

User identifier selector system 2710, in one embodiment, may be configured to obtain user identification and experiment data from user ID database 2315. In some embodiments, user identifier selector 2710 may be configured to select a user identifier from the received data, and may determine a data bucket associated with the selected user identifier. For example, user identification and experiment data may include, amongst other features, user identifier data representing a plurality of user identifiers associated with at least one experiment. Selector system 2710 may be configured to isolate one (or possibly more) user identifier from the data, with which to use for comparison purposes. In some embodiments, user identification comparison system 2330 may include multiple instances of selector system 2710 (and/or systems 2720 and 2730) such that a comparison process may be performed for multiple user identifiers in parallel.

Different data bucket user identifier collector system 2720 may, in some embodiments, be configured to determine a data bucket associated with the selected user identifier, and may obtain user identifiers associated with each of the one or more other data buckets. For example, if the selected user identifier, ID 1, is associated with a first data bucket DB 1 of a first experiment, then system 2720 may collect all of the user identifiers associated with a second data bucket DB 2 of the first experiment. Similarly, system 2720 may be configured to collect user identifier data representing user identifiers of data buckets associated with other experiments also occurring within the experimentation platform.

Comparison module 2730 may, in some embodiments, be configured to receive the selected user identifier associated with a first data bucket and the plurality of user identifiers associated with at least a second data bucket used for comparison. Comparison module 2730 may then be configured to determine whether or not the selected user identifier also exists in the collection of user identifiers associated with the second data bucket. If so, then this may indicate that the selected user identifier has been attributed to more than one data bucket within a same experiment. Comparison module 2730, and similarly systems 2710 and 2720, may be configured to perform a similar procedure for each user identifier in each data bucket such that a total number of overlapping user identifiers may be determined. Comparison module 2730, and thus system 2330, may therefore be configured to generate overlapping user identifier data that indicates a number of overlapping user identifiers determined to exist for a given data bucket. Comparison module 2730 may further be configured to output data bucket size information indicating an expected/measured size of the data bucket.

FIG. 27B is an illustrative flowchart of an exemplary process for generating data indicating overlap, in accordance with various embodiments of the present teachings. Process 2750, in a non-limiting embodiment, may begin at step 2752. At step 2752, user identifier data for an experiment may be received. For instance, user identifier data may be received by user identifier selector system 2710 from user ID database 2315. At step 2754, a first user identifier from a first data bucket may be isolated. The first user identifier may be selected at random, in some embodiments, by selector system 2710.

At step 2756, the first user identifier may be compared with user identifiers in additional data buckets. In some embodiments, system 2720 may obtain user identifier data representing user identifiers associated with a different data bucket than the selected user identifier's corresponding data bucket. In one embodiment, the different data bucket and the selected user identifier's data bucket are both associated with a same online experiment. At step 2758, a determination may be made as to whether a match has been identified between the selected user identifier of one data bucket and any of the user identifiers associated with the different data bucket.

If, at step 2758, it is determined that a match, or matches, have been found, then process 2750 may proceed to step 2760. At step 2760, count data indicating overlap between data buckets may be generated. In some embodiments, comparison module 2730 may generate count data indicating a number of matches found at step 2758. For example, if the first user identifier is determined to match another user identifier of the different data bucket, then the count data may indicate that one overlap has been found between the two data buckets. If, however, there are more than two data buckets, then step 2756 and 2758 may similarly be performed for each of the other data buckets to determine if overlap between the first user identifier and the user identifiers of the other data buckets exist. Additional count data reflecting the overlap for that other data bucket(s) may also be generated.

After step 2760, process 2750 may proceed to step 2762. Similarly, if no match was identified at step 2758, process 2750 may proceed to step 2762. At step 2762, a determination may be made as to whether the first user identifier isolated at step 2754 is a last identifier in the first data bucket. If not, then process 2750 may proceed to step 2764. At step 2764, a second user identifier may be isolated from the first data bucket, and process 2750 may proceed to step 2756 may repeat using the second user identifier. This process may loop until it is determined at step 2762 that the compared user identifier is the last identifier in the data bucket, or in other words, there are no more user identifiers to be compared. However, in some embodiments, multiple instances of systems 2710, 2720, and 2730 may be implemented within system 2330, and therefore some of the comparisons of user identifiers with other identifiers may occur in parallel with one another.

If, at step 2762, it is determined that the identifier user for comparison is in fact the last identifier associated with the data bucket (e.g., there are no more user identifiers left to perform comparisons with), then process 2750 may proceed to step 2766. At step 2766, the count data may be aggregated. For instance, each instance of an overlap being found may increment a counter associated with comparison module 2730, and the aggregate count may be determined at step 2766. At step 2768, output data indicating a total overlap may be generated. Additionally, in some embodiments, output data indicating a total data bucket size may also be generated. For example, if 100 user identifiers of a first data bucket are also determined to exist in the second data bucket, then the output data may indicate that the overlap is 100. If the total number of user identifiers in both data buckets is 1,000 identifiers, then the overlap percentage/ratio may be referred to as 10% overlap, however persons of ordinary skill in the art will recognize that this is merely exemplary.

Figure 28A:
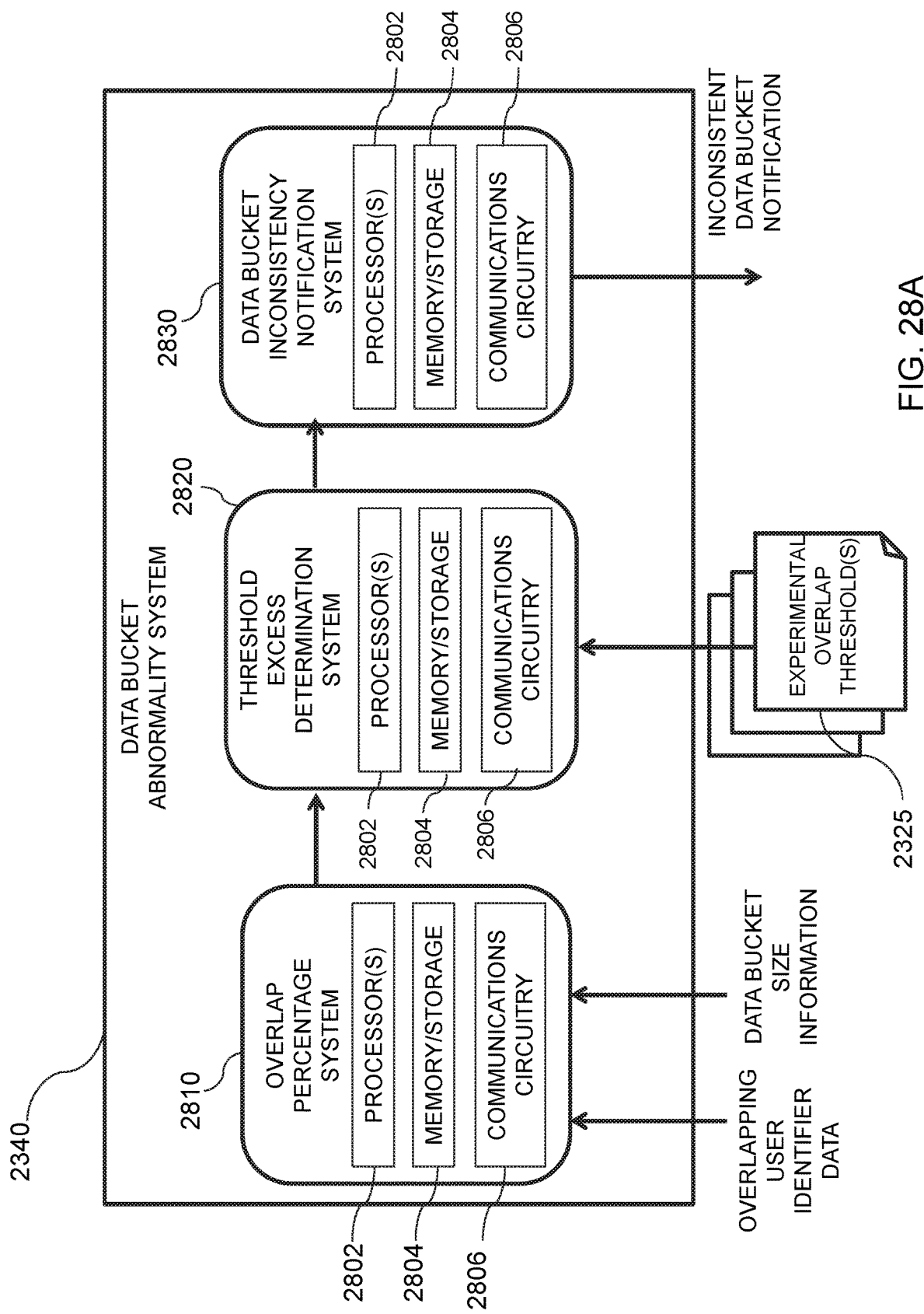
FIG. 28A is an illustrative diagram of an exemplary data bucket abnormality system, in accordance with various embodiments of the present teachings.

FIG. 28A is an illustrative diagram of an exemplary data bucket abnormality system, in accordance with various embodiments of the present teachings. Data bucket abnormality system 2340 may, in the illustrative non-limiting embodiment, include an overlap percentage system 2810, a threshold excess determination system 2820, and a data bucket inconsistency notification system 2830. Each of overlap percentage system 2810, threshold excess determination system 2820, and data bucket inconsistency notification system 2830 may include one or more processors 2802, memory/storage 2804, and communications circuitry 2806. Processor(s) 2802, memory/storage 2804, and communications circuitry 2806 may, in some embodiments, be substantially similar to processor(s) 402, memory/storage 404, and communications circuitry 406 of FIG. 4, and the previous description may apply.

Overlap percentage system 2810, in some embodiments, may be configured to receive overlapping user identifier data from system 2330, as well as data bucket size information, and may determine a percentage of overlap for a particular data bucket. For example, as mentioned previously, if 100 user identifiers of a first data bucket are determined to be associated with a second data bucket, and the total number of identifiers in the first data bucket is approximately 1,000 identifiers, then the percentage of overlap determined by system 2810 would be approximately 10%. Persons of ordinary skill in the art will recognize that a number of identifiers in each data bucket of a same experiment is substantially consistent across each data bucket, and therefore the percentage of overlap may be considered with respect to any of the data buckets under consideration.

Threshold excess determination system 2820, in some embodiments, may be configured to determine whether or not the overlap percentage is in excess of an experimental overlap threshold 2325. For example, if the threshold for an experiment is set at 10%, and the overlap is 20%, then threshold excess determination system 2820 may determine that the overlap exceeds the threshold. However, if the overlap is 10% and the threshold is 20%, then system 2820 may determine that the overlap does not exceed the threshold. Persons of ordinary skill in the art will recognize that different experiments may employ different thresholds 2325, which may also be based on a sample size associated with an experiment, and the aforementioned are purely exemplary.

Data bucket inconsistency notification system 2830 may be configured, in some embodiments, to determine whether threshold excess determination system 2820 indicates that the overlap exceeds the threshold, or does not exceed threshold, and may generate output data reflective of the results. For example, if data bucket inconsistency notification system 2830 determines that the overlap exceeds the threshold for the experiment, then system 2830 may generate an inconsistent data bucket notification, which may be provided to an experiment designer to indicate that an inconsistency in the distribution of user identifiers within an experiment is present.

Figure 28B:
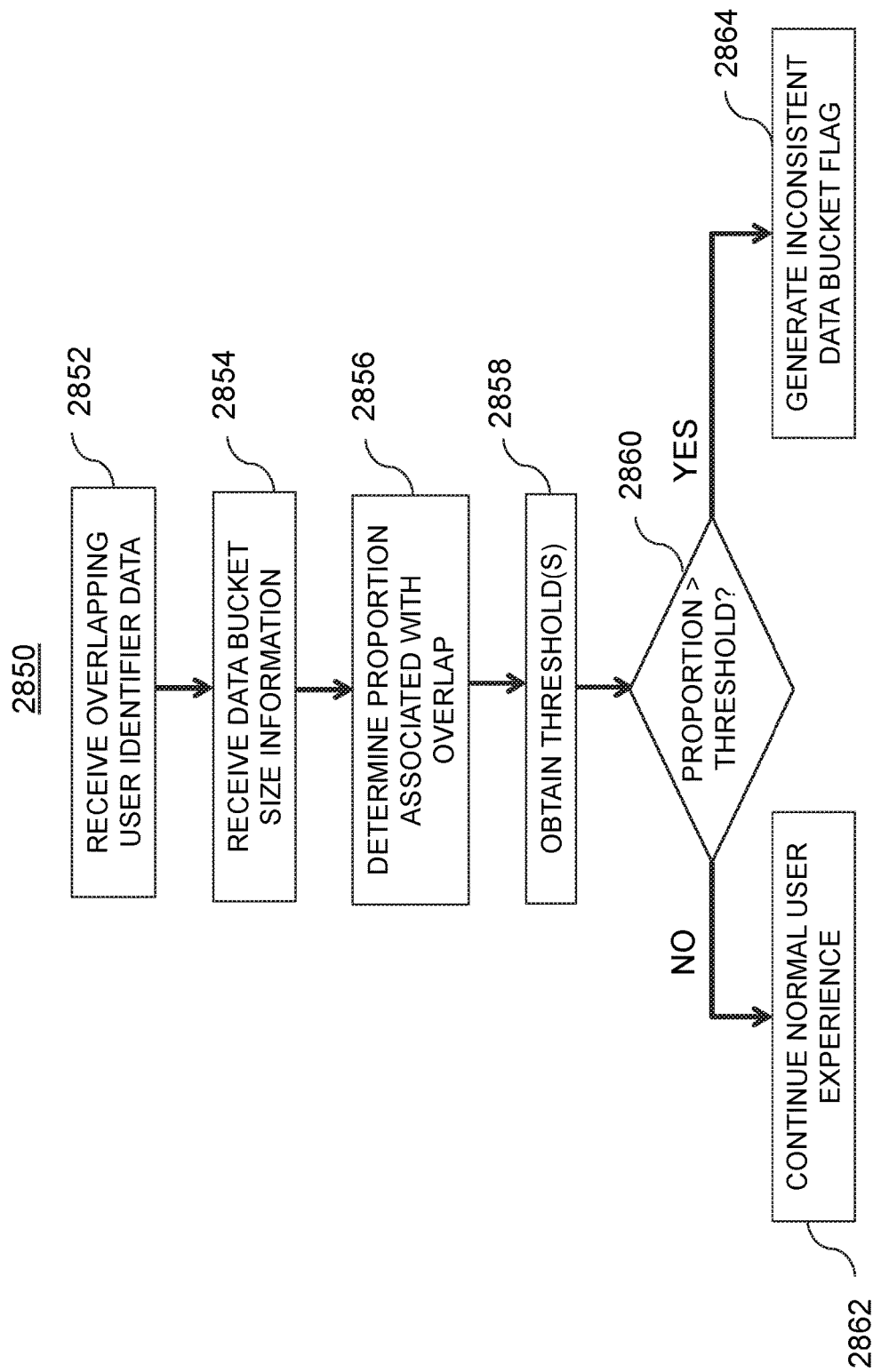
FIG. 28B is an illustrative flowchart of an exemplary processor for determining whether to generate an inconsistent data bucket flag, in accordance with various embodiments of the present teachings.

FIG. 28B is an illustrative flowchart of an exemplary processor for determining whether to generate an inconsistent data bucket flag, in accordance with various embodiments of the present teachings. Process 2850, in a non-limiting embodiment, may begin at step 2852. At step 2852, overlapping user identifier data may be received. For instance, overlapping user identifier data may be received from user identification comparison system 2330. At step 2854, data bucket size information may be received. The data bucket size information may indicate a sample size associated with the data bucket that the overlap was detected for.

At step 2856, a proportion associated with the overlap may be determined. For example, a proportion of the overlap as compared to the total data bucket size may be determined. At step 2858, thresholds associated with the online experiment that the data bucket is associated with may be obtained. For instance, thresholds 2325 for the online experiment associated with the overlapping user identifier data's data bucket may be obtained. At step 2860, a determination may be made as to whether the proportion is greater than the threshold. If, at step 2860, it is determined that the proportion is not greater than threshold, then process 2850 may proceed to step 2862. At step 2862, normal user experience may continue. For example, each user identifier of the online experiment may continue to receive their appropriate user experience based on the data bucket assigned thereto. However, if at step 2860 it is determined that the proportion is greater than the threshold, the process 2850 may proceed to step 2864. At step 2864, an inconsistent data bucket flag may be generated. For example, data bucket inconstancy notification system 2830 may generate an inconsistent data bucket notification indicating that an overlap exists for a particular data bucket of an experiment, and that the overlap exceeds a threshold. This may indicate that the results of the experiment may be incorrect/inaccurate, thereby invalidating the experiment. Furthermore, this allows an experiment designer to research into the possible causes of the error to eliminate them, thereby potentially salvaging the experiment.

Figure 29A:
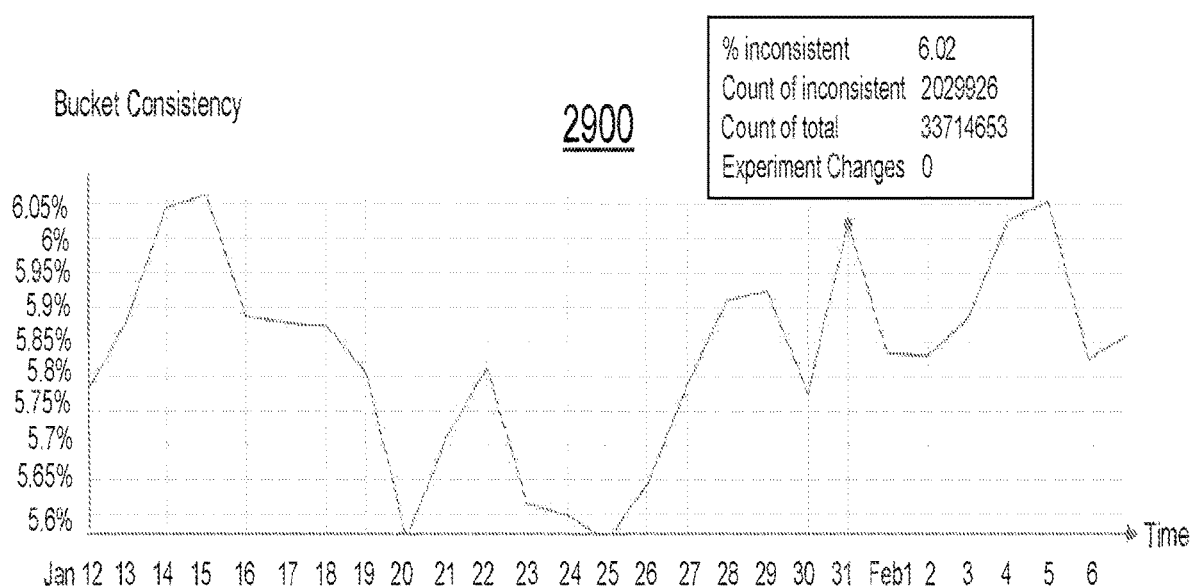
FIGS. 29A and 29B are illustrative graphs indicating data bucket inconstancies over time and data bucket inconstancies within a threshold limit, in accordance with various embodiments of the present teachings.
Figure 29B:
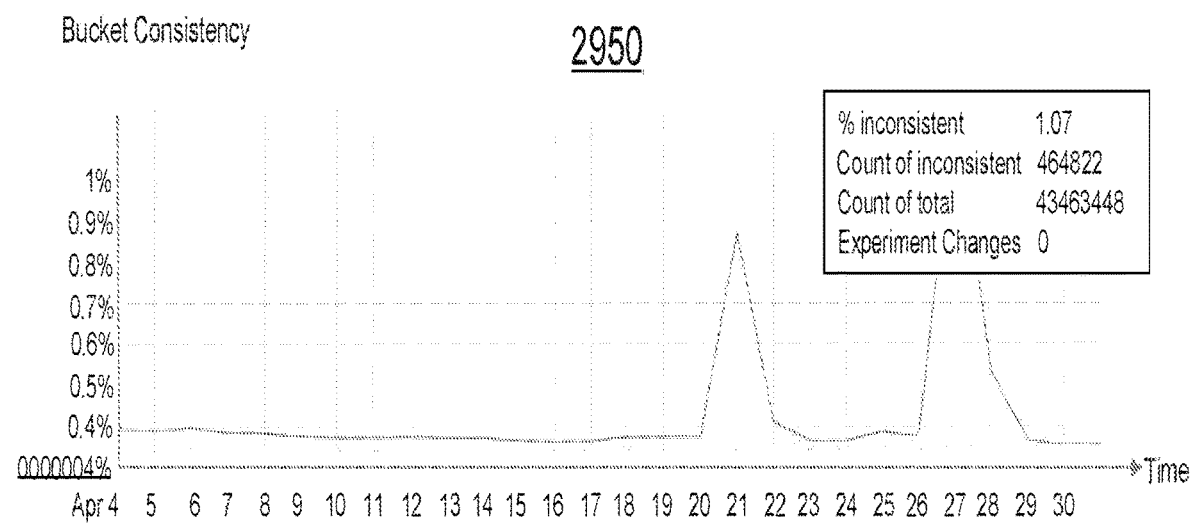

FIGS. 29A and 29B are illustrative graphs indicating data bucket inconstancies over time and data bucket inconstancies within a threshold limit, in accordance with various embodiments of the present teachings. Graph 2900 of FIG. 29A corresponds to a graph indicating a change in bucket consistency over time. As compared to graph 2100 of FIG. 21, even though the data buckets may appear to be consistent in terms of sample size over time, graph 2900 of FIG. 29A indicates that there may still exists inconsistencies across the data buckets over time. This inconsistency, as mentioned above, not only affects the experiment's validity, but also may affect a user's experience with the content provider associated with the experiment. FIG. 29B, however, includes graph 2950, which illustrates an exemplary embodiment where inconsistencies have been minimized. For instance, over time, the inconstancies are fairly minimal (e.g., less than 1%). The minimal inconsistencies reflected herein may result in changes to the experiment's setup such as, and without limitation, metadata changes and/or data bucket opt-in configurations.

Figure 30:
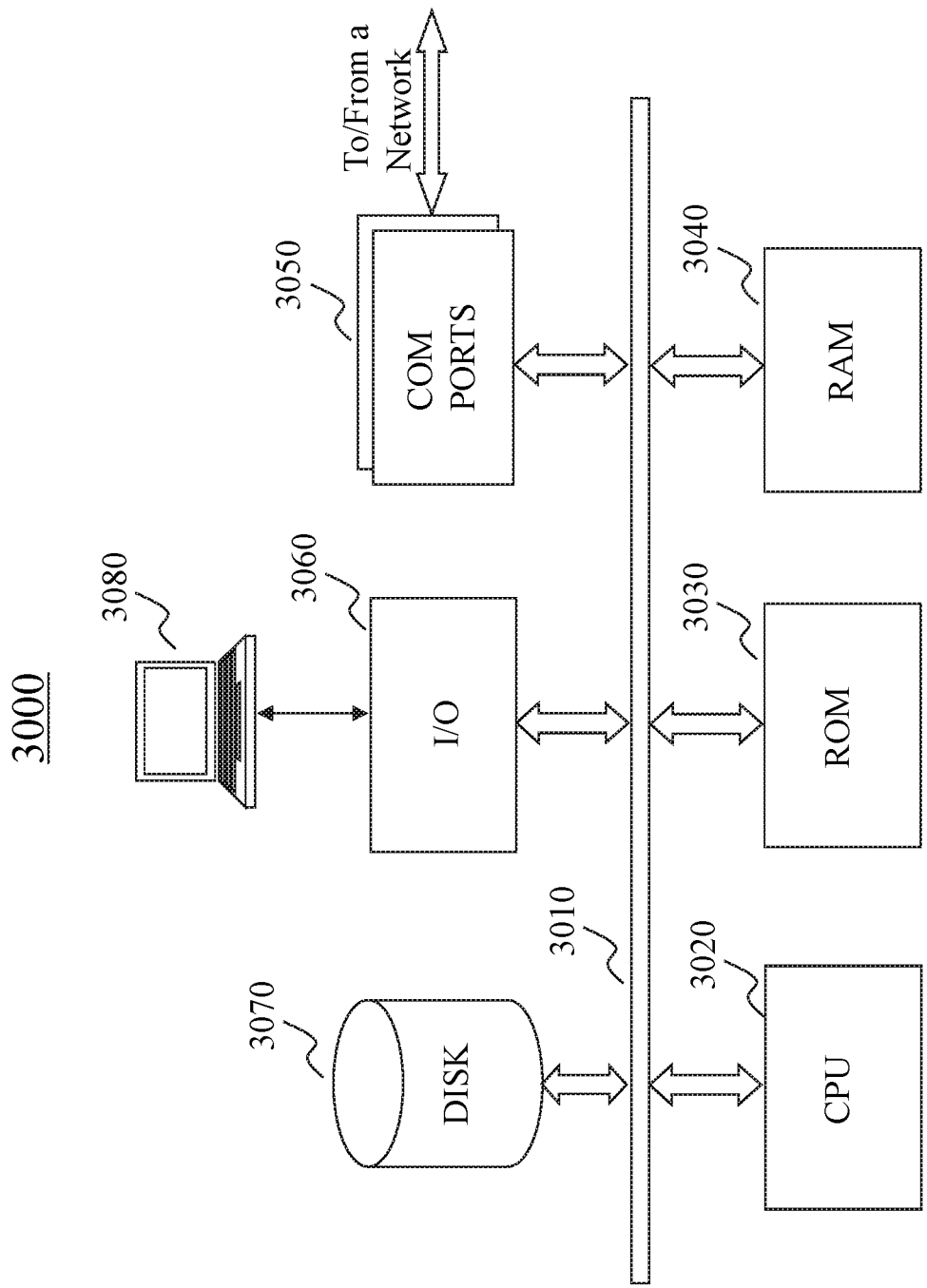
FIG. 30 is an illustrative diagram of exemplary computing system architecture, in accordance with various embodiments of the present teaching.

FIG. 30 is an illustrative diagram of exemplary computing system architecture, in accordance with various embodiments of the present teaching. Such a specialized system incorporating the present teaching has a functional block diagram illustration of a hardware platform which includes user interface elements. Computer 3000 may be a general purpose computer or a special purpose computer. Both can be used to implement a specialized system for the present teaching. Computer 3000 may be used to implement any component of the user activity detection system, as described herein. For example, data pipeline 130, discrepancy detection system 1040, and data inconsistency detection system 2030 may each be implemented on a computer such as computer 3000 via its hardware, software program, firmware, or a combination thereof. However, other components/systems of the aforementioned figures may additionally or alternatively be implemented on a computer such as computer 3000 via its hardware, software program, firmware, or combination thereof, and the aforementioned is merely exemplary. Although only one such computer is shown, for convenience, the computer functions relating to the various embodiments described herein may be implemented in a distributed fashion on a number of similar platforms, to distribute the processing load.

Computer 3000, for example, may include COM ports 3050 connected to and from a network connected thereto to facilitate data communications. Computer 3000 also includes a central processing unit (CPU) 3020, in the form of one or more processors, for executing program instructions. For example, CPU 3020 may include one or more processors such as those described by processor(s) 402. The exemplary computer platform may also include an internal communication bus 3010, program storage and data storage of different forms (e.g., disk 3070, read only memory (ROM) 3030, or random access memory (RAM) 3040), for various data files to be processed and/or communicated by computer 3000, as well as possibly program instructions to be executed by CPU 3020. For instance, one or more of memory/storage 404 may be included by ROM 3030 and/or RAM 3040, as described in greater detail above. Computer 3000 may also include an I/O component 3060 supporting input/output flows between the computer and other components therein such as user interface elements 3080. Computer 3000 may also receive programming and data via network communications, such as via communications circuitry similar to communications circuitry 406 described in greater detail above.

Hence, aspects of the aforementioned embodiments, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of abnormal user activity processing operator or other abnormal user activity detection system into the hardware platform(s) of a computing environment or other system implementing a computing environment or similar functionalities in connection with abnormal user activity detection. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the abnormal user activity detection system, as disclosed herein, may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method for providing pre-validated data buckets for online experiments, comprising:
    obtaining historical user activity data representing online activities of a plurality of users each having a corresponding user identifier;
    hashing each of the plurality of user identifiers to obtain a plurality of hash values;
    obtaining a set of metric values based on the historical user activity data, wherein the set of metric values represents user engagement of the plurality of users;
    ranking the plurality of hash values of the plurality of users based on the set of metric values to obtain a ranked list of hash values; and
    removing one or more of hash values from the ranked list based on an exclusion range rule provided for excluding users with hash values in a predetermined range, wherein the remaining hash values in the ranked list are to be placed in a data bucket for an online experiment, wherein the exclusion range rule indicates to exclude the one or more of hash values flagged by a metadata tag, and wherein the metadata tag indicates that the one or more of hash values are either unavailable for placement or should not be used in the data bucket for the online experiment.

2. The method of claim 1, wherein the exclusion range rule indicates the predetermined range.

3. The method of claim 1, wherein the exclusion rule comprises selecting a first subset of hash values having a highest ranking in the ranked list of hash values and a second subset of hash values having a lowest ranking in the ranked list of hash values.

4. The method of claim 1, wherein the set of metric values comprises at least one of:
    a days visited parameter corresponding to a number of days that a first user identifier visited a uniform resource locator for a website associated with the online experiment;
    a webpage view parameter; or
    a user session parameter.

5. A non-transitory, computer-readable medium having information recorded thereon for providing pre-validated data buckets for online experiments, wherein the information, when read by a machine, causes the machine to perform operations comprising:
    obtaining historical user activity data representing online activities of a plurality of users each having a corresponding user identifier;
    hashing each of the plurality of user identifiers to obtain a plurality of hash values;

obtaining a set of metric values based on the historical user activity data, wherein the set of metric values represents user engagement of the plurality of users;

ranking the plurality of hash values of the plurality of users based on the set of metric values to obtain a ranked list of hash values; and removing one or more of hash values from the ranked list based on an exclusion range rule provided for excluding users with hash values in a predetermined range, wherein the remaining hash values in the ranked list are to be placed in a data bucket for an online experiment, wherein the exclusion range rule indicates to exclude the one or more of hash values flagged by a metadata tag, and wherein the metadata tag indicates that the one or more of hash values are either unavailable for placement or should not be used in the data bucket for the online experiment.

6. The medium of claim 5, wherein the exclusion range rule indicates the predetermined range.

7. The medium of claim 5, wherein the exclusion rule comprises selecting a first subset of hash values having a highest ranking in the ranked list of hash values and a second subset of hash values having a lowest ranking in the ranked list of hash values.

8. The medium of claim 5, wherein the set of metric values comprises at least one of:
- a days visited parameter corresponding to a number of days that a first user identifier visited a uniform resource locator for a website associated with the online experiment;
- a webpage view parameter; or
- a user session parameter.

9. A system for providing pre-validated data buckets for online experiments, the system comprising:

memory storing computer program instructions; and one or more processors that, in response to executing the computer program instructions, effectuate operations comprising:

obtaining historical user activity data representing online activities of a plurality of users each having a corresponding user identifier;

hashing each of the plurality of user identifiers to obtain a plurality of hash values;

obtaining a set of metric values based on the historical user activity data, wherein the set of metric values represents user engagement of the plurality of users;

ranking the plurality of hash values of the plurality of users based on the set of metric values to obtain a ranked list of hash values; and removing one or more of hash values from the ranked list based on an exclusion range rule provided for excluding users with hash values in a predetermined range, wherein the remaining hash values in the ranked list are to be placed in a data bucket for an online experiment, wherein the exclusion range rule indicates to exclude the one or more of hash values flagged by a metadata tag, and wherein the metadata tag indicates that the one or more of hash values are either unavailable for placement or should not be used in the data bucket for the online experiment.

10. The system of claim 9, wherein the exclusion range rule indicates the predetermined range.

11. The system of claim 9, wherein the exclusion rule comprises selecting a first subset of hash values having a highest ranking in the ranked list of hash values and a second subset of hash values having a lowest ranking in the ranked list of hash values.

* * * * *